United States Patent
Nagao et al.

(12) 
(10) Patent No.: US 6,335,366 B2
(45) Date of Patent: Jan. 1, 2002

(54) NAPHTHYLOXY ACETIC ACID DERIVATIVES AND A PHARMACEUTICAL COMPOSITION COMPRISING THEM AS AN ACTIVE INGREDIENT

(75) Inventors: Yuuki Nagao; Kazuhiko Torisu; Nobuyuki Hamanaka, all of Mishima-gun (JP)

(73) Assignee: Ono Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 09/765,676

(22) Filed: Jan. 22, 2001

Related U.S. Application Data

(62) Division of application No. 09/440,674, filed on Nov. 16, 1999, now Pat. No. 6,197,993, which is a division of application No. 09/000,102, filed as application No. PCT/JP96/01833 on Jul. 2, 1996, now Pat. No. 6,018,068.

(51) Int. Cl.[7] .................. A61K 31/185; A61K 31/21
(52) U.S. Cl. ................ 514/534; 560/19; 560/37; 562/433; 564/337; 564/338; 514/538; 514/539; 514/561; 514/648
(58) Field of Search .............. 560/19, 37, 42, 560/43; 562/405, 433, 442, 511, 553; 564/55, 57, 58, 337, 338, 339; 514/506, 507, 534, 538, 539, 561, 648, 659

(56) References Cited

U.S. PATENT DOCUMENTS

| | | |
|---|---|---|
| 3,930,672 A | 1/1976 | Ozutsumi et al. |
| 4,327,022 A | 4/1982 | Bailey |
| 4,424,231 A | 1/1984 | Bantick et al. |
| 4,707,497 A | 11/1987 | Cecchi et al. |
| 4,927,955 A | 5/1990 | Boigegrain et al. |
| 5,130,339 A | 7/1992 | Cecchi et al. |
| 5,236,951 A | 8/1993 | Manara |
| 5,312,961 A | 5/1994 | Guzzi et al. |
| 5,461,045 A | 10/1995 | Hamanaka et al. |
| 5,488,151 A | 1/1996 | Baroni et al. |
| 5,624,959 A | 4/1997 | Nagao et al. |

FOREIGN PATENT DOCUMENTS

| | | |
|---|---|---|
| EP | 181568 | 5/1986 |
| WO | 9218461 | 10/1992 |

OTHER PUBLICATIONS

CA:115:207684 abs of EP46435 Jul. 1991.*
CA:114:12185045 abs of EP383686 Aug. 1990.*
CA:111:23206 abs of EP303545 Feb. 1989.*
CA:112:76644 abs of EP325963 Aug. 1989.*
CA:118:101674 abs of WO 9218461 Oct. 1992.*
CA:120:106568 abs of WO 9315041 Aug. 1993.*
CA:128:43423 abs of J Med Chem by Mewshaw et al 40(26) pp. 4235–4256 1997.*
C.A. 20608f (1975)=JP Kokai Sho 50–89352.
CA. 116:193858 abs of Eur J Med Chem by Perrone et al 26 (9) pp. 869–74.
CA: 112:215754 abs of Tetrahedron Lett 30 (52) pp. 7301–4.

* cited by examiner

*Primary Examiner*—Jean F. Vollano
(74) *Attorney, Agent, or Firm*—Stevens, Davis, Miller & Mosher, L.L.P.

(57) ABSTRACT

The naphthyloxyacetic acid derivatives of the formula (I)

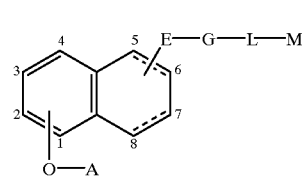

wherein A is H, -(alkylene)COOR$^1$, -(alkylene)CONR$^2$R$^3$, -(alkylene)OH, -(alkylene)tetrazole, -(alkylene)CN; E is single bond or alkylene; G is —S—, —SO—, —SO$_2$—, —O— or —NR$^4$—; L is alkylene, —(CH$_2$)$_m$—CH=CH—(CH$_2$)$_n$— or —(CH$_2$)$_x$—CH(OH)—(CH$_2$)$_y$—; M is phenyl, phenyl(thio, oxy, amino), diphenylmethyl, diphenylmethyl (thio, oxy, amino), and pharmaceutical composition comprising them as an active ingradient. The compounds of the formula (I) can combine PGE$_2$ receptor and exhibit the activity to antagonize or agonize for PGE$_2$ receptor. Therefore, they are useful as anti-hyperlipemia, for the prevention of abortion, for analgesics, as antidiarrheals, sleep inducer, diuretic, anti-diabetes, abortient, cathartics, antiulcer, anti-gastritis or antihypertensive etc.

6 Claims, No Drawings

NAPHTHYLOXY ACETIC ACID DERIVATIVES AND A PHARMACEUTICAL COMPOSITION COMPRISING THEM AS AN ACTIVE INGREDIENT

CROSS REFERENCE TO RELATED APPLICATIONS

This application is a divisional of U.S. patent application Ser. No. 09/440,674, filed Nov. 16, 1999, now U.S. Pat. No. 6,197,993, which is a divisional of U.S. patent application Ser. No. 09/000,102, now U.S. Pat. No. 6,018,068, filed Jan. 26, 1998, which is a 371 of PCT/JP96/01833 filed Jul. 2, 1996, incorporated herein by reference.

FIELD OF TECHNOLOGY

This invention is related to the naphthyloxyacetic acid derivatives. More particularly, this invention is related to (1) the naphthyloxyacetic acid derivatives of the formula (I)

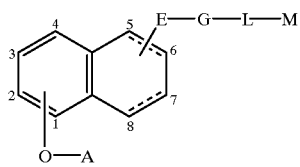

(I)

wherein all symbols are the same meaning as hereafter defined, or non-toxic salts thereof, acid addition salts thereof or their hydrates and (2) a pharmaceutical composition (Prostaglandin $E_2$ ($PGE_2$) antagonists or agonists) which comprises them as an active ingredient.

BACKGROUND $PGE_2$ has been known as metabolite in the arachidonate cascade. In addition, the recent progress in the molecule biological technology makes the existence of three $PGE_2$ receptors clear as shown in the following and have been making the relationship between each receptor and appearance of biological activity clear. For example, $EP_1$ receptor may cause contraction of the smooth muscle of digestive canal or bronchus etc. and promote the release of neurotransmitter. The representative activity of $EP_2$ receptor is relaxation of smooth muscle of bronchus or ileum etc. or vasodilatation and reduce of the blood pressure due to relaxation of vascular smooth muscle. As the activity of $EP_3$ receptor, uterine muscle contraction, suppression of gastric acid secretion, inhibition of reabsorption of water and ion by vasopressin in renes, inhibition of fat decomposition in fat tissue, inhibition of release of neurotransmitter and glucose-decomposition by gulcagon in liver cell etc. have been known. In addition, recently, the existence of fourth receptor is suggested. (Biochemistry Vol. 66, No. 3, pp. 218–231 (1994)).

Therefor, to antagonize $PGE_2$ receptor means to suppress the effects above mentioned, so such an activity is linked to inhibit diuretic, to inhibit hyperlipemia, to inhibit reduce of blood sugar, to inhibit uterine contraction, to have analgesic action, to inhibit digestive peristalsis, to induce sleep. Therefor, $PGE_2$ receptor antagonists are considered to be useful as anti-hyperlipemia, for the prevention of abortion, for analgesics, or as antidiarrheals or sleep inducer.

To agonize for $PGE_2$ receptor means to promote the effects above mentioned, so such an activity is linked to have diuretic, to promote hypedipemia, to promote reduce of blood sugar, to contractile uterine, to promote digestive peristalsis, to suppress gastric acid secretion or to reduce blood pressure. Therefor, $PGE_2$ receptor agonists are considered to be useful for diuretic, anti-diabetes, abortient, cathartics, antiulcer, anti-gastritis or antihypertensive.

In such a background, a lot of compounds which agonize or antagonize for $PGE_2$ receptors have been proposed.

For example, in the specification of EP-0657422, it is disclosed that the compounds of the formula (A)

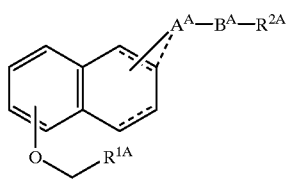

(A)

wherein $R^{1A}$ is —$COOR^{4A}$ in which $R^{4A}$ is hydrogen or C1–4 alkyl,

—$CONR^{5A}$ $R^{6A}$ in which $R^{5A}$ and $R^{6A}$ each, independently, is hydrogen, C1–4 alkyl or C1–4 alkyl substituted by 1 of hydroxy or —$CH_2OH$,

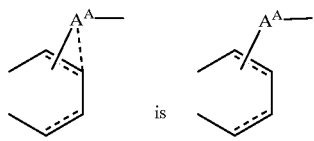

is in which $A^A$ is single bond or C1–4 alkylene or

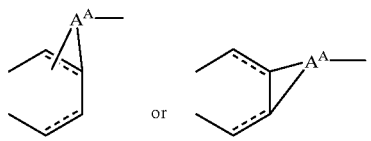

or in which $A^A$ is

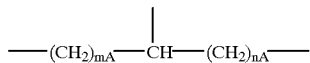

in which mA is 0, 1, 2, 3, 4, nA is 0, 1, 2, 3, 4, and mA+nA is 2, 3, 4,

BA is —$NR^{3A}SO_2$— or —$SO_2NR^{3A}$— in which $R^{3A}$ is hydrogen, C1–4 alkyl or —$CH_2COOR^{7A}$ in which $R^{7A}$ is hydrogen or $R^{4aA}$, in which $R^{4aA}$ is C1–4 alkyl, $R^{2A}$ is (i) C1–6 alkyl, C2–6 alkenyl or C2–6 alkynyl, (ii) C1–6 alkyl, C2–6 alkenyl or C2–6 alkynyl substituted by 1, 2 or 3 of phenyl, C4–7 cycloalkyl or phenyl substituted by 1, 2 or 3 substituents selected from C1–4 alkyl, C1–4 alkoxy or halogen or (iii) naphthyl, in the formula

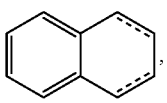

---- is single bond or double bond, or non-toxic salts thereof, are useful as PGE$_2$ antagonist or agonist.

In the specification of EP-0578847 (corresponding to JP Patent Application Kokai Hei 6-25074), it is disclosed that the compounds of the formula (B)

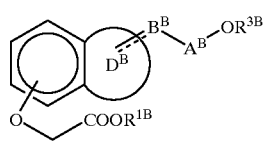 (B)

wherein, 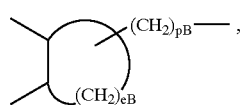 is

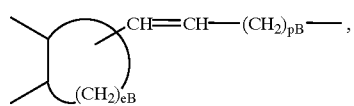 (i)

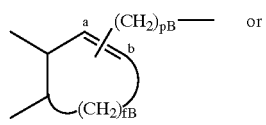 (ii)

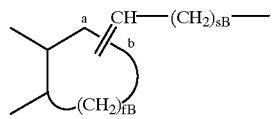 (iii)

or

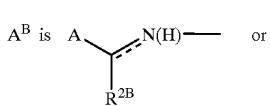 (iv)

$A^B$ is  or (i)

(ii)

$R^{1B}$ is hydrogen or C1–4 alkyl,
$R^{2B}$ is hydrogen, C1–6 alkyl or phenyl,
$R^{3B}$ is
  (i) C1–15 alkyl,
  (ii) C1–8 alkyl substituted by 1 or 2 of benzene ring, C4–7 cycloalkyl or 4–7 membered monocyclic ring containing one nitrogen,
  (iii) C10–15 fused tricyclic ring,
$e^B$ is an integer of 3–5,
$f^B$ is an integer of 1–3,
$p^B$ is 0 or an integer of 1–4,
$q^B$ is 0, 1 or 2,
$s^B$ is 0or an integer of 1–3;
with the proviso that, when

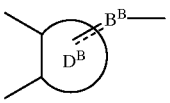

is (iii) or (iv), —(CH$_2$)$_p^B$— and =CH—(CH$_2$)$_s^B$— is bonded at the position a or b on the ring, and the ring in $R^{3B}$ may be substituted by one to three of C1–4 alkyl, C1–4 alkoxy, halogen, nitro or trihalomethyl, are useful as PGl$_2$ agonist.

In the specification of JP Patent Application Kokai Sho 61-267532, it is disclosed that the compounds of the formula (D)

$$Ar^{1D}-X^D-Ar^D-Z^D-(R^D)_n^{D'}$$ (D)

wherein $Ar^{1D}$ is a nitrogen, sulfur or oxygen containing heterocyclic ring or an aromatic ring, $Ar^D$ is a phenyl or nitrogen, oxygen or sulfur containing heterocyclic ring, $Ar^{1D}$ and Ar may be fully substituted or less than fully substituted by H, CH$_3$, lower alkyl, aryl, aralkyl, halogen, hydroxy, lower alkoxy, CF$_3$, COOH, alkylcarboxy, arylcarboxy, alkylcarbalkoxy, alkanoyl, formyl, oxo, nitrilo, amino, aminoalkyl, alkylamine, carboxyamide, aryloxy, nitro, sulfonyl, sulfonamide, thio, alkylthio, hydroxyalkyl or oxyalkylcarboxy, $X^D$ is —O(CHR$^{1D}$)$_n^D$—, —S(O)$_n^{D''}$—(CHR$^{1D}$)$_n^D$—, —NR$^{1D}$(CHR$^{1D}$)$_n^D$-alkylene of up to 2 carbon atoms in the principal chain and up to a total 4 carbon atoms, —C(R$^{1D}$)=(CR$^{1D}$)—, —C≡C—, —CO(CHR$^{1D}$)$_n^{D'}$—, —CH(OH)—(CHR$^{1D}$)$_n^D$—, —CH=N—, —CO—O—, —CO—S—, or —CO—N(R$^{1D}$)—, $Z^D$ is an alkylene containing up to 10 carbon atoms in principal chain and a total of up to 12 carbon atoms and from 0 to 2 double bonds and the said alkylene chain may be attached to Ar$^D$ through an oxygen, sulfur or amino nitrogen atom, and when $n^{D'}$ is 2 or more, one of the $R^D$ substituents may be halogen on an omega carbon of the alkylene chain $Z^D$, when $n^{D'}$ is 1, $R^D$ is a substituent attached to one of the carbon atoms of $Z^D$ selected from the group consisting of oxo, OR$^{3D}$, SR$^{3D}$, N(R$^{2D}$)$_2$, R$^{1D}$ and —COR$^{4D}$, when $n^{D'}$ is 2 or more, one $R^D$ is as previously defined, and the other $R^D$ is a substituent attached to one of the carbon atoms of $Z^D$ selected from the group consisting of oxo, OR$^{3D}$, SR$^{3D}$, N(R$^{2D}$)$_2$, —COR$^{4D}$, lactone and halogen, $R^{1D}$ is H or CH$_3$,
$R^{2D}$ is H, lower alkyl, aryl or aralkyl,
$R^{3D}$ is H, lower alkyl, lower alkanoyl, aryl, aralkyl or substituted aryl in which the substituent is halogen, lower alkyl or lower alkoxy,
$R^{4D}$ is OR$^{2D}$ or N(R$^{2D}$)$_2$,
$n^D$ is 0 or 1,
$n^{D'}$ is an integer of 1–7,
$n^{D''}$ is 0, 1 or 2, possess the anti-inflammatory and anti-allergic activity due to lipoxygenase inhibition.

In addition, in the specification of (E) U.S. Pat. No. 4,327,022, (F) JP Patent Application Kokai Sho 50-89352 and (G) U.S. Pat. No. 3,930,672, it is disclosed that the naphthol derivatives are useful as (1) cardiotonic or anti-bacterial agents, (2) analgesic, anti-inflammatory and anti-pyretic agent and (3) starting material of the compound related to copy paper, respectively.

DISCLOSURE OF THE INVENTION

Purpose of the Invention

The present inventors have been studding in order to find out PGE$_2$ antagonist or agonist which have new skeleton in structure, and then have found out that the naphthyloxy acetic acid derivatives (compounds of the formula (I) as mentioned hereinafter) in which thioether, sulfinyl, sulfonyl, ether or amine are introduced into the side chain are useful as PGE$_2$ antagonist or agonist, particularly, the mentioned compounds can bind the EP$_3$ receptor strongly. And then, the present invention has been completed.

Comparison with Related Art

The compounds of the formula (A) as mentioned in Related Art possess —NR$^{3A}$SO$_2$— or —SO$_2$NR$^{3A}$ wherein all symbols are the same meaning as defined hereinbefore, in the side chain as basic structure. On the other hand, corresponding part in the present invention compounds is thioether, sulfinyl, sulfonyl, ether or amine.

The compounds of the formula (B), (D) and the compounds described in (E), (F) and (G) as mentioned in Related Art possess (1) PGI$_2$ agnostic activity, (2) anti-inflammatory and anti-allergic activity due to lipoxygenase inhibition (3) cardiotonic or anti-bacterial agents, (4) analgesic, anti-inflammatory and antipyretic agent and (5) starting material of the compound related to copy paper, respectively. On the other hand, the present invention compounds possess the PGE$_2$ antagonistic or agnostic activity.

That is to say, the present invention provides:

1) a naphthyloxyacetic acid derivative of the formula (I)

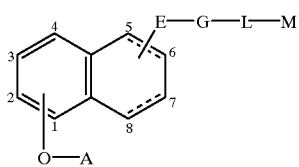

(I)

wherein A is
(i) hydrogen,
(ii) —(C1-4 alkylene)—COOR$^1$ in which R$^1$ is hydrogen or C1-4 alkyl,
(iii) —(C1-4 alkylene)—CONR$^2$R$^3$ in which R$^2$ and R$^3$ each, independently, is hydrogen or C1-4 alkyl,
(iv) —(C1-4 alkylene)—OH,
(v) —(C1-4 alkylene)-tetrazolyl or
(vi) —(C1-4 alkylene)—CN;

E is
(i) single bond or
(ii) C1-6 alkylene;

G is —S—, —SO—, —SO$_2$—, —O— or —NR$^4$— in which, R$^4$ is hydrogen or C1-4 alkyl;

L is (i) C1-6 alkylene,
(ii) —(CH$_2$)$_m$—CH=CH—(CH$_2$)$_n$— in which m is 0 or an integer of 1–3, n is 0 or an integer of 1–3 or
(iii) —(CH$_2$)$_x$—CH(OH)—(CH$_2$)$_y$— in which x is an integer of 1–3, y is 0 or an integer of 1–3;

M is

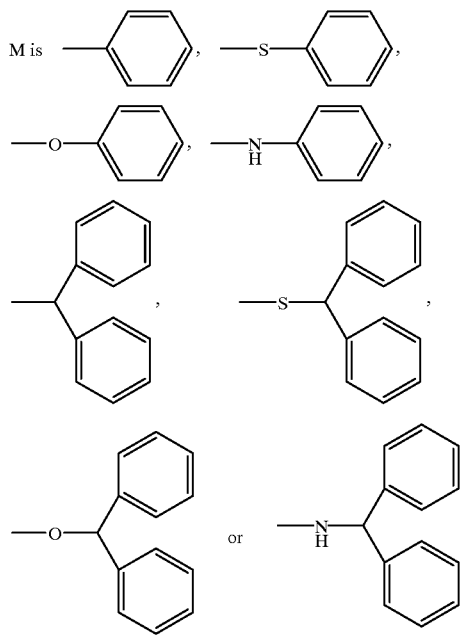

in which each phenyl group may be substituted by 1–3 of C1-4 alkyl, C1-4 alkoxy, halogen, nitro or trifluoromethyl;

in the formula

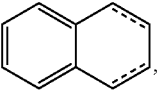

----- is single bond or double bond;

with the proviso that, (1) when G is —SO— or —SO$_2$—, M is neither

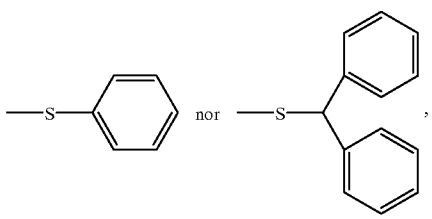

in which each phenyl group may be substituted by 1–3 of C1-4 alkyl, C1-4 alkoxy, halogen, nitro or trifluoromethyl, (2) when m in L is 0, G is —SO— or —SO$_2$—, (3) when n in L is 0, M is

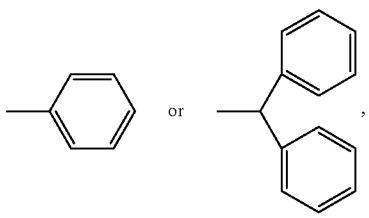

in which each phenyl group may be substituted by 1–3 of C1–4 alkyl, C1–4 alkoxy, halogen, nitro or trifluoromethyl, (4) when y in L is 0, M is

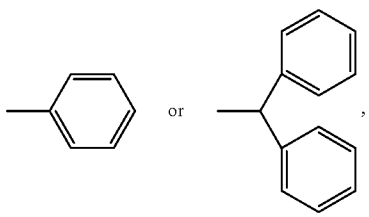

in which each phenyl group may be substituted by 1–3 of C1–4 alkyl, C1–4 alkoxy, halogen, nitro or trifluoromethyl, (5) when A is hydrogen, L is —(CH$_2$)$_m$—CH=CH—(CH$_2$)$_n$— in which m and n are the same meaning as hereinbefore defined, or —(CH$_2$)$_x$—CH(OH)—(CH$_2$)$_y$, in which x and y are the same meaning as hereinbefore defined, and (6) tetrazolyl in A is

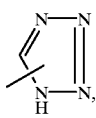

or non-toxic salt thereof, non-toxic acid addition salt thereof or their hydrate, 2) a compound described in 1), wherein A is —(C1–4 alkylene)—COOR$^1$, 3) a compound described in 1), wherein A is —(C1–4 alkylene)—CONR$^2$R$^3$, —C1–4 alkylene)—OH, —(C1–4 alkylene)-tetrazolyl or —(C1–4 alkylene)—CN, 4) a compound described in 1), wherein A is hydrogen, 5) a compound described in 1)-5), wherein L is —(CH$_2$)$_m$—CH=CH—(CH$_2$)$_n$ or —(CH$_2$)$_x$—CH(OH)—(CH$_2$)$_y$—, 6) a compound described in 5), wherein G is —S—, —SO— or —SO$_2$—, 7) a compound described in 5), wherein G is —O—, 8) a compound described in 5), wherein G is —NR$^4$—, 9) a compound described in 6), which is (1) 1-[2-(5-hydroxy-1-naphthyl)ethylthio]-3-phenoxy-2RS-propanol, (2) 1-[2-(5-hydroxy-1-naphthyl)ethylsulfinyl]-3-phenoxy-2RS-propanol, (3) 1-[2-(5-hydroxy-1-naphthyl)ethylsulfonyl]-3-phenoxy-2RS-propanol, (4) 1-[2-(5-hydroxy-1-naphthyl)ethylthio]-3-phenoxy-2R-propanol, (5) 1-[2-(5-hydroxy-1-naphthyl)ethylthio]-3-phenoxy-2S-propanol, (6) 1-(5-hydroxy-1-naphthyl)methylthio-3-phenoxy-2RS-propanol, (7) 1-(5-hydroxy-1-naphthyl)methylsulfinyl-3-phenoxy-2RS-propanol, (8) 1-(5-hydroxy-1-naphthyl)methylsulfonyl-3-phenoxy-2RS-propanol, (9) 2-[3-(5-hydroxy-1-naphthyl)propylthio]-1-phenyl-1RS-ethanol,

(10) 2-[3-(5-hydroxy-1-naphthyl)propylsulfinyl]-1-phenyl-1RS-ethanol,

(11) 2-[3-(5-hydroxy-1-naphthyl)propylsulfonyl]-1-phenyl-1RS-ethanol,

(12) 1-(5-hydroxy-1-naphthyl)thio-3-phenoxy-2RS-propanol,

(13) 1-(5-hydroxy-1-naphthyl)sulfinyl-3-phenoxy-2RS-propanol,

(14) 1-(5-hydroxy-1-naphthyl)sulfonyl-3-phenoxy-2RS-propanol,

(15) 1-[2-(5-hydroxy-1-naphthyl)ethylthio]-3-(4-chlorophenoxy)-2RS-propanol,

(16) 1-[2-(5-hydroxy-1-naphthyl)ethylthio]-3-(4-methylphenoxy)-2RS-propanol,

(17) 1-[2-(5-hydroxy-1-naphthyl)ethylthio]-3-(4-methoxyphenoxy)-2RS-propanol,

(18) 1-[2-(5-hydroxy-1-naphthyl)ethylthio]-3-diphenylmethoxy-2RS-propanol,

(19) 1-[2-(5-hydroxy-1-naphthyl)ethylthio]-3-[1-phenyl-1-(4-chlorophenyl)methoxy]-2RS-propanol,

(20) 1-[2-(5-hydroxy-1-naphthyl)ethylthio]-3-phenylthio-2RS-propanol,

(21) 1-(5-hydroxy-1-naphthyl)methylthio-3-diphenylmethoxy-2RS-propanol,

(22) 1-(5-hydroxy-1-naphthyl)methylthio-3-[1-phenyl-1-(4-chlorophenyl)methoxy]-2RS-propanol,

(23) 2-{5-[2-(2RS-hydroxy-3-phenoxypropylthio)ethyl]-1-naphthyloxy}acetic acid methyl ester,

(24) 2-{5-[2-(2RS-hydroxy-3-phenoxypropylsulfinyl)ethyl]-1-naphthyloxy}acetic acid methyl ester,

(25) 2-{5-[2-(2RS-hydroxy-3-phenoxypropylsulfonyl)ethyl]-1-naphthyloxy}acetic acid methyl ester,

(26) 2-{5-[2-(2R-hydroxy-3-phenoxypropylthio)ethyl]-1-naphthyloxy}acetic acid methyl ester,

(27) 2-{5-[2-(2S-hydroxy-3-phenoxypropylthio)ethyl]-1-naphthyloxy}acetic acid methyl ester,

(28) 2-[5-(2RS-hydroxy-3-phenoxypropylthio)methyl-1-naphthyloxy]acetic acid methyl ester,

(29) 2-[5-(2RS-hydroxy-3-phenoxypropylsulfinyl)methyl-1-naphthyloxy]acetic acid methyl ester,

(30) 2-[5-(2RS-hydroxy-3-phenoxypropylsulfonyl)methyl-1-naphthyloxy]acetic acid methyl ester,

(31) 2-{5-[3-(2RS-hydroxy-2-phenylethylthio)propyl]-1-naphthyloxy}acetic acid methyl ester,

(32) 2-{5-[3-(2RS-hydroxy-2-phenylethylsulfinyl)propyl]-1-naphthyloxy}acetic acid methyl ester,

(33) 2-{5-[3-(2RS-hydroxy-2-phenylethylsulfonyl)propyl]-1-naphthyloxy}acetic acid methyl ester,

(34) 2-[5-(2RS-hydroxy-3-phenoxypropylthio)-1-naphthyloxy]acetic acid methyl ester,

(35) 2-[5-(2RS-hydroxy-3-phenoxypropylsulfinyl)-1-naphthyloxy]acetic acid methyl ester,

(36) 2-[5-(2RS-hydroxy-3-phenoxypropylsulfonyl)-1-naphthyloxy]acetic acid methyl ester,

(37) 2-[5-(3-styrylsulfonylpropyl)-1-naphthyloxy]acetic acid methyl ester,

(38) 2-[5-(3-styrylsulfinylpropyl)-1-naphthyloxy]acetic acid methyl ester,

(39) 2-{5-[2-(2RS-hydroxy-3-(4-chlorophenoxy) propylthio)ethyl]-1-naphthyloxy}acetic acid methyl ester,
(40) 2-{5-[2-(2RS-hydroxy-3-(4-methylphenoxy) propylthio)ethyl]-1-naphthyloxy}acetic acid methyl ester,
(41) 2-{5-[2-(2RS-hydroxy-3-(4-methoxyphenoxy) propylthio)ethyl]-1-naphthyloxy}acetic acid methyl ester,
(42) 2-{5-[2-(2RS-hydroxy-3-diphenylmethoxypropylthio)ethyl]-1-naphthyloxy}acetic acid methyl ester,
(43) 2-{5-[2-(2RS-hydroxy-3-(1-phenyl-1-(4-chlorophenyl)methoxy)propylthio)ethyl]-1-naphthyloxy}acetic acid methyl ester,
(44) 2-{5-[2-(2RS-hydroxy-3-phenylthiopropylthio) ethyl]-1-naphthyloxy}acetic acid methyl ester,
(45) 2-[5-(2RS-hydroxy-3-diphenylmethoxypropylthio)methyl-1-naphthyloxy] acetic acid methyl ester,
(46) 2-{5-[2RS-hydroxy-3-(1-phenyl-1-(4-chlorophenyl)methoxy)propylthio]methyl-1-naphthyloxy}acetic acid methyl ester,
(47) 2-{5-[2-(2RS-hydroxy-3-phenoxypropylthio) ethyl]-1-naphthyloxy}-acetic acid,
(48) 2-{5-[2-(2RS-hydroxy-3-phenoxypropylsulfinyl) ethyl-1-naphthyloxy}acetic acid,
(49) 2-{5-[2-(2RS-hydroxy-3-phenoxypropylsulfonyl) ethyl]-1-naphthyloxy}acetic acid,
(50) 2-{5-[2-(2R-hydroxy-3-phenoxypropylthio) ethyl]-1-naphthyloxy}acetic acid,
(51) 2-{5-[2-(2S-hydroxy-3-phenoxypropylthio) ethyl]-1-naphthyloxy}acetic acid,
(52) 2-[5-(2RS-hydroxy-3-phenoxypropylthio)methyl-1-naphthyloxy]acetic acid,
(53) 2-[5-(2RS-hydroxy-3-phenoxypropylsulfinyl) methyl-1-naphthyloxy]acetic acid,
(54) 2-[5-(2RS-hydroxy-3-phenoxypropylsulfonyl) methyl-1-naphthyloxy]acetic acid,
(55) 2-{5-[3-(2RS-hydroxy-2-phenylethylthio)propyl]-1-naphthyloxy}acetic acid,
(56) 2-[5-(2RS-hydroxy-3-phenoxypropylthio)-1-naphthyloxy]acetic acid,
(57) 2-[5-(2RS-hydroxy-3-phenoxypropylsulfinyl)-1-naphthyloxy]acetic acid,
(58) 2-[5-(2RS-hydroxy-3-phenoxypropylsulfonyl)-1-naphthyloxy]acetic acid,
(59) 2-[5-(3-styrylsulfinylpropyl)-1-naphthyloxy] acetic acid,
(60) 2-[5-(3-styrylsulfonylpropyl)-1-naphthyloxy] acetic acid,
(61) 2-{5-[2-(2RS-hydroxy-3-(4-chlorophenoxy) propylthio)ethyl]-1-naphthyloxy}acetic acid,
(62) 2-{5-[2-(2RS-hydroxy-3-(4-methylphenoxy) propylthio)ethyl]-1-naphthyloxy}acetic acid,
(63) 2-{5-[2-(2RS-hydroxy-3-(4-methyoxyphenoxy) propylthio)ethyl]-1-naphthyloxy}acetic acid,
(64) 2-{5-[2-(2RS-hydroxy-3-diphenylmethoxypropylthio)ethyl]-1-naphthyloxy}acetic acid,
(65) 2-{5-[2-(2RS-hydroxy-3-phenylthiopropylthio) ethyl]-1-naphthyloxy}acetic acid,
(66) 2-[5-(2RS-hydroxy-3-diphenylmethoxypropylthio)methyl-1-naphthyloxy] acetic acid,
(67) 1-cyanlomethoxy-5-[2-(2RS-hydroxy-3-phenoxypropylthio)ethyl]naphthalene,
(68) 1-cyanomethoxy-5-{2-[2RS-hydroxy-3-(4-chlorophenoxy)propylthio]ethyl}naphthalene,
(69) 1-cyanomethoxy-5-{2-[2RS-hydroxy-3-(4-methylphenoxy)propylthio]ethyl}naphthalene,
(70) 1-cyanomethoxy-5-{2-[2RS-hydroxy-3-(4-methoxyphenoxy)propylthio]ethyl}naphthalene,
(71) 1-cyanomethoxy-5-[2-(2RS-hydroxy-3-diphenylmethoxypropylthio)ethyl]naphthalene,
(72) 1-cyanomethoxy-5-[2-(2RS-hydroxy-3-phenylthiopropylthio)ethyl]naphthalene,
(73) 1-cyanomethoxy-5-(2RS-hydroxy-3-diphenylmethoxypropylthiomethyl)naphthalene,
(74) 2-{5-[2-(2RS -hydroxy-3-(1-phenyl-1-(4-chlorophenyl)methoxy)propylthio)ethyl]-1-naphthyloxy}ethanol,
(75) 2-{5-[2-(2RS-hydroxy-3-phenylaminopropylthio) ethyl]-1-naphthyloxy}ethanol,
(76) 1-(tetrazol-5-ylmethoxy)-5-{2-{2RS-hydroxy-3-(4-methyoxyphenoxy)propylthio]ethyl}naphthalene,
(77) N-methyl-{5-[2RS-hydroxy-3-(1-phenyl-1-(4-chlorophenyl)methoxy)propylthio]methyl-1-naphthyloxy}acetic acid amide,
(78) 1-{2-[5-hydroxy-1-(1,2,3,4-tetrahydronaphthyl)] ethylthio}-3-phenoxy-2RS-propanol,
(79) 2-{5-[2-(2RS-hydroxy-3-phenoxypropylthio) ethyl]-1-(5,6,7,8-tetrahydronaphthyloxy)}acetic acid methyl ester,
(80) 2-{5-[2-(2RS-hydroxy-3-phenoxypropylthio) ethyl]-1-(5,6,7,8-tetrahydronaphthyloxy)}acetic acid or
(81) 1-cyanomethoxy-5-[2-(2RS-hydroxy-3-phenoxypropylthio)ethyl]-5,6,7,8-tetrahydronaphthalene, 10) a compound described in 7), which is
(1) 1-[2-(5-hydroxy-1-naphthyl)ethoxy]-3-phenoxy-2RS-propanol,
(2) 2-{5-[2-(2RS-hydroxy-3-phenoxypropoxy)ethyl]-1-naphthyloxy}acetic acid methyl ester or
(3) 2-{5-[2-(2RS-hydroxy-3-phenoxypropoxy)ethyl]-1-naphthyloxy}acetic acid, 11) a compound described in 8), which is
(1) 1-[2-(5-hydroxy-1-naphthyl)ethylamino]-3-phenoxy-2RS-propanol or
(2) 2-{5-[2-(2RS-hydroxy-3-pheoxypropylamino) ethyl]-1-naphthyloxy}acetic acid, 12) a pharmaceutical composition which comprises a naphthyloxyacetic acid derivative of the formula (I) depicted in 1), non-toxic salt thereof, non-toxic acid addition salt thereof or their hydrate as an active ingredient, and 13) a pharmaceutical composition (PGE$_2$ antagonist or agonist) which comprises a naphthyloxyacetic acid derivative of the formula (I) depicted in 1), non-toxic salt thereof, non-toxic acid addition salt thereof or their hydrate as an active ingredient.

DETAILED DESCRIPTION OF THE INVENTION

In the formula (I), C1–4 alkyl represented by $R^1$, $R^2$, $R^3$ and $R^4$, or C1–4 alkyl represented as substituent of phenyl in M means methyl, ethyl, propyl, butyl and isomeric groups thereof.

In the formula (I), C1–4 alkylene in A means methylene, ethylene, trimethylene, tetramethylene and isomeric groups thereof.

In the formula (I), C1–6 alkylene represented by E and L means methylene, ethylene, trimethylene, tetramethylene, pentamethylene, hexamethylene and isomeric groups thereof.

In the formula (I), 1–4 alkoxy in M means methoxy, ethoxy, propoxy, butoxy and isomeric groups thereof.

In the formula (I), halogen in M means chlorine, bromine, fluorine and iodine.

In the formula (I), the side chain represented by —O—A may be connected with any carbon atom at 1st to 4th position, preferably, at 1st position.

In the formula (I), the side chain represented by —E—G—L—M may be connected with any carbon atom at 5th to 8th position, preferably, at 5th or 6th position.

Unless otherwise, specified all isomers are included in the invention. For example, alkyl, alkylene and alkenylene includes straight-chain or branched-chain ones. Double bond in alkenylene include structure of configurations E, Z and EZ mixtures. Isomers generated by asymmetric carbon (s) e.g. branched alkyl are also included in the present invention. In addition, isomers generated by sulfinyl are also included in the present invention.

Salts

The compounds of the present invention of the formula (I) may be converted into the corresponding salts by known methods per se. Non-toxic and water-soluble salts are preferable. Suitable salts, for example, are follows. salts of alkaline metals (potassium, sodium etc.), salts of alkaline earth metals (calcium, magnesium etc.), ammonium salts, salts of pharmaceutically acceptable organic amines (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine etc.).

Acid Addition Salts

The compounds of the formula (I) may be converted into the corresponding acid additional salts by methods known per se. Non-toxic and water-soluble acid addition salts are preferable. Suitable acid addition salts, for example, are salts of inorganic acids, e.g., hydrochloride, hydrobromide, hydroiodide, sulphate, phosphate, nitrate etc., or salts of organic acids, e.g., acetate, trifluoroactate, lactate, tartarate, oxalate, fumarate, maleate, citrate, benzoate, methanesulphonate, ethanesulphonate, benzenesulphonate, toluenesulphonate, isethioate, glucuronate, gluconate etc.

Preferable Compound

In the compounds of the formula (I) of the present invention, the compounds wherein L is —(CH$_2$)$_m$—CH=CH—(CH$_2$)$_n$— in which m and n are the same meaning as hereinbefore defined, or —(CH$_2$)$_x$—CH(OH)—(CH$_2$)$_y$— in which x and y are the same meaning as hereinbefore defined, are preferable. The compounds wherein L is —CH=CH— or —CH$_2$—CH(OH)—CH$_2$—, are more preferable.

Concretely, the following compounds are preferable.

The compounds of the formula (IA)

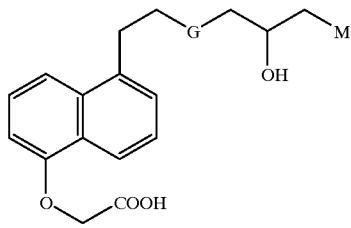

(IA)

The compounds of the formula (IB)

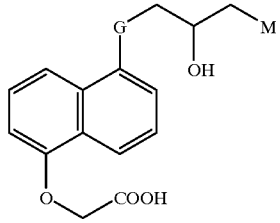

(IB)

The compounds of the formula (IC)

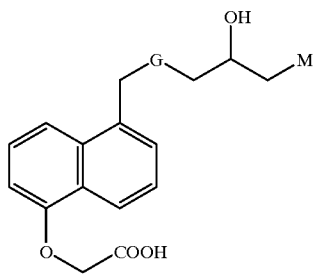

(IC)

The compounds of the formula (ID)

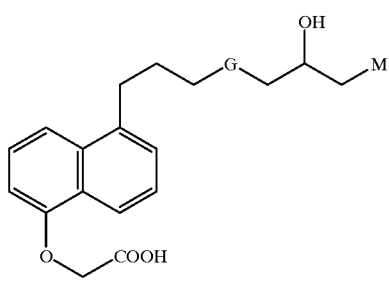

(ID)

The compounds of the formula (IE)

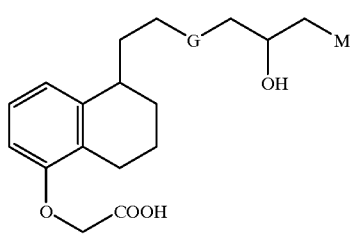

(IE)

The compounds of the formula (IF)

(IF)

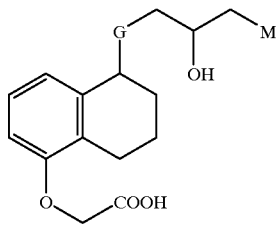

The compounds of the formula (IG)

(IG)

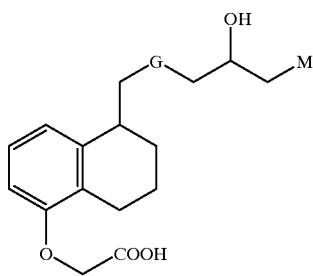

The compounds of the formula (IH)

(IH)

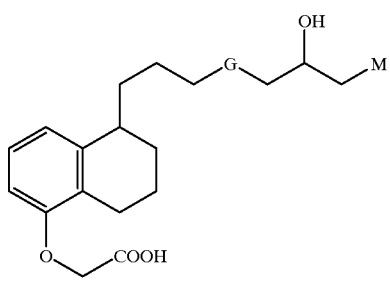

The compounds of the formula (IJ)

(IJ)

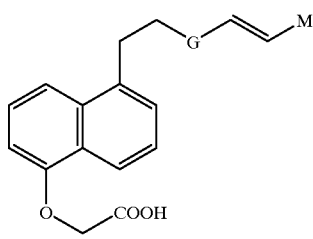

The compounds of the formula (IK)

(IK)

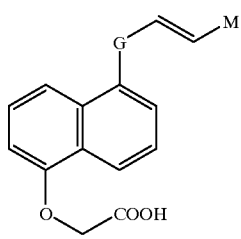

The compounds of the formula (IL)

(IL)

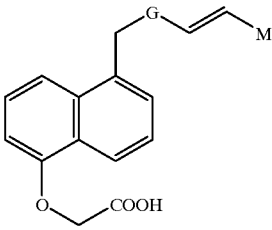

The compounds of the formula (IM)

(IM)

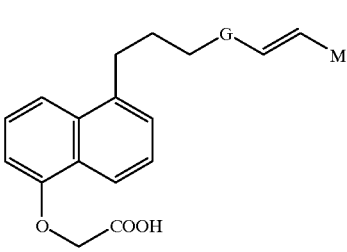

The compounds of the formula (IN)

(IN)

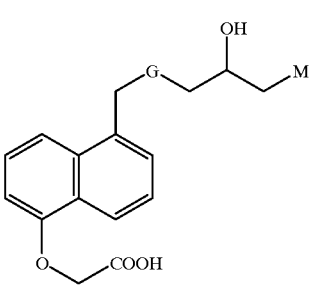

The compounds of the formula (IO)

(IO)

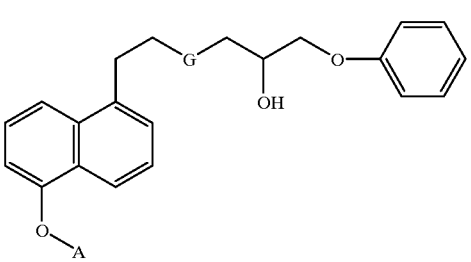

In the formula (IA), (IB), (IC), (ID), (IE), (IF), (IG), (IH), (IJ), (IK), (IL), (IM), (IN) and (IO), all symbols are the same meaning as hereinbefore defined.

The compounds described in Example and the following compounds are preferable particularly.

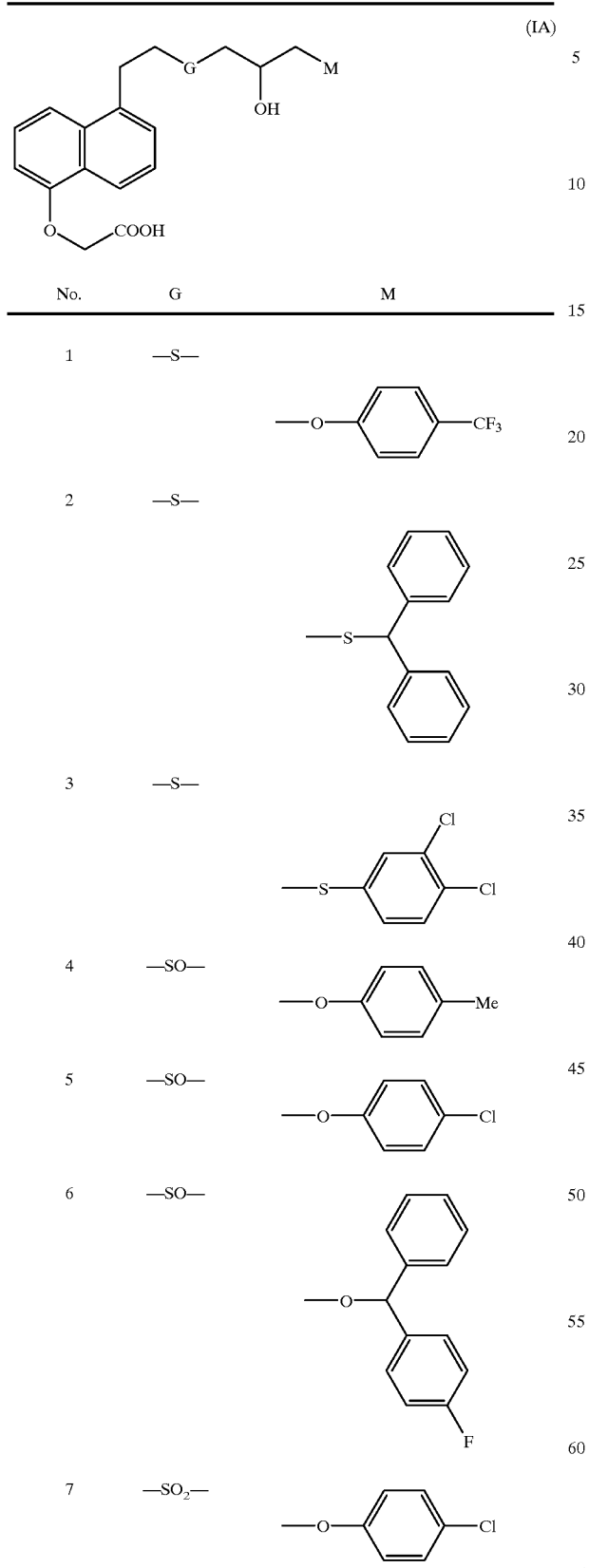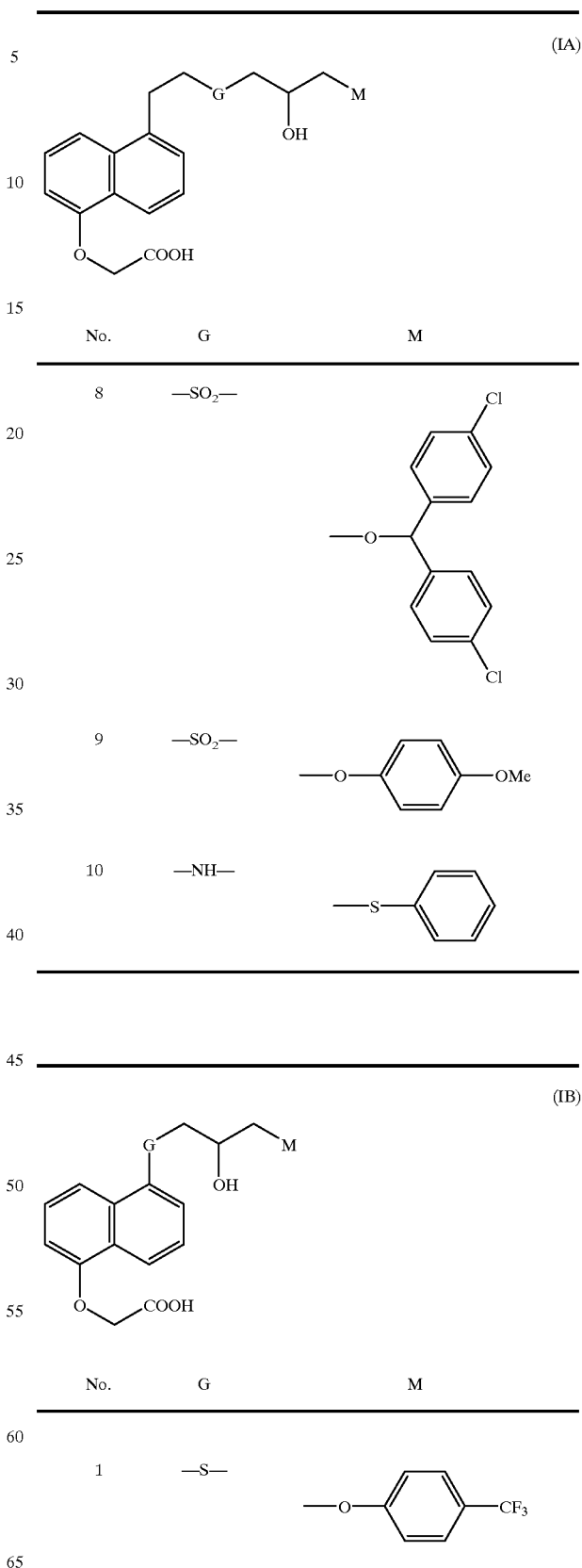

-continued
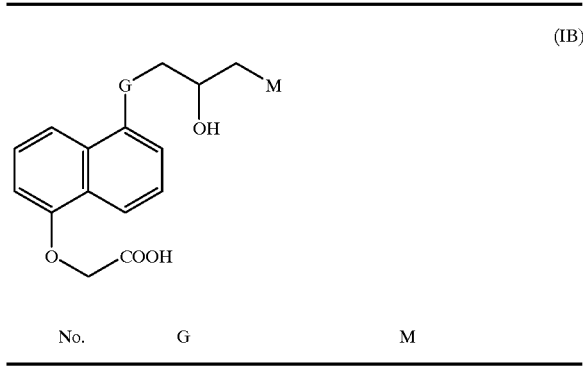
(IB)
| No. | G | M |
|---|---|---|
| 2 | —S— | 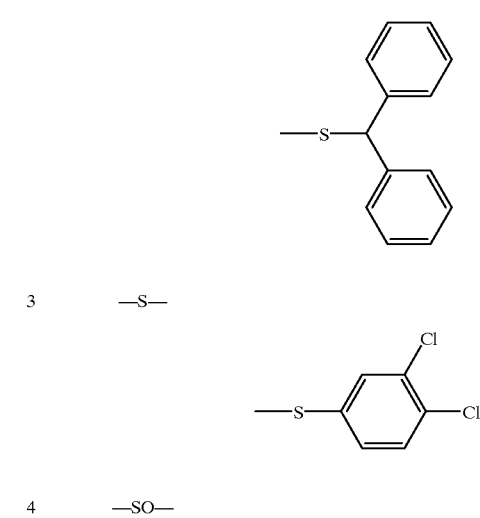 |
| 3 | —S— | |
| 4 | —SO— | |
| 5 | —SO— | |
| 6 | —SO— | 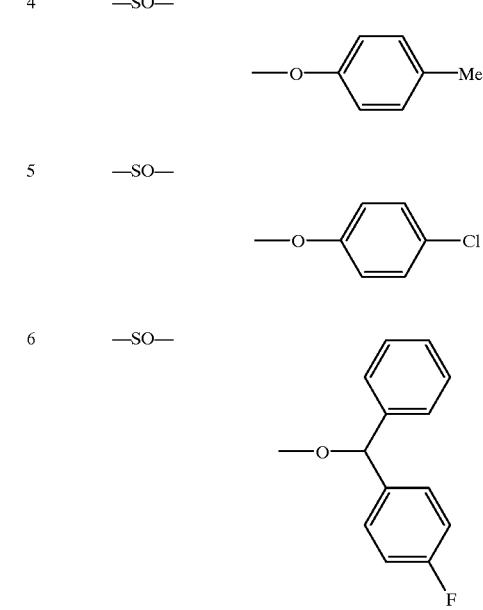 |
| 7 | —SO$_2$— | 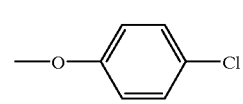 |
-continued
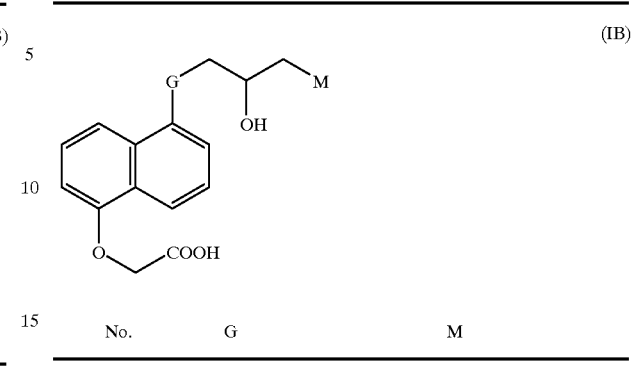
(IB)
| No. | G | M |
|---|---|---|
| 8 | —SO$_2$— | 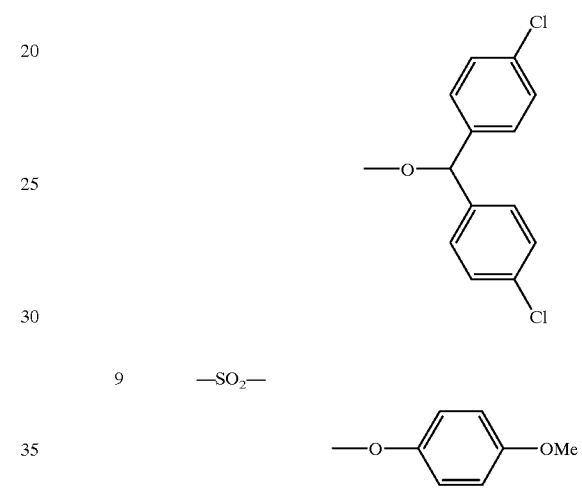 |
| 9 | —SO$_2$— | |
| 10 | —NH— | |
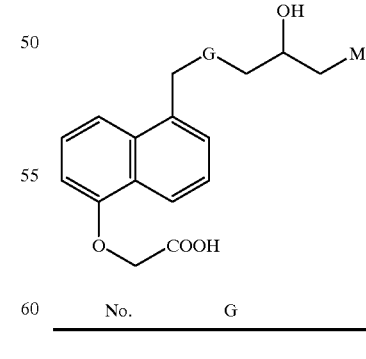
(IC)
| No. | G | M |
|---|---|---|
| 1 | —S— | |

-continued
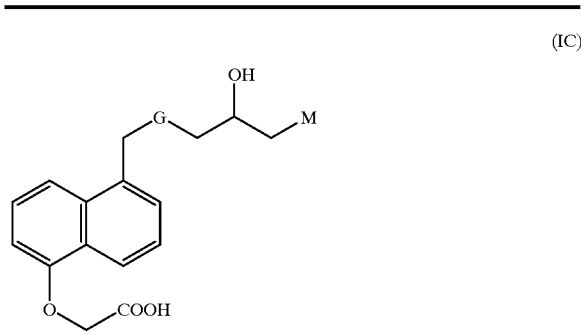
(IC)
| No. | G | M |
|---|---|---|
| 2 | —S— | —S–CH(C6H5)2 (methylthio-diphenylmethane) |
| 3 | —S— | —S–(3,4-dichlorophenyl) |
| 4 | —SO— | —O–(4-methylphenyl) |
| 5 | —SO— | —O–(4-chlorophenyl) |
| 6 | —SO— | —O–CH(phenyl)(4-fluorophenyl) |
| 7 | —SO2— | —O–(4-chlorophenyl) |
-continued
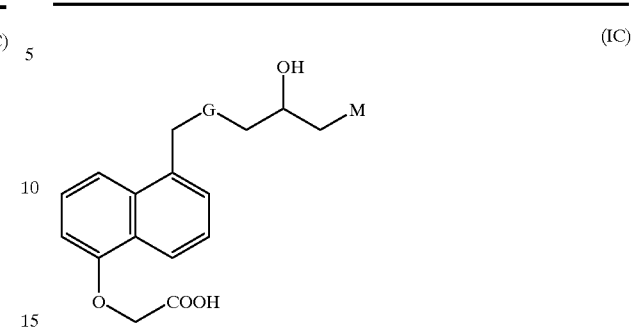
(IC)
| No. | G | M |
|---|---|---|
| 8 | —SO2— | —O–CH(4-chlorophenyl)2 |
| 9 | —SO2— | —O–(4-methoxyphenyl) |
| 10 | —NH— | —S–phenyl |
(ID)
| No. | G | M |
|---|---|---|
| 1 | —S— | —O–(4-CF3-phenyl) |

-continued
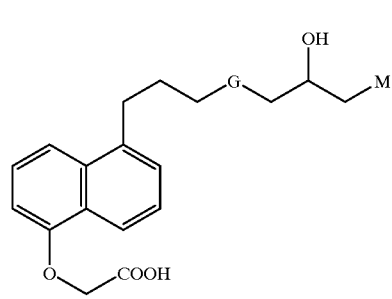
(ID)
| No. | G | M |
|---|---|---|
| 2 | —S— | 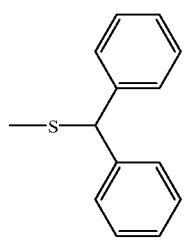 |
| 3 | —S— | 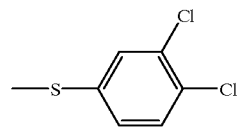 |
| 4 | —SO— | 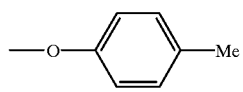 |
| 5 | —SO— | 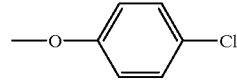 |
| 6 | —SO— | 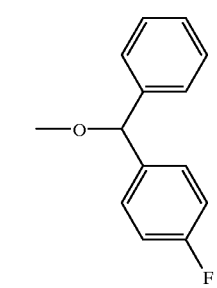 |
| 7 | —SO₂— | 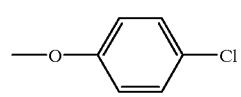 |
-continued
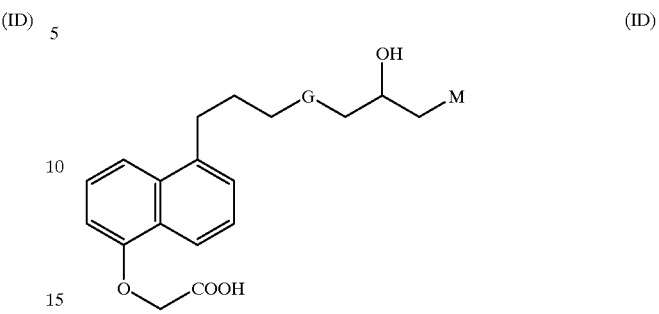
(ID)
| No. | G | M |
|---|---|---|
| 8 | —SO₂— | 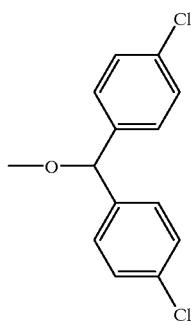 |
| 9 | —SO₂— | 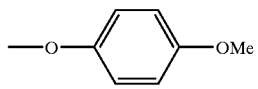 |
| 10 | —NH— | 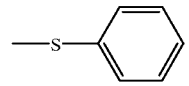 |
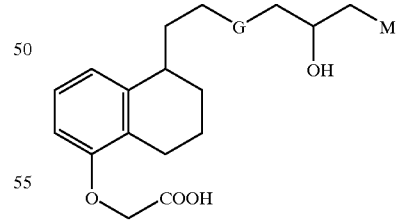
(IE)
| No. | G | M |
|---|---|---|
| 1 | —S— | 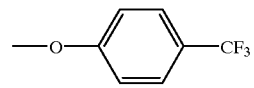 |

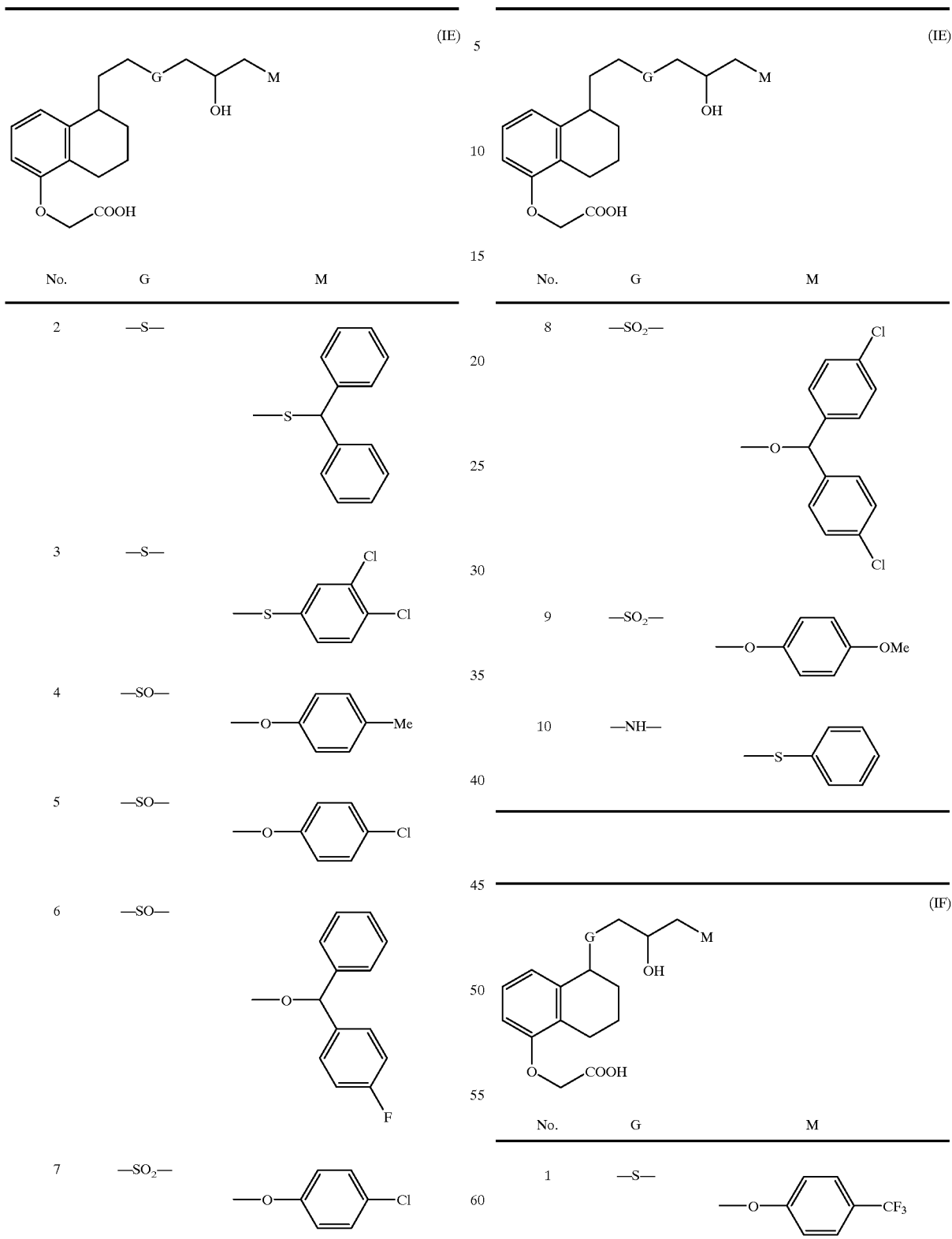

-continued
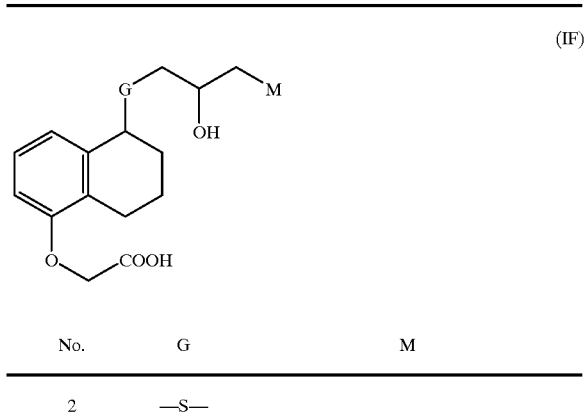
(IF)
| No. | G | M |
|---|---|---|
| 2 | —S— | 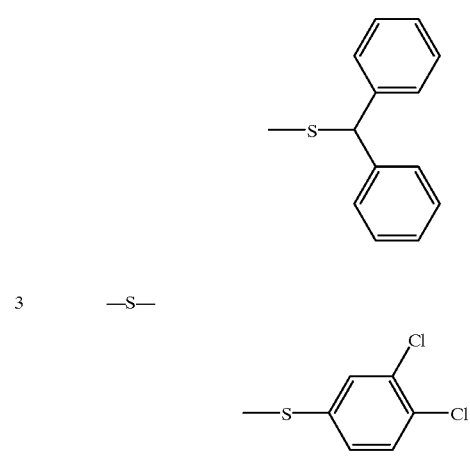 |
| 3 | —S— | 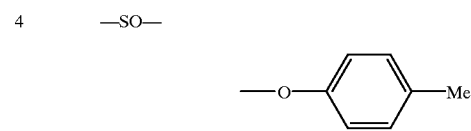 |
| 4 | —SO— | 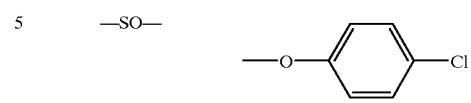 |
| 5 | —SO— | |
| 6 | —SO— | 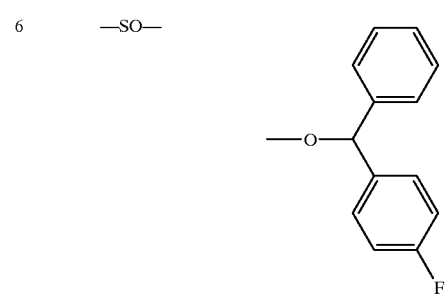 |
| 7 | —SO₂— | 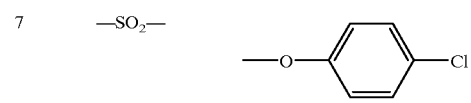 |
-continued
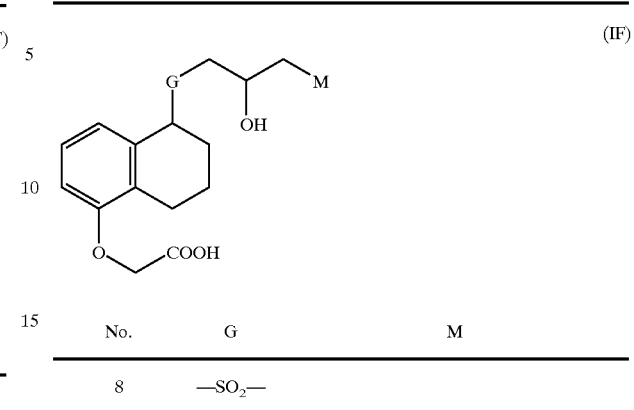
(IF)
| No. | G | M |
|---|---|---|
| 8 | —SO₂— | 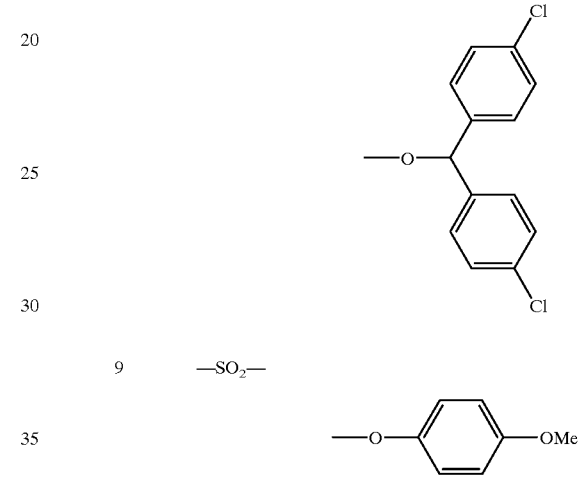 |
| 9 | —SO₂— | |
| 10 | —NH— | |
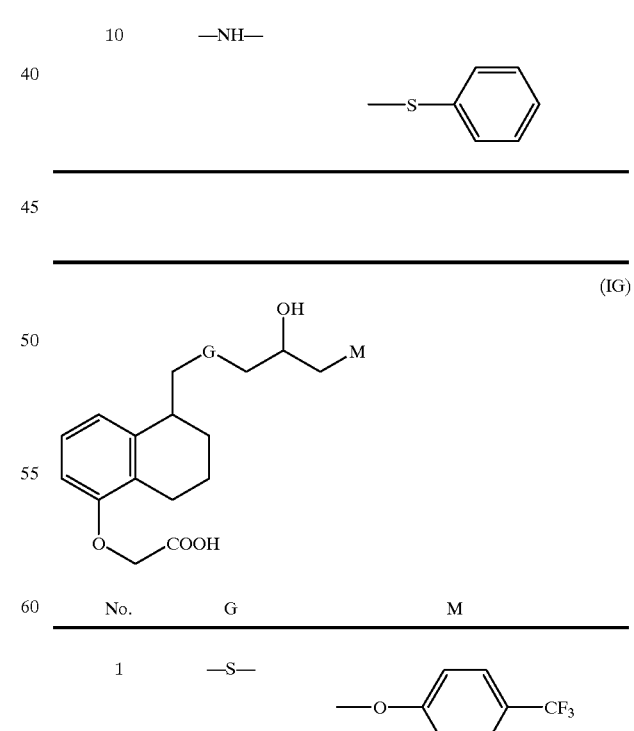
(IG)
| No. | G | M |
|---|---|---|
| 1 | —S— | |

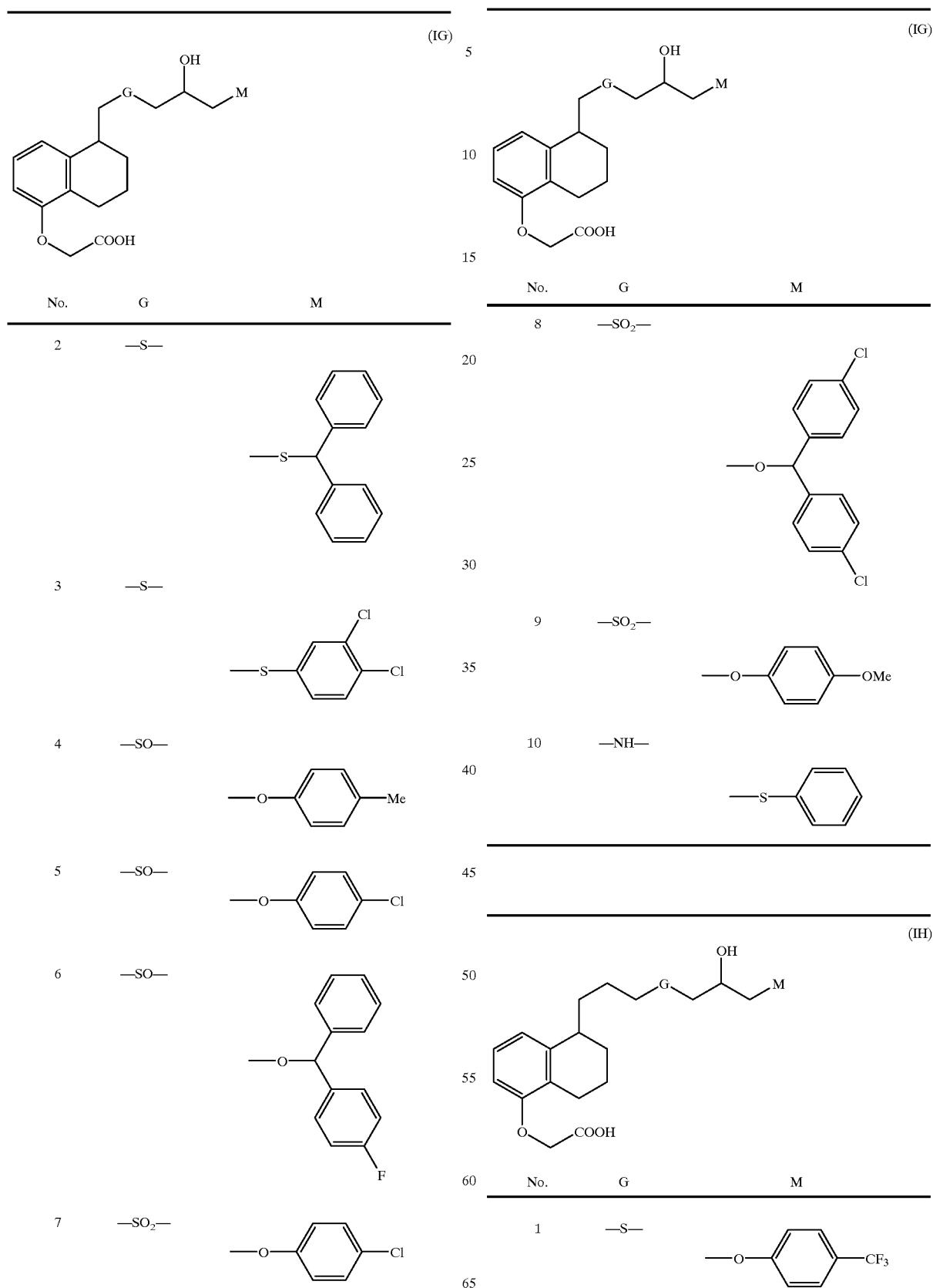

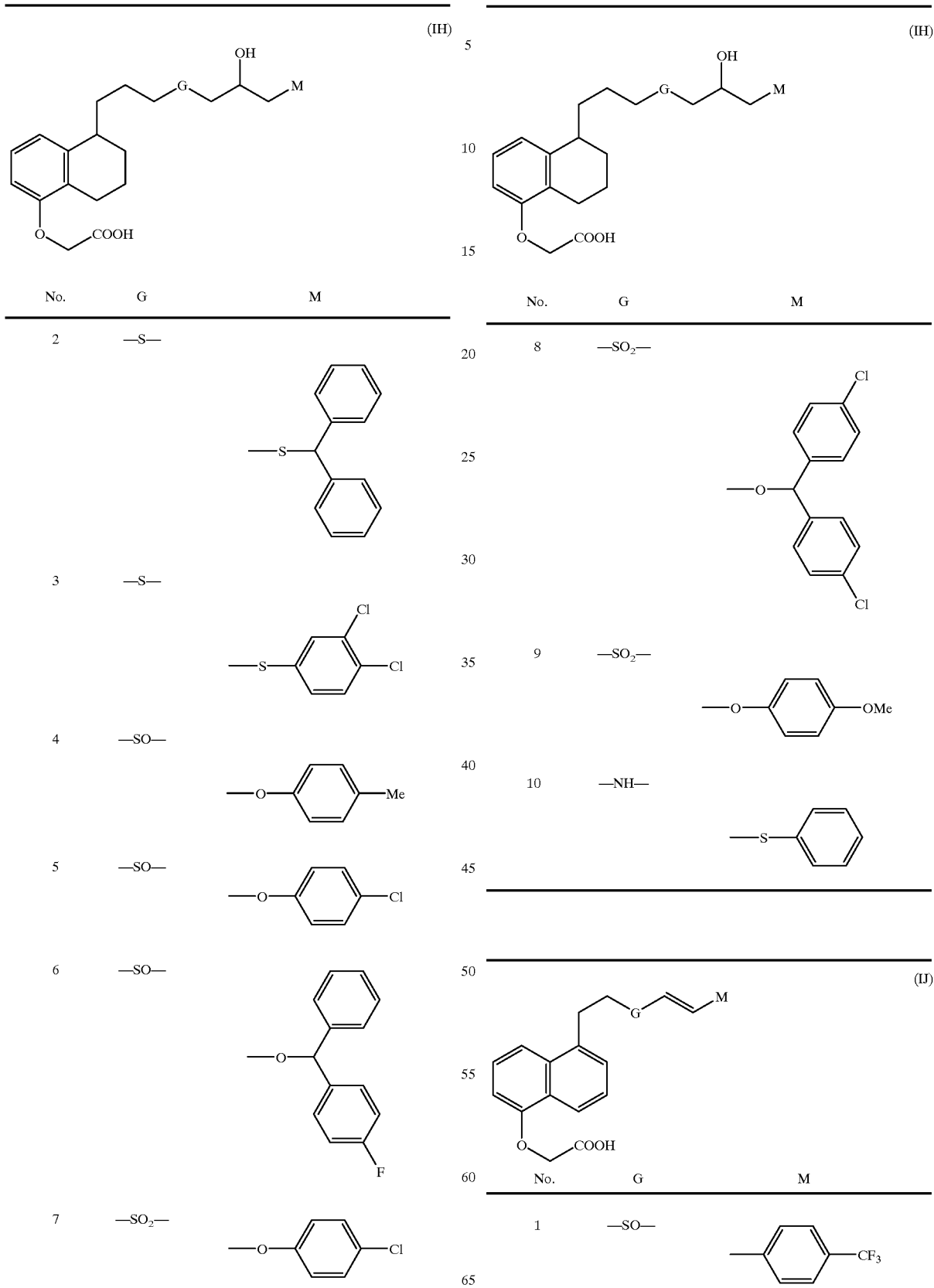

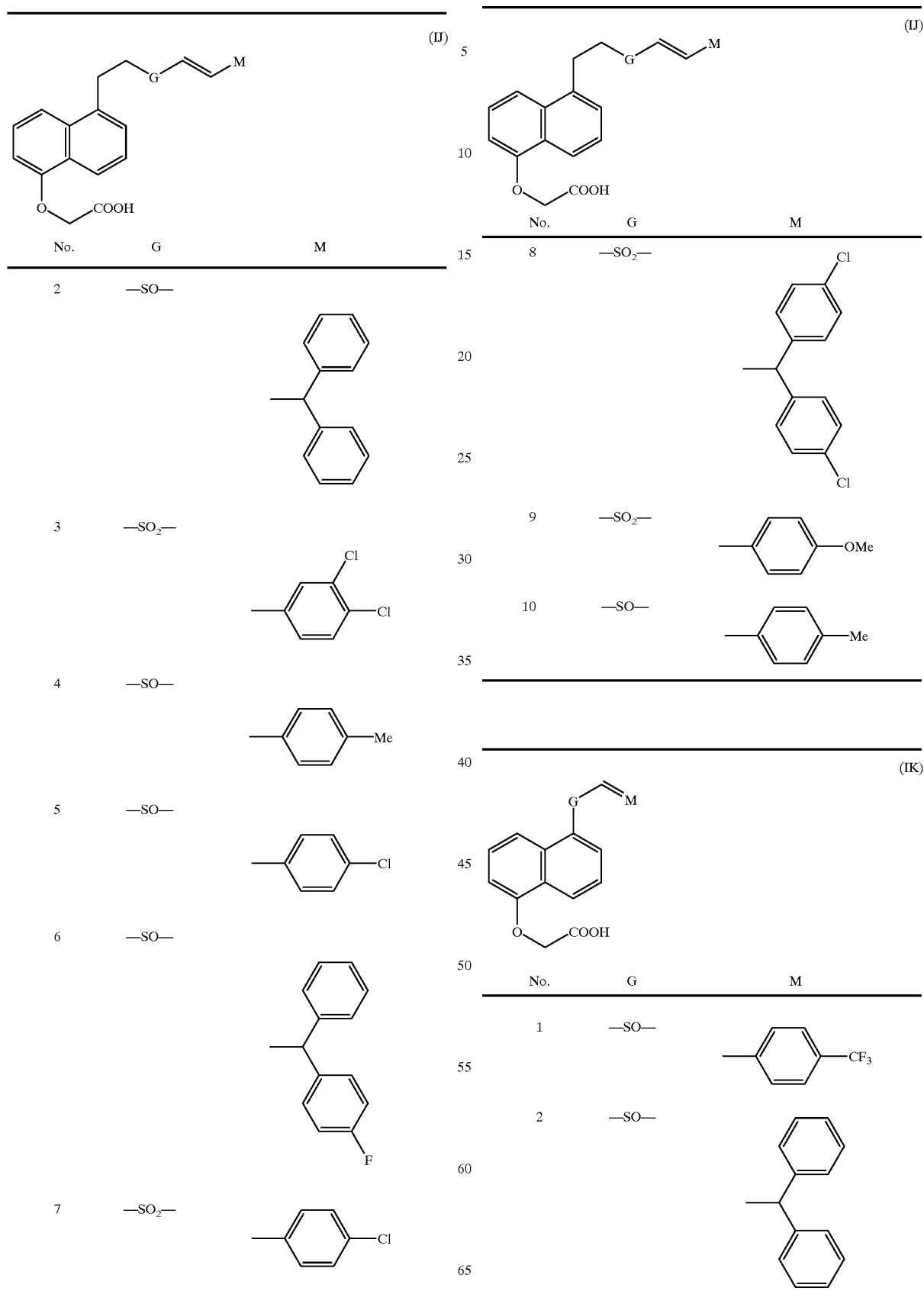

-continued (IK)

[Structure: naphthalene with G=M substituent at position 5 and OCH2COOH at position 1]

| No. | G | M |
|---|---|---|
| 3 | —SO2— | 3,4-dichlorophenyl |
| 4 | —SO— | 4-methylphenyl |
| 5 | —SO— | 4-chlorophenyl |
| 6 | —SO— | 1-(4-fluorophenyl)-1-phenylethyl |
| 7 | —SO2— | 4-chlorophenyl |
| 8 | —SO2— | bis(4-chlorophenyl)ethyl |

-continued (IK)

[Structure: naphthalene with G=M substituent at position 5 and OCH2COOH at position 1]

| No. | G | M |
|---|---|---|
| 9 | —SO2— | 4-methoxyphenyl |
| 10 | —SO— | 4-methylphenyl |

(IL)

[Structure: naphthalene with CH2-G-CH=CH-M substituent at position 5 and OCH2COOH at position 1]

| No. | G | M |
|---|---|---|
| 1 | —SO— | 4-(trifluoromethyl)phenyl |
| 2 | —SO— | 1,1-diphenylethyl |
| 3 | —SO2— | 3,4-dichlorophenyl |
| 4 | —SO— | 4-methylphenyl |

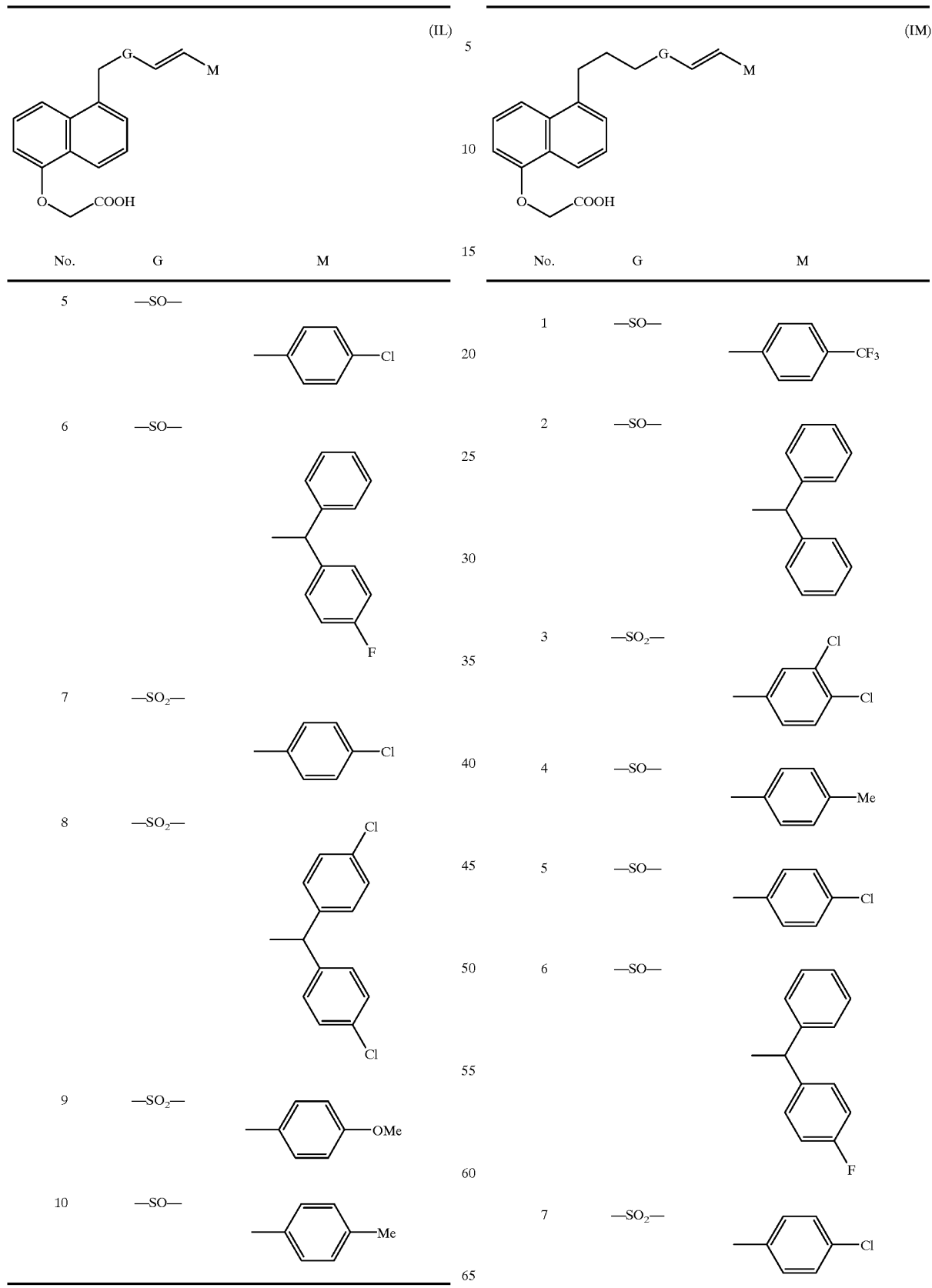

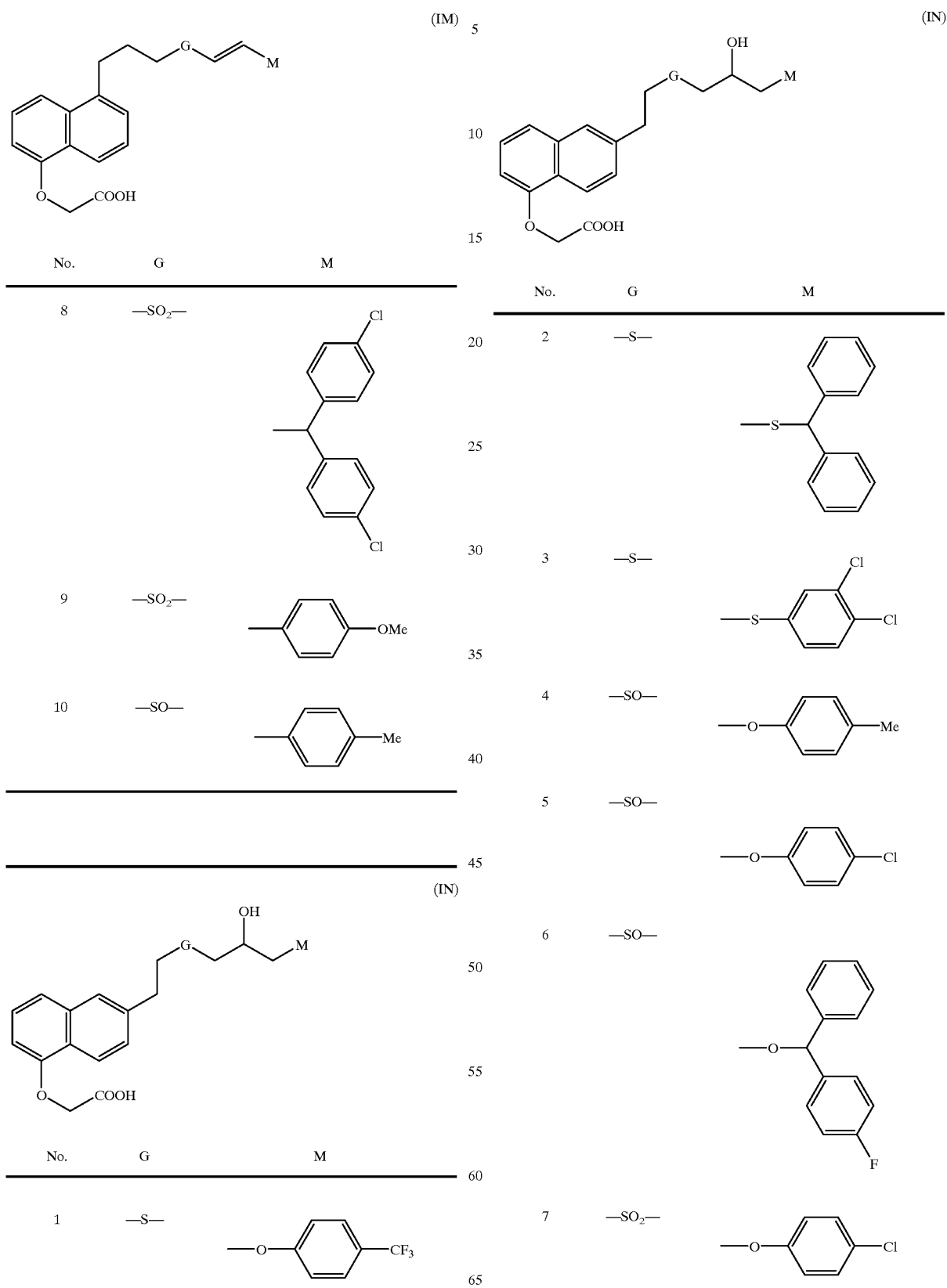

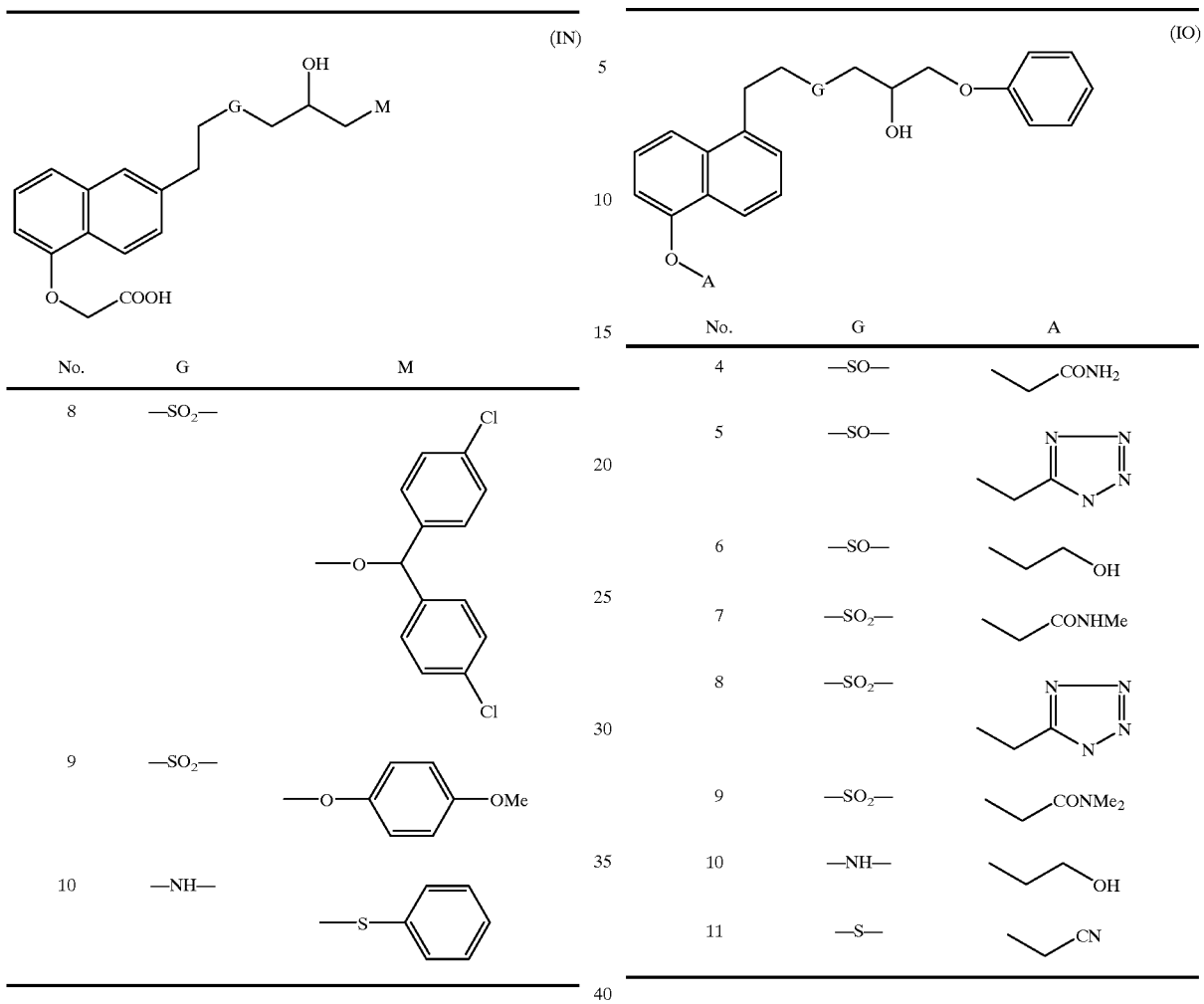

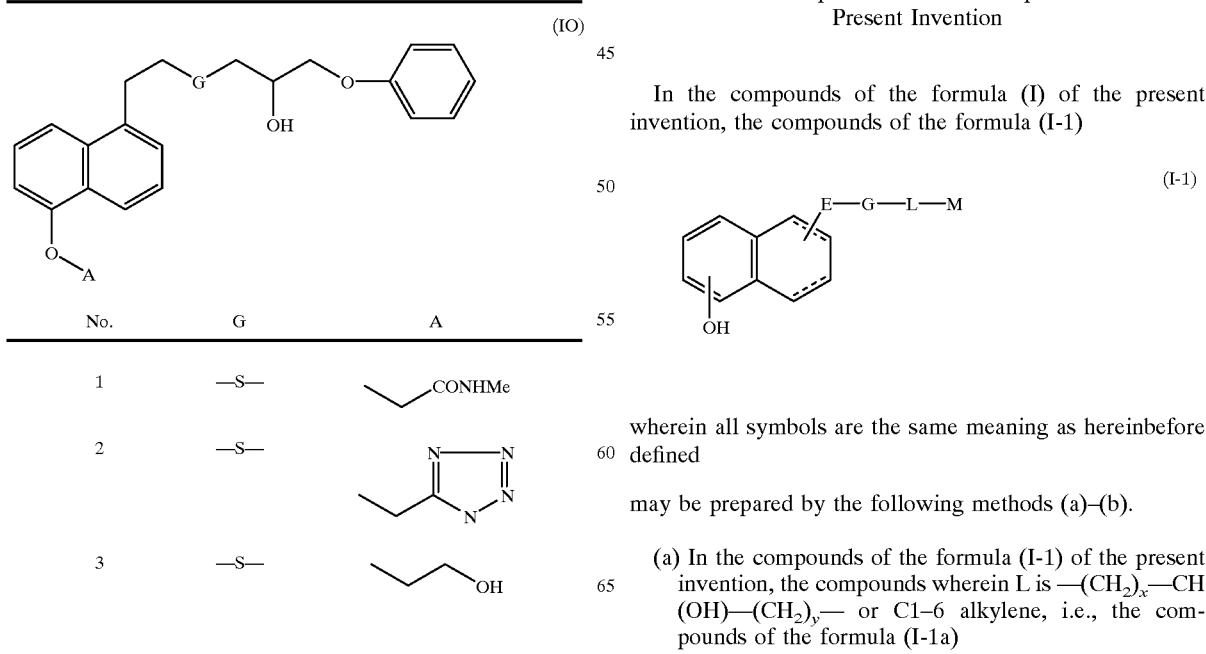

Method of Preparation for the Compounds of the Present Invention

In the compounds of the formula (I) of the present invention, the compounds of the formula (I-1)

wherein all symbols are the same meaning as hereinbefore defined may be prepared by the following methods (a)–(b).

(a) In the compounds of the formula (I-1) of the present invention, the compounds wherein L is $-(CH_2)_x-CH(OH)-(CH_2)_y-$ or C1–6 alkylene, i.e., the compounds of the formula (I-1a)

(I-1a)

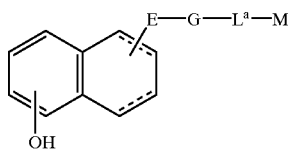

wherein $L^a$ is —$(CH_2)_x$—$CH(OH)$—$(CH_2)_y$— or C1–6 alkylene, and the other symbols are the same meaning as hereinbefore defined
may be prepared from the compounds of the formula (II-a)

(II-a)

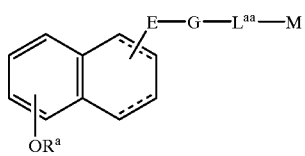

wherein $L^{aa}$ is —$(CH_2)_x$—$CH(OR^{aa})$—$(CH_2)_y$— in which, $R^{aa}$ is the protecting group which may be removed in an acidic condition, for example, tetrahydropyranyl etc., or C1–6 alkylene, $R^a$ is the protecting group which may be removed in an acidic condition or an alkaline condition, for example, methoxymethyl or ethylcarbonate etc., and the other symbols are the same meaning as hereinbefore defined, with the proviso that when nitrogen atom in G or M in the formula (I-1a) is free —NH group, NH group in the formula (II-a) is protected by the well-known protecting group (for example, benzyloxycarbonyl (cbz), t-butoxycarbonyl (boc) or trifluoroacetyl ($COCF_3$)etc.)
by removal of hydroxy-protecting group in an acidic condition, or removal of hydroxy-protecting group in an acidic condition and an alkaline condition two times, succeedingly, (Which reaction may be started first.), if necessary, followed by removal of NH-protecting group.

This reaction may be carried out by known methods. For example, the removal of hydroxy-protecting group in an acidic condition may be carried out in a water-miscible organic solvent (methanol, ethanol, tetrahydrofuran (THF) etc.), by using organic acid (acetic acid, p-toluene sulfonic acid, trifluoro acetic acid or trichloro acetic acid etc.) or inorganic acid (hydrochloric acid or hydrobromic acid etc.), at 0–90° C. The removal of hydroxy-protecting group in an alkaline condition may be carried out in an organic solvent (methanol, ethanol, dimethoxyethane or mixture thereof etc.), using an aqueous solution of hydroxide of alkali (sodium hydroxide, potassium hydroxide etc.), hydroxide of alkaline-earth metals (calcium dihydroxide etc.) or carbonate (potassium carbonate etc.) at 0–50° C.

As for removal of NH-protecting group, for example, the removal of cbz group may be carried out under an atmosphere of hydrogen gas, in an organic solvent (methanol, ethanol or THF etc.), by using catalyst (Pd—C, Pd or Ni etc.), at 0–50° C. The removal of boc may be carried out in a water-miscible organic solvent (methanol, ethanol or THF etc.), by using organic acid (acetic acid, p-toluene sulfonic acid, trifluoro acetic acid or trichloro acetic acid etc.) or inorganic acid (hydrochloric acid or hydrobromic acid etc.), at 0–90° C. The removal of $COCF_3$ may be carried out, for example, in a water-miscible organic solvent (methanol, ethanol, THF, dimethoxyethane or mixture thereof etc.), using an aqueous solution of hydroxide of alkali (sodium hydroxide, potassium hydroxide etc.), hydroxide of alkaline-earth metals (calcium dihydroxide etc.) or carbonate (potassium carbonate etc.) at 0–50° C.

(b) In the present invention compounds of the formula (I-1), the compounds wherein L is —$(CH_2)_m$—$CH=CH$—$(CH_2)_n$—, i.e., the compounds of the formula (I-1b)

(I-1b)

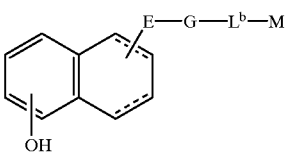

wherein $L^b$ is —$(CH_2)_m$—$CH=CH$—$(CH_2)_n$—, and the other symbols are the same meaning as hereinbefore defined
may be prepared from the compounds of the formula (II-b)

(II-b)

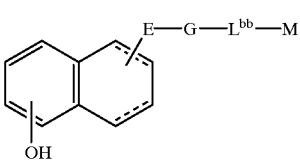

wherein $L^{bb}$ is —$(CH_2)_m$—$CH_2CH(OR^b)$—$(CH_2)_n$— in which, $R^b$ is the well-known elimination group (for example, mesyl or tosyl group etc.), and the other symbols are the same meaning as hereinbefore defined, with the proviso that when nitrogen atom in G or M in the formula (I-1b) is free —NH group, NH group in the formula (II-b) is protected by the well-known protecting group (for example, cbz, boc or $COCF_3$ etc.)
by removal of elimination group, if necessary, followed by removal of NH-protecting group.

This reaction may be carried out in an organic solvent (methanol or ethanol etc.) by adding base (potassium hydroxide, sodium hydroxide or triethylamine etc.) at 0–100° C. The removal of NH-protecting group may be carried out by the method described hereinbefore.

In the compound of the formula (I) of the present invention, the compounds of the formula (I-2) of the present invention (I-2)

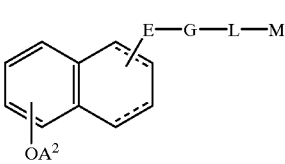

wherein $A^2$ is the same meaning as A other than hydrogen
may be prepared by reacting the compounds, in which nitrogen atom in G or M in the formula (I-1) is free —NH group, NH group is protected by the well-known protecting group (for example, cbz, boc or $COCF_3$ etc.), i.e. the compounds of the formula (II-c)

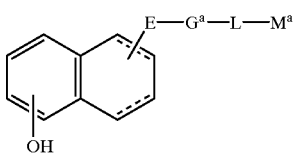
(II-c)

wherein $G^a$ and $M^a$ are the same meaning as G and M, respectively, with the proviso that when nitrogen atom in G or M in the formula (I-2) is free —NH group, NH group is protected by the well-known protecting group (for example, cbz, boc or $COCF_3$ etc.) and the other symbols are the same meaning as hereinbefore defined
with the compounds of the formula (III)

(III)

wherein $X^2$ is halogen and $A^{2a}$ is
(i) —(C1–4 alkylene)—$COOR^{1a}$ in which $R^{1a}$ is C1–4 alkyl,
(ii) —(C1–4 alkylene)—$OR^5$, in which $R^5$ is tetrahydropyranyl,
(iii) —(C1–4 alkylene)—$CONR^2R^3$,
(iv) —(C1–4 alkylene)-tetrazolyl or
(v) —(C1–4 alkylene)—CN,
and the other symbols are the same meaning as hereinbefore defined, with the proviso that when nitrogen atom in $A^{2a}$ is free —NH group, NH group is protected by the well-known protecting group (for example, cbz, boc or $COCF_3$ etc.), if necessary, followed by hydrolysis in an alkaline condition or by removal of protecting group.

The above mentioned O-alkylation is known, and for example, this reaction may be carried out in a water-miscible organic solvent (acetone, THF or methylene chloride etc.) in the presence of a base (potassium carbonate etc.), at 0–50° C.

The hydrolysis in an alkaline condition is well known. For example, this reaction may be carried out in a water-miscible organic solvent (methanol, ethanol, dimethoxyethane or mixture thereof etc.), using an aqueous solution of hydroxide of alkali (sodium hydroxide, potassium hydroxide etc.), hydroxide of alkaline-earth metals (calcium dihydroxide etc.) or carbonate (potassium carbonate etc.) at 0–50° C. The removal of protecting group may be carried out by the method described hereinbefore.

In the compounds of the formula (I) of the present invention, the compounds wherein A is —(C1–4 alkylene)-tetrazol-5-yl, i.e. the compounds of the formula (I-3)

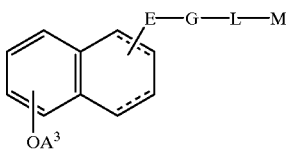
(I-3)

in which, $A^3$ is —(C1–4 alkylene)-tetrazol-5-yl and the other symbols are the same meaning as hereinbefore defined may be also prepared by reacting the compounds of the formula (I-4)

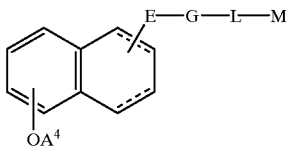
(I-4)

in which $A^4$ is —(C1–4 alkylene)—CN and the other symbols are the same meaning as hereinbefore defined with the azide.

The reaction to introduce a tetrazol-5-yl group from cyano group with an azide are known, it may be carried out, for example, on anhydrous condition, using with azide (sodium azide, lithium azide, potassium azide etc.) in the presence of weak acid (pyridium chloride, ammonium chloride, dimethylaniline hydrochloride etc.) in an inert organic solvent (DMF, N-methylpyrrolidone etc.) with heating.

In the compounds of the formula (I) of the present invention, the compounds wherein A is —(C1–4 alkylene)—$CONR^2R^3$, i.e. the compounds of the formula (I-5)

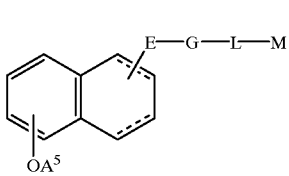
(I-5)

in which, $A^5$ is —(C1–4 alkylene)—$CONR^2R^3$ in which $R^2$ and $R^3$ are the same meaning as hereinbefore defined and the other symbols are the same meaning as hereinbefore defined may be also prepared by reacting the compounds of the formula (I-6)

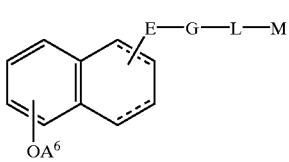
(I-6)

in which $A^6$ is —(C1–4 alkylene)—$COOR^{1a}$ in which $R^{1a}$ is the same meaning as hereinbefore defined and the other symbols are the same meaning as hereinbefore defined with the compounds of the formula

$HNR^2R^3$ (IX)

in which all symbols are the same meaning as hereinbefore defined.

The above reaction to form an amide bond is well known. For example, this reaction may be carried out in inert organic solvent (benzene, toluene or methylene chloride etc.), or in the absence of solvent, using tertiary amine (pyridine or triethylamine etc.) at 0–50° C., or it may be carried out in an organic solvent (methylene chloride or THF etc.), using a corresponding base, in the presence or absence of corresponding condensing agents (2-chloro-N-methylpyridiunium iodide etc.) at 0–40° C.

The compounds of the formula (II-a) and (II-b) may be prepared by the known reaction. For example, these compounds may be prepared according to the method shown in the reaction scheme (1), (2), (3) or (4) or method described in Example.

In the compounds of the formula (I-1) of the present invention, the compounds wherein G is —NH— and L is —CH$_2$—CH(OH)—(CH$_2$)$_y$—, i.e. the compounds of the formula

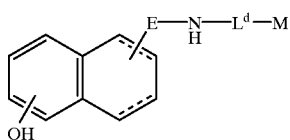

(I-1c)

in which L$^d$ is —CH$_2$—CH(OH)—(CH$_2$)$_y$— in which y is the same meaning as hereinbefore defined and the other symbols are the same meaning as hereinbefore defined
may be also prepared according to the method shown in the reaction scheme (5) or method described in Example.

In the compounds of the formula (I) of the present invention, the compounds wherein M is

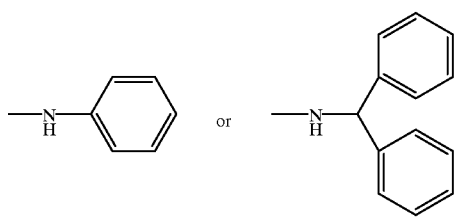

in which each phenyl may be substituted by the substituent described hereinbefore and L is —(CH$_2$)$_x$—CH(OH)—(CH$_2$)$_y$—, i.e. the compounds of the formula

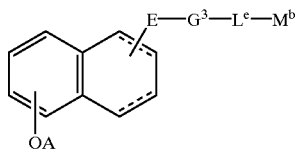

(I-7)

in which M$^b$ is

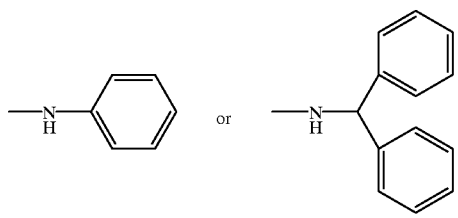

in which each phenyl may be substituted by the substituent described hereinbefore, L$^e$ is —(CH$_2$)$_x$—CH(OH)—(CH$_2$)$_y$— in which x and y are the same meaning as hereinbefore defined, G$^3$ is —S—, —O— or —NR$^4$— and the other symbols are the same meaning as hereinbefore defined
may be also prepared according to the method shown in the reaction scheme (6) or method described in Example.

In reaction scheme (1), (2), (3), (4), (5) and (6) each symbol means the following definition or is the same meaning as defined hereinbefore.

Et is ethyl,

Ac is acetyl, iPr is isopropyl.

Ph is phenyl,

MOM is methoxymethyl,

9-BBN is 9-borabicyclo[3.3.1]nonan,

LAH is lithium aluminum hydride,

TsCl is tosylchloride,

AcSK is potassium thioacetate, mCPBA is methachloroperbenzoic acid, cbz is benzyloxycarbonyl, L$^c$ is L$^{aa}$, L$^{bb}$ or C1–6 alkylene, E$^c$ is C1–6 alkylene, G$^1$ is —O—, —S—, —SO—, or —SO$_2$—, G$^2$ is —NR$^4$—, Bu$_4$NBr is tetrabutylammonium bromide, Py is pyridine, R$^d$ is
1) acetyl or hydrogen when G$^3$ is —S—,
2) hydrogen when G$^3$ is —O— or —NR$^{4a}$— in which R$^{4a}$ is C1–4 alkyl,
3) NH-protecting group as defined hereinbefore when G$^3$ is —NH—Z is NH-protecting group as defined hereinbefore and Ph$^a$ is phenyl may be substituted by 1–3 of C1–4 alkyl, C1–4 alkoxy, halogen, nitro or trifluoromethyl.

The compounds of the formula (II-a) are a part of the compounds of the formula (VII).

The compounds of the formula (II-b) are a part of the compounds of the formula (VIII). The compounds of the formula (IV), (V—O) or (VI) as starting materials may be prepared by the known methods. For example, these compound may be prepared by the methods described in Example in the present specification.

In each reaction in the present specification, obtained products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

The other starting materials and reagents in the present invention are known per se or may be prepared by known methods.

Reaction Scheme 1
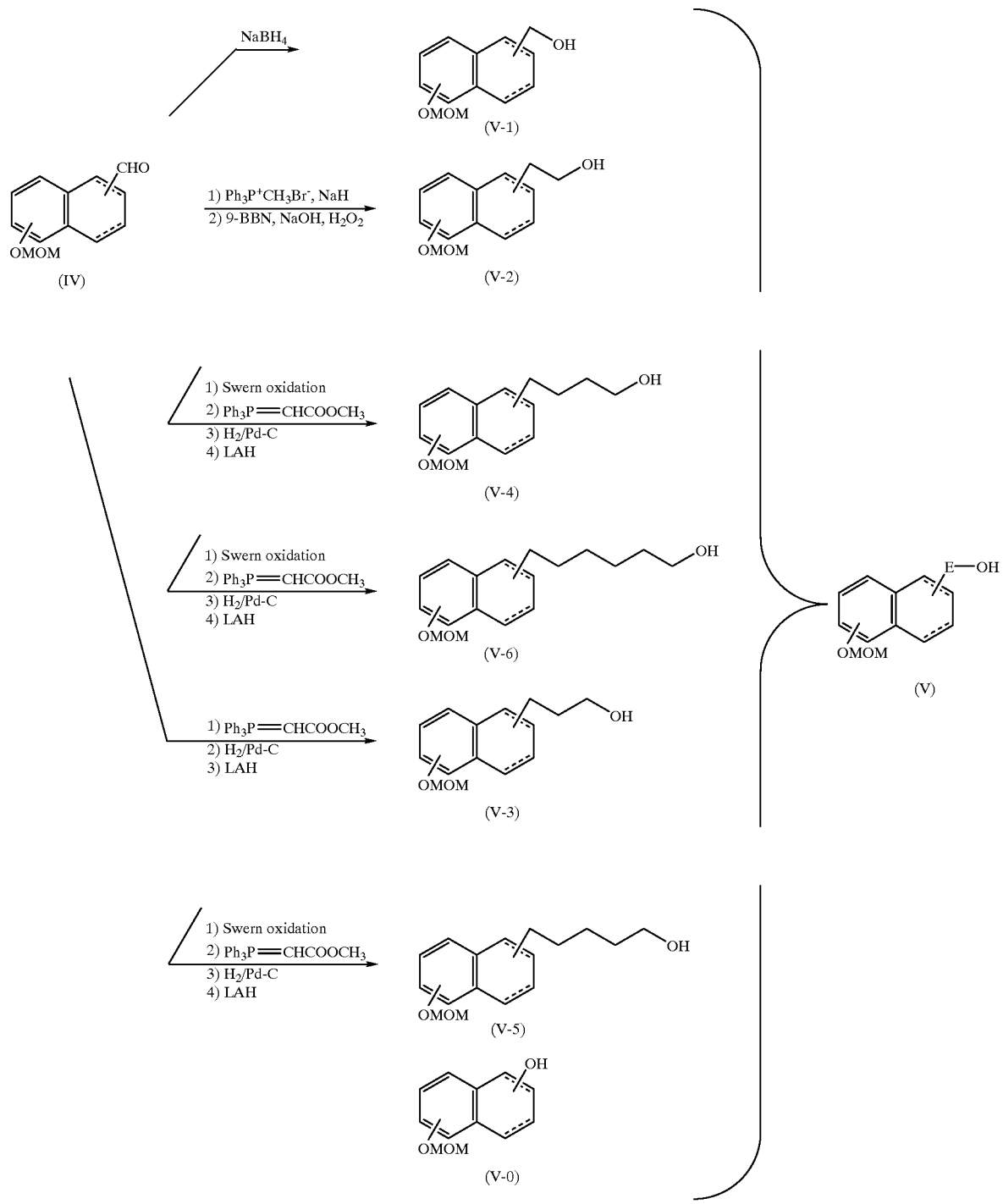

Reaction Scheme 2
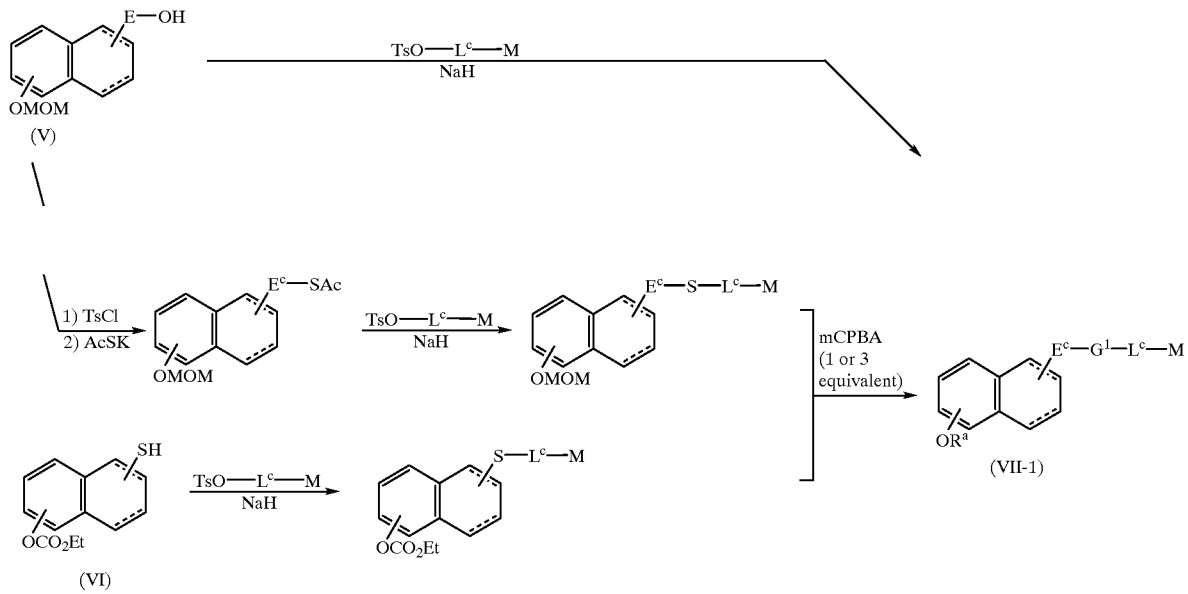
Reaction Scheme 3
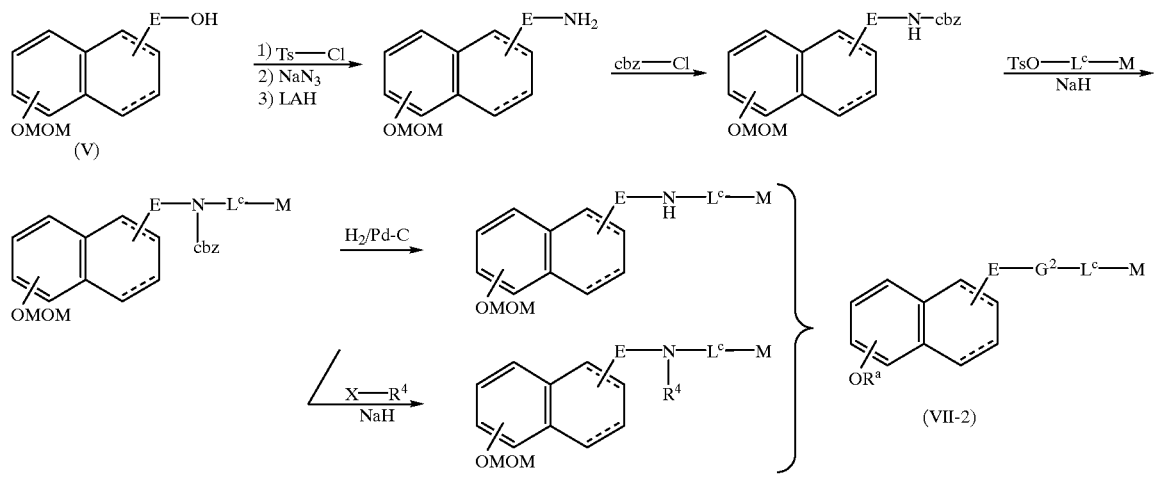

Reaction Scheme 4
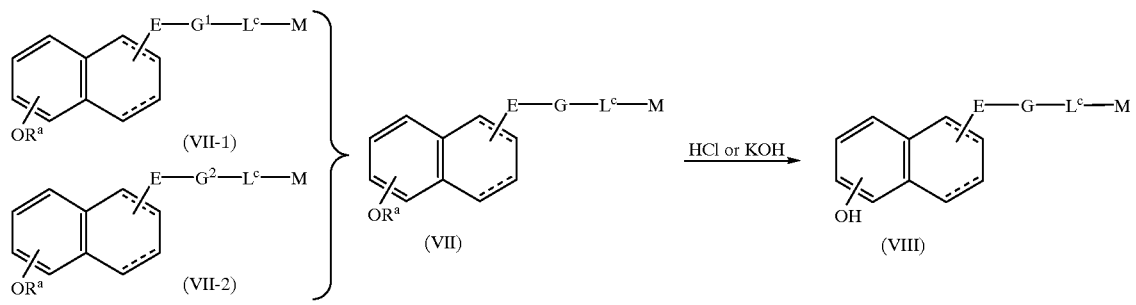
Reaction Scheme 5
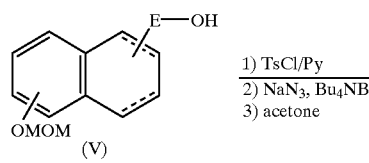
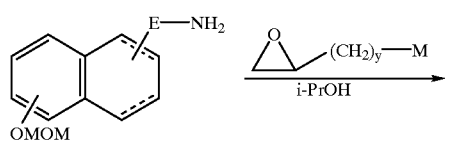
-continued
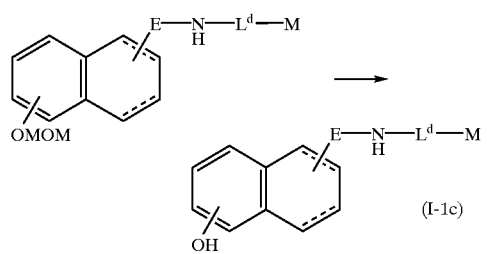

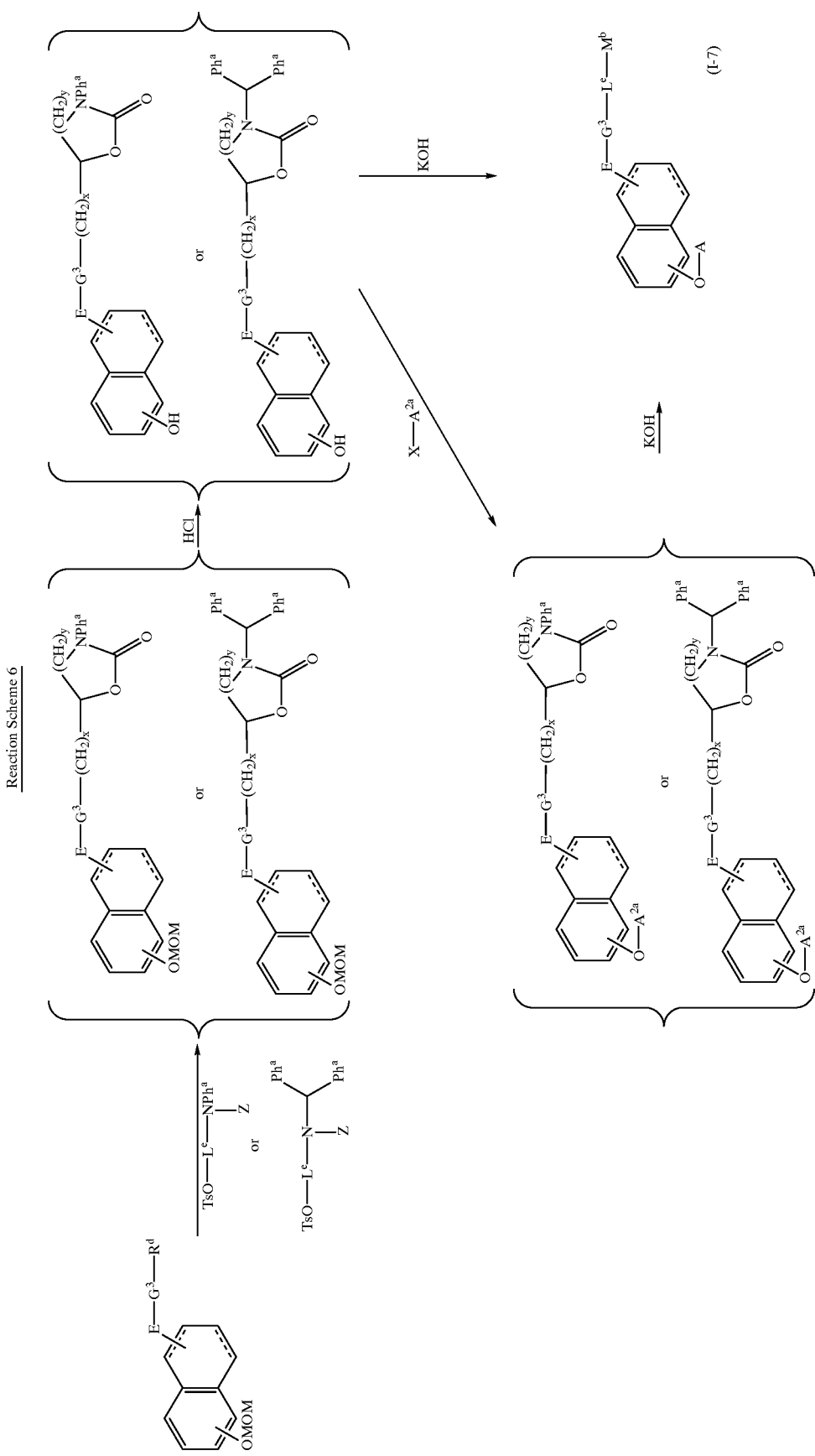

Industrial Availability

Pharmacological Activities

The compounds of the present invention of the formula (I) are useful as $PGE_2$ antagonists or agonists, because they can bind onto prostaglandin $E_2$ receptors and have antagonist or agonist activity against the action thereof.

As mentioned hereinbefore, to antagonize $PGE_2$ receptor is linked to inhibit diuretic, to inhibit hyperlipemia, to inhibit reduce of blood sugar, to inhibit uterine contraction, to have analgesic action, to inhibit digestive peristalsis, to induce sleep. Therefor, $PGE_2$ antagonists are considered to be useful as anti-hyperlipemia, for the prevention of abortion, for analgesics, or as antidiarrheals or sleep inducer.

As mentioned hereinbefore, to agonize for $PGE_2$ receptor is liked to promote diuretic, to promote hyperlipemia, to promote reduce of blood sugar, to contractile uterine, to promote digestive peristalsis, to suppress gastric acid secretion or to reduce blood pressure. Therefor, $PGE_2$ receptor agonists are considered to be useful for diuretic, anti-diabetes, abortient, cathartics, antiulcer, anti-gastritis or anti-hypertensive.

For example, in standard laboratory test, the effects of the compounds of the present invention were confirmed by inhibitory effect on binding $PGE_2$ using expression cell of receptor.

(I) Binding Assay using Expression Cell of Prostanoide Receptor Subtype

The preparation of membrane fraction was carried out according to the method of Sugimoto et al (J. Biol. Chem. 267, 6463–6466 (1992)), using expression CHO cell of prostanoide receptor subtype (mouse $EP_3\alpha$).

The standard assay mixture contained membrane fraction (0.5 mg/ml), [$^3$H]-$PGE_2$ in a final volume of 200 ml was incubated for 1 hour at room temperature. The reaction was terminated by addition of 3 ml of ice-cold buffer. The mixture was rapidly filtered through a glass filter (GF/B). The radioactivity associated with the filter was measured by liquid scintillation counting.

Kd and Bmax values were determined from Scatchard plots (Ann. N.Y. Acad. Sci., 51, 660 (1949)). Non-specific binding was calculated as the bond in the presence of an excess (2.5 nM) of unlabeled $PGE_2$. In the experiment for competition of specific [$^3$H]-$PGE_2$ binding by the compounds of the present invention, [$^3$H]-$PGE_2$ was added at a concentration of 2.5 nM and the compounds of the present invention were at a concentration of 1 mM. Buffer: 10 mM potassium phosphate (pH6.0), 1 mM EDTA, 10 mM $MgCl_2$, 0.1 M NaCl.

The dissociation constant Ki ($\mu$M) of each compound was calculated by the following equation.

Ki =IC50/(1+([C]/Kd))

The results were shown as follows.

| Example No. | dissociation constant Ki ($\mu$M) |
|---|---|
| 3 | 0.048 |
| 3 (2) | 0.0099 |
| 3 (6) | 0.15 |
| 3 (8) | 2.0 |
| 5 | 0.080 |
| 5 (1) | 0.0086 |

Toxicity

The toxicity of the compounds of the present invention are very low and therefore, it is confirmed that these compounds are safe for use as medicine.

Application for Pharmaceuticals

The compounds of the formula (I) of the present invention are useful for $PGE_2$ antagonists or agonists, because they can bind onto $PGE_2$ receptors and have an activity to antagonize or agonize for the action thereof.

As mentioned hereinbefore, to antagonize $PGE_2$ is linked to inhibit hyperlipemia, to inhibit uterine contraction, to have analgesic action, to inhibit digestive peristalsis or to induce sleep. Therefor, $PGE_2$ antagonists are considered to be useful as anti-hyperlipemia, for the prevention of abortion, for analgesics, or as antidiarrheals or sleep inducer.

As mentioned hereinbefore, to agonize $PGE_2$ is linked to promote diuretic, to promote reduce of blood sugar, to contractile uterine, to promote digestive peristalsis, to suppress gastric acid secretion or to reduce blood pressure. Therefor, $PGE_2$ agonists are useful for diuretics, anti-diabete abortient, cathartics, antiulcer, anti-gastritis or antihypertensive.

For the purpose above described, the compounds of the formula (I), non-toxic salts thereof and hydrates thereof may be normally administered systematically or partially, usually by oral or parenteral administration.

The doses to be administered are determined depending upon age, body weight, symptom, the desired therapeutic effect, the route of administration, and the duration of the treatment etc. In the human adult, the doses per person per dose are generally between 1 $\mu$g and 100 mg, by oral administration, up to several times per day, and between 0.1 $\mu$g and 10 mg, by parenteral administration (preferred into vein) up to several times per day, or continuous administration between 1 and 24 hours per day into vein.

As mentioned above, the doses to be used depend upon various conditions. Therefore, there are cases in which doses lower than or greater than the ranges specified above may be used.

On administration of the compounds of the present invention, it is used as solid compositions, liquid compositions or other compositions for oral administration, as injections, liniments or suppositories etc. for parenteral administration.

Solid compositions for oral administration include compressed tablets, pills, capsules, dispersible powders, and granules etc.

Capsules contain hard capsules and soft capsules.

In such solid compositions, one or more of the active compound(s) is or are, admixed with at least one inert diluent such as lactose, mannitol, mannit, glucose, hydroxypropyl cellulose, microcrystalline cellulose, starch, polyvinylpyrrolidone, magnesium metasilicate aluminate. The compositions may also comprise, as is normal practice, additional substances other than inert diluents: e.g. lubricating agents such as magnesium stearate, disintegrating agents such as cellulose calcium glycolate, and assisting agents for dissolving such as glutamic acid or asparaginic acid. The tablets or pills may, if desired, be coated with film of gastric or enteric material such as sugar, gelatin, hydroxypropyl cellulose or hydroxypropyl cellulose phthalate etc., or be coated with two or more films. And further, coating may include containment within capsules of absorbable materials such as gelatin.

Liquid compositions for oral administration include pharmaceutically-acceptable emulsions, solutions, syrups and elixirs etc. In such liquid compositions, one or more of the active compound(s) is or are comprised in inert diluent (s) commonly used in the art (for example, purified water, ethanol etc.). Besides inert diluents, such compositions may also comprise adjuvants such as wetting agents, suspending agents, sweetening agents, flavouring agents, perfuming agents and preserving agents.

Other compositions for oral administration include spray compositions which may be prepared by known methods and which comprise one or more of the active compound(s). Spray compositions may comprise additional substances other than inert diluents: e.g. stabilizing agents such as sodium hydrogen sulfate, stabilizing agents to give the title compound isotonicity, isotonic buffer such as sodium chloride, sodium citrate, citric acid. For preparation of such spray compositions, for example, the method described in the U.S. Pat. No. 2,868,691 or 3,095,355 may be used.

Injections for parenteral administration include sterile aqueous or non-aqueous solutions, suspensions and emulsions. Aqueous solutions or suspensions include distilled water for injection and physiological salt solution. Non-aqueous solutions or suspensions include propylene glycol, polyethylene glycol, plant oil such as olive oil, alcohol such as ethanol, POLYSOLBATE80 (registered trade mark) etc. Such compositions may comprise additional diluents: e.g. preserving agents, wetting agents, emulsifying agents, dispersing agents, stabilizing agent, assisting agents such as assisting agents for dissolving (for example, glutamic acid, asparaginic acid). They may be sterilized for example, by filtration through a bacteria-retaining filter, by incorporation of sterilizing agents in the compositions or by irradiation. They also be manufactured in the form of sterile solid compositions and which can be dissolved in sterile water or some other sterile diluents for injection immediately before used.

Other compositions for parenteral administration include liquids for external use, and endemic liniments, ointment, suppositories and pessaries which comprise one or more of the active compound(s) and may be prepared by know methods.

BEST MODE TO PRACTICE THE INVENTION

The following reference examples and examples are intended to illustrate, but not limit, the present invention. The solvents in parentheses show the developing or eluting solvents and the ratios of the solvents used are by volume in chromatographic separations. The symbol in the structure is the same meaning as defined hereinbefore.

REFERENCE EXAMPLE 1

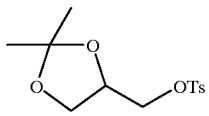

To a solution of 2,2-dimethyl-1,3-dioxolane-4-methanol (50 g) and pyridine (50 ml) in methylene chloride (200 ml), tosylchloride (76.3 g) in methylene chloride (150 ml) was added dropwise at −20° C. The mixture was stirred for 1 hour at room temperature. The reaction mixture was added to 2N aqueous solution of hydrochloric acid (300 ml) and extracted by ethyl acetate. The organic layer was washed with water and a saturated aqueous solution of sodium chloride, dried over with anhydrous magnesium sulfate and concentrated. The residue was purified on silica gel column chromatography (hexane:AcOEt=3:1) to give the title compound (95.8 g) having the following physical data.

TLC: Rf 0.21 (hexane:AcOEt=3:1); MS (EI): m/z 271 ($M^+$—$CH_3$).

REFERENCE EXAMPLE 2

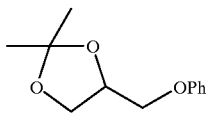

A suspension of sodium hydride (1.47 g) in dimethylformamide (DMF) (20 ml) was cooled to 0° C. The solution of phenol (3.45 g) in DMF (20 ml) was added dropwise to the suspension. The mixture was stirred for 1 hour at room temperature. To the mixture, the solution of the compound prepared in Reference Example 1 (10 g) in DMF (20 ml) was added. The mixture was stirred for 2 hours at 80° C. The reaction mixture was cooled to room temperature, poured into iced water and extracted with ether two times. The organic layer was washed with water and a saturated aqueous solution of sodium chloride, dried over with anhydrous magnesium sulfate and concentrated. The residue was purified on silica gel column chromatography (hexane:AcOEt=9:1) to give the title compound (6.53 g) having the following physical data.

TLC: Rf 0.22 (hexane:AcOEt=9:1); MS (EI): m/z 208 ($M^+$), 193.

REFERENCE EXAMPLE 3

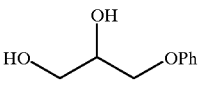

To a solution of the compound prepared in Reference Example 2 (6.37 g) in methanol (30 ml), 2N aqueous solution of hydrochloric acid (3 ml) was added. The mixture was refluxed for 2 hours. The reaction mixture was cooled to room temperature, diluted with ethyl acetate and washed with saturated aqueous solution of sodium hydrogen carbonate. The organic layer was dried over with anhydrous magnesium sulfate and concentrated to give the title compound (5.14 g) having the following physical data.

TLC: Rf 0.40 (AcOEt); MS (EI): m/z 168 ($M^+$).

REFERENCE EXAMPLE 4

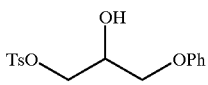

To a solution of the compound prepared in Reference Example 3 (3.5 g) in pyridine (10 ml), the solution of tosylchloride (8 g) in methylene chloride (10 ml) was added at −20° C. The mixture was stirred for 1 hour at room temperature. The reaction mixture was poured into 2N aqueous solution of hydrochloric acid and extracted with ethyl acetate. The organic layer was washed with water and a saturated aqueous solution of sodium chloride, dried over with anhydrous magnesium sulfate and concentrated. The residue was purified on silica gel column chromatography (AcOEt:CH$_2$Cl$_2$=1:49) to give the title compound (4.96 9) having the following physical data.

TLC: Rf 0.31 (hexane:AcOEt=3:2); MS (EI): m/z 322 (M$^+$).

REFERENCE EXAMPLE 5

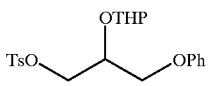

To a solution of the compound prepared in Reference Example 4 (9.88 g) and pyridium p-toluene sulfate (100 mg) in methylene chloride (60 ml), dihydropyran (5.58 ml) was added dropwise at 0° C. The mixture was stirred for 6 hours at room temperature. Triethylamine (0.2 ml) was added to the mixture. The solvent was distilled off. The residue was purified on silica gel column chromatography (hexane:AcOEt=41:9) to give the title compound (11.79 g) having the following physical data.

TLC: Rf 0.28 (hexane:AcOEt=4:1); MS (EI): m/z 406 (M$^+$).

REFERENCE EXAMPLE 6

By using (S)-(+)-2,2-dimethyl-1,3-dioxolane-4-methanol instead of 2,2-dimethyl-1,3-dioxolane-4-methanol as starting material, the title compound having the following physical data was obtained by the same procedure as Reference Example 1→Reference Example 2→Reference Example 3→Reference Example 4→Reference Example 5.

TLC: Rf 0.28 (hexane:AcOEt=4:1); MS (EI): m/z 406 (M$^+$).

REFERENCE EXAMPLE 6(1)

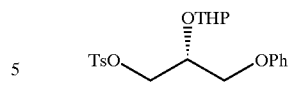

By using (R)-(−)-2,2-dimethyl-1,3-dioxolane-4-methanol instead of 2,2-dimethyl-1,3-dioxolane-4-methanol as starting material, the title compound having the following physical data was obtained by the same procedure as Reference Example 6.

TLC: RF 0.28 (hexane:AcOEt=4:1); MS (EI): m/z 406 (M$^+$).

REFERENCE EXAMPLE 7

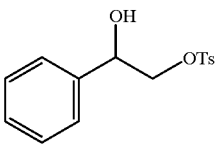

To a solution of 1-phenyl-1,2-ethandiol (13.82 g) in pyridine (50 ml), tosylchloride (21 g) was added for 30 minutes at −20° C. The reaction mixture was stirred for 30 minutes at −20° C. and, succeedingly, stirred for 16 hours at room temperature. The reaction mixture was poured into iced water and extracted with ether. The organic layer was washed with 2N aqueous solution of hydrochloric acid, water and saturated aqueous solution of sodium hydrogen carbonate, succeedingly, dried over with anhydrous sodium sulphate and concentrated. The residue was purified on silica gel column chromatography (hexane:AcOEt=3:1) to give the title compound (18.56 g) having the following physical data.

TLC: Rf 0.41 (hexane:AcOEt=2:1); MS (EI): m/z 292 (M$^+$).

REFERENCE EXAMPLE 8

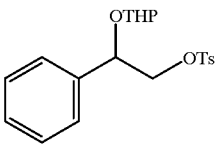

To a solution of compound prepared in Reference Example 7 (10 g) in methylene chloride (100 ml), dihydropyran (5.76 g) was added dropwise at room temperature. P-toluene sulfonic acid (catalytic amount) was added to the mixture. The mixture was stirred overnight at room temperature. To the reaction mixture, triethylamine (two drops) was added. The mixture was concentrated. The reside was dissolved in ethyl acetate. The organic layer was washed with water and a saturated aqueous solution of sodium chloride, dried over with anhydrous sodium sulfate and concentrated to give the title compound (12.9 g) having the following physical data.

TLC: Rf 0.50(hexane:AcOEt=2:1); MS (EI): m/z 376 (M$^+$).

REFERENCE EXAMPLE 9

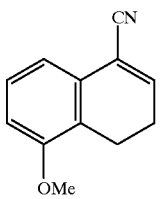

To a solution of 5-methoxy-1-tetralone (100 g) in methylene chloride (500 ml), trimethylsilylcyanide (88 ml) and zinc iodide (3 g) was added. The mixture was stirred overnight at room temperature. To the reaction solution, water was added. The mixture was extracted with mixture solvent (AcOEt:hexane=1:1) two times. The organic layer was washed with water and a saturated aqueous solution of sodium chloride, dried over anhydrous sodium sulfate and concentrated. The residue was dissolved in pyridine (370 ml). Phosphorous oxychloride (POCl$_3$) (133 ml) was added dropwise to the solution. The reaction mixture was refluxed for 3 hours and cooled to room temperature. The reaction mixture was poured into iced water and extracted with ethyl acetate two times. The organic layer was washed with water and a saturated aqueous solution of sodium chloride, dried over anhydrous sodium sulfate and concentrated. The residue was purified on silica gel column chromatography (AcOEt:CH$_2$Cl$_2$=1:19), and succeedingly, recrystalized from solvent of AcOEt-hexane to give the title compound (72 g) having the following physical data.

TLC: Rf 0.43 (hexane:AcOEt=3:1); MS (EI): m/z 185 (M$^+$).

REFERENCE EXAMPLE 10

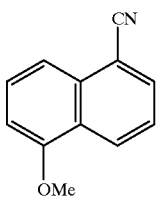

A mixture of compound prepared in Reference Example 9 (60 g), 2,3-dichloro-5,6-dicyano-1,4-benzoquinon (DDQ) (81 g) and benzene (700 ml) was refluxed for 6 hours. The reaction mixture was cooled to room temperature. To a reaction solution, mixture solvent (AcOEt:hexane=1:1) (500 ml) was added. The mixture was filtrated. The precipitate was washed with mixture solvent (AcOEt:hexane=1:1). The filtrate was washed with saturated aqueous solution of sodium hydrogen carbonate four times, dried over with anhydrous sodium sulfate and concentrated. The reside was recrystalized from AcOEt-hexane to give the title compound (56.6 g) having the following physical data.

TLC: RF 0.42 (hexane:AcOEt=3:1); MS (EI): m/z 183 (M$^+$); m.p. 132–133° C.

REFERENCE EXAMPLE 11

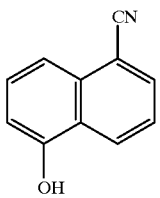

To a solution of compound prepared in Reference Example 10 (91.6 g) in methylene chloride (500 ml), a solution of boron triburomide (104 ml) in methylene chloride (100 ml) was added dropwise at 0° C. The mixture was stirred for 20 hours at room temperature. The reaction mixture was poured into iced water and extracted with ethyl acetate two times. The organic layer was washed with aqueous solution of sodium hydrogen carbonate and a saturated aqueous solution of sodium chloride, dried over with anhydrous magnesium sulfate and concentrated to give the title compound (84.4 g) having the following physical data.

TLC: Rf 0.32(hexane:AcOEt=2:1); MS (EI): m/z 169 (M$^+$); m.p. 198–201° C.

REFERENCE EXAMPLE 12

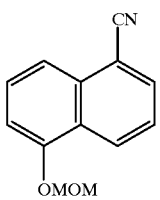

To a solution of compound prepared in Reference Example 11 (82.5 g) in methylene chloride (1000 ml), diisopropylethylamine (102 ml) and methyoxymethylchloride (41 ml) were added at 0° C. The mixture was stirred overnight at room temperature. The solvent was distilled off. The residue was diluted with mixture solvent (AcOEt:hexane=1:1), washed with water, aqueous solution of hydrochloric acid, saturated aqueous solution of sodium hydrogen carbonate and a saturated aqueous solution of sodium chloride succeedingly, dried over with anhydrous magnesium sulfate and concentrated. The residue was recrystallized from the mixture solvent (AcOEt:hexane=1:10) to give the title compound (88.8 g) having the following physical data.

TLC: Rf 0.34(hexane:AcOEt=4:1); MS (EI): m/z 213 (M$^+$).

REFERENCE EXAMPLE 13

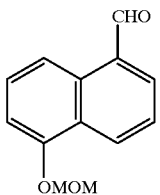

To a solution of compound prepared in Reference Example 12 (95.5 g) in toluene (750 ml), diisobutyl aluminum hydride (324 ml, 1.5 mol/toluene solution) was added at −50° C. The mixture was heated to 0° C. for 2 hours. The reaction mixture was cooled to −30° C. Methanol (30 ml) was added to the mixture. The reaction solution was heated to −5° C. An aqueous solution of sodium sulfate was added to the mixture. The precipitate was filtrated. The filtrate was concentrated. The residue was dissolved in tetrahydrofuran (THF)-AcOEt (100 ml–400 ml). 2N aqueous solution of hydrochloric acid (250 ml) was added to the solution. The mixture was stirred for 30 minutes. The organic layer was isolated. The aqueous layer was extracted with ethyl acetate. The organic layer was washed with an aqueous solution of sodium hydrogen carbonate and a saturated aqueous solution of sodium chloride, dried over with anhydrous magnesium sulfate and concentrated. To the residue, hexane (600 ml) was added. The mixture was laid for 2 days. The crystal was collected by filtration to give the title compound (70.6 g) having the following physical data. In addition, the mother liquor was purified on silica gel column chromatography (hexane:AcOEt=7:1) to give the title compound (20.9 g) having the following physical data.

TLC: Rf 0.33 (hexane:AcOEt=3:1); MS (EI): m/z 216 (M+).

REFERENCE EXAMPLE 14

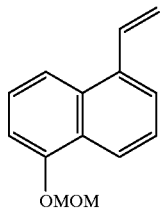

A mixture of sodium hydride (4.66 g) and dimethylsulfoxide (DMSO) (100 ml) was stirred for 50 minutes at 80° C. The reaction mixture was cooled to room temperature. A solution of methyltriphenylphosphnium bromide (41.6 g) in DMSO (120 ml) was added dropwise to the reaction mixture in order to adjust reaction temperature to 20–30° C. The mixture was stirred for 30 minutes at room temperature. To the reaction solution, a solution of compound prepared in Reference Example 13 (15.56 g) in DMSO (80 ml) was added dropwise. The mixture was stirred for 15 minutes at room temperature. The reaction mixture was poured into iced water, extracted with mixture solvent (AcOEt:hexane= 1:2) three times. The organic layer was washed with water and a saturated aqueous solution of sodium chloride, dried over with anhydrous magnesium sulfate and concentrated. To the residue, mixture solvent (ether:hexane=1:4) (200 ml) was added. The mixture was filtrated. The filtrate was concentrated. The residue was purified on silica gel column chromatography (hexane:AcOEt=6:1) to give the title compound (14.2 g) having the following physical data.

TLC: RF 0.52(hexane:AcOEt=4:1); MS (EI): m/z 214 (M+).

REFERENCE EXAMPLE 15

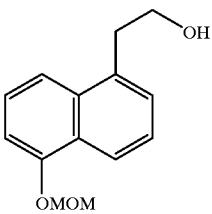

To a solution of compound prepared in Reference Example 14 (14.2 g) in THF (60 ml), 9-borabicyclo[3.3.1] nonane (9-BBN) (172 ml, 0.5 mol/l THF solution) was added dropwise under an atmosphere of Argon gas at room temperature. The mixture was stirred for 2.5 hours at room temperature. To the reaction solution, ethanol (30 ml) was added dropwise. In addition, to the mixture, 5N-aqueous solution of sodium hydroxide (50 ml) was added. An aqueous solution of hydrogen peroxide (50 ml) was added dropwise to the mixture in order to adjust reaction temperature to 50–60° C. The reaction mixture was stirred for 30 minutes, poured into iced water and extracted with ethyl acetate two times. The organic layer was washed with water and a saturated aqueous solution of sodium chloride, dried over with anhydrous magnesium sulfate and concentrated. The residue was purified on silica gel column chromatography (hexane:AcOEt=7:3) to give the title compound (14.81 g) having the following physical data.

TLC: Rf 0.38 (hexane:AcOEt=7:3); MS (EI): m/z 232 (M+), 202.

REFERENCE EXAMPLE 16

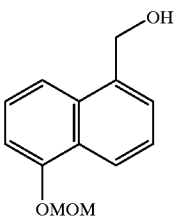

To a solution of compound prepared in Reference Example 13 (5.3 g) in methanol (40 ml), sodium boron hydride (910 mg) was added. The mixture was stirred for 1 hour at room temperature. The solvent was distilled off. Water was added to the reside. The mixture was extracted with ethyl acetate. The organic layer was washed with water and a saturated aqueous solution of sodium chloride, dried over with anhydrous magnesium sulfate and concentrated to give the title compound (5.21 g) having the following physical data.

TLC: Rf 0.33 (hexane:AcOEt=2:1); MS (EI): m/z 218 (M+).

REFERENCE EXAMPLE 17

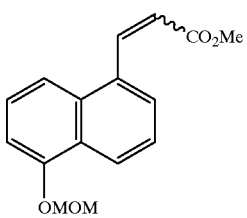

To a solution of compound prepared in Reference Example 13 (3.11 g) in chloroform (30 ml), carbomethoxymethylene triphenylphosphorane (98% 5.88 g) was added. The mixture was stirred for 16 hours at room temperature. The reaction mixture was concentrated. Ether was added to the residue. The precipitate was filtrated. The filtrate was concentrated. The residue was dissolved in hexane. The precipitate was filtrated. The filtrate was concentrated to give the title compound (3.92 g) having the following physical data.

TLC: Rf 0.50 (hexane:AcOEt=5:1); MS (EI): m/z 272 (M$^+$).

REFERENCE EXAMPLE 18

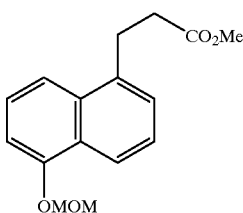

To a solution of compound prepared in Reference Example 17 (3.81 g) in ethyl acetate (70 ml), 10% Pd—C (380 mg) was added. The mixture was stirred under an atmosphere of H$_2$ gas for 1 hour. The reaction solution was filtrated. The filtrate was concentrated to give the title compound (3.69 g) having the following physical data.

TLC: Rf 0.48 (hexane:AcOEt=5:1); MS (EI): m/z 274 (M$^+$).

REFERENCE EXAMPLE 19

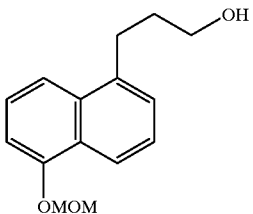

To a suspension of lithium aluminum hydride (2.91 g) in THF (50 ml), a solution of compound prepared in Reference Example 18 (12.5 g) in THF (150 ml) was added dropwise at room temperature. The mixture was stirred for 1 hour at room temperature. A small amount of ethyl acetate was added to the reaction mixture. A saturated aqueous solution of anhydrous sodium sulfate was added to the mixture. The white precipitate was filtrated by Celite (Registered trademark). The filtrate was concentrated to give the title compound (11.35 g) having the following physical data.

TLC: Rf 0.27 (hexane:AcOEt=2:1); MS (EI): m/z 246 (M$^+$).

REFERENCE EXAMPLE 20

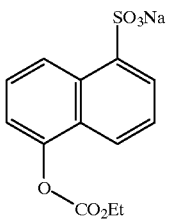

6-Hydroxy-2-naphthalene sulfonic acid sodium salt (18 g) was dissolved in 2N aqueous solution of sodium hydroxide (36.6 ml) with heating. THF (70 ml) was added to the solution. Ethylchloroformate (7 ml) was added dropwise to the mixture under cooling with ice. The mixture was stirred for 3 hours at room temperature. The white crystal was filtrated, washed with water and THF and dried over under reduced pressure to give the title compound (16.3 g) having the following physical data.

TLC: Rf 0.09 (CHCl$_3$:MeOH=5:1); MS (EI): m/z 318 (M$^+$).

REFERENCE EXAMPLE 21

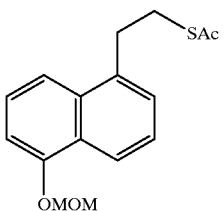

The solution of compound prepared in Reference Example 15 (7.63 g) in pyridine (20 ml) was cooled to −30° C. Tosylchloride (8.75 g) was added to the solution. The mixture was stirred for 2 hours at room temperature. The reaction mixture was cooled to 0° C. Water (1 ml) was added to the mixture. The mixture was stirred for 20 minutes at room temperature. The reaction solution was poured into AcOEt-2N-aqueous solution of hydrochloric acid (2:1, 400 ml). The organic layer was isolated, washed with water and saturated aqueous solution of sodium hydrogen carbonate, dried over with anhydrous magnesium sulfate and concentrated. The residue was dissolved in acetone (100 ml). Potassium thioacetate (5.62 g) was added to solution. The mixture was refluxed for 2 hours. The reaction mixture was cooled to room temperature, poured into water and extracted with mixture solvent (AcOEt:hexane=1:2) two times. The organic layer was washed with water and a saturated aqueous solution of sodium chloride, dried over with anhydrous magnesium sulfate and concentrated to give the title compound (9.28 g) having the following physical data.

TLC: Rf 0.55 (hexane:AcOEt=7:3); MS (EI): m/z 290 (M$^+$).

REFERENCE EXAMPLE 21(1)

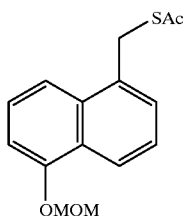

By using compound prepared in Reference Example 16, the title compound having the following physical data was obtained by the same procedure of Reference Example 21.

TLC: Rf 0.40 (hexane:AcOEt=4:1); MS (EI): m/z 276 ($M^+$).

REFERENCE EXAMPLE 21(2)

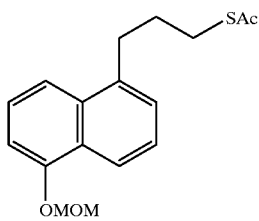

By using compound prepared in Reference Example 19, the title compound having the following physical data was obtained by the same procedure of Reference Example 21.

TLC: Rf 0.57 (hexane:AcOEt=7:3); MS (EI): m/z 304 ($M^+$).

REFERENCE EXAMPLE 22

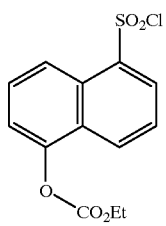

To a solution compound prepared in Reference Example 20 (16.3 g) in DMF (150 ml), thionylchloride (18.7 ml) was added dropwise for 1.5 hours at 0° C. The mixture was stirred for 2.5 hours at room temperature. The reaction mixture was poured into iced water. The white crystal was filtrated, washed with water and dried over under reduced pressure to give the title compound (13.4 g) having the following physical data.

TLC: Rf 0.72 (hexane:AcOEt=1:1); MS (EI): m/z 314 ($M^+$).

REFERENCE EXAMPLE 23

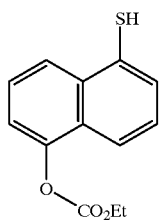

The compound prepared in Reference Example 22 (13.5 g) was dissolved in mixture solvent of water (90 ml), conc. sulfuric acid (18 ml) and THF (100 ml). A powder of zinc (13.9 g) was added to the solution at 0° C. The mixture was stirred overnight at room temperature. The reaction solution was filtrated. The filtrate was distilled off under reduced pressure. The residual aqueous solution was extracted with ethyl acetate. The organic layer was dried over with anhydrous magnesium sulfate, and concentrated. The residue was purified on silica gel column chromatography (hexane:AcOEt=1:1) to give the title compound (9.4 g) having the following physical data.

TLC: Rf 0.22 (hexane:AcOEt=1:1); MS (EI): m/z 248 ($M^+$).

REFERENCE EXAMPLE 24

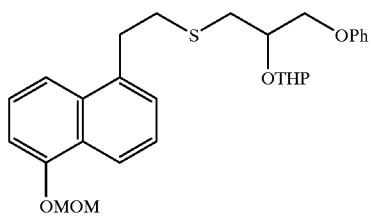

To a solution of the compound prepared in Reference Example 21 (4.5 g) and the compound prepared in Reference Example 5 (6.3 g) in ethanol (30 ml), sodium ethoxide (1.4 g) was added at 0° C. The mixture was stirred for 1 hour at room temperature. The reaction mixture was poured into iced water and extracted with ethyl acetate two times. The organic layer was washed with water and a saturated aqueous solution of sodium chloride, dried over with anhydrous magnesium sulfate and concentrated. The residue was purified on silica gel column chromatography (hexane:AcOEt=6:1) to give the title compound (6.75 g) having the following physical data.

TLC: Rf 0.32(hexane:AcOEt=5:1); MS (EI): m/z 482 ($M^+$).

REFERENCE EXAMPLE 24(1)

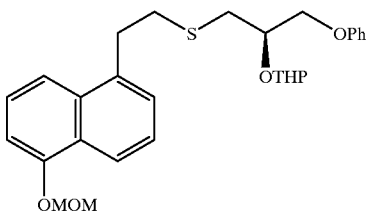

By using the compound prepared in Reference Example 21 and the compound prepared in Reference Example 6, the title compound having the following physical data by the same procedure of Reference Example 24.

TLC: Rf 0.32 (hexane:AcOEt=5:1); MS (EI): m/z 482 ($M^+$).

REFERENCE EXAMPLE 24(2)

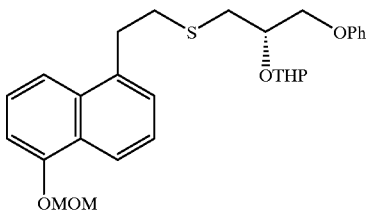

By using the compound prepared in Reference Example 21 and the compound prepared in Reference Example 6(1), the title compound having the following physical data by the same procedure of Reference Example 24.

TLC: Rf 0.32 (hexane:AcOEt=5:1); MS (EI): m/z 482 ($M^+$).

REFERENCE EXAMPLE 24(3)

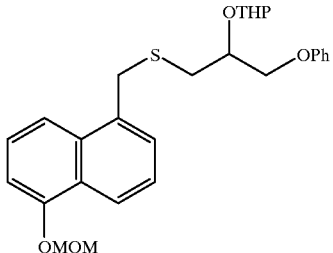

By using the compound prepared in Reference Example 21(1) and the compound prepared in Reference Example 5 the title compound having the following physical data by the same procedure of Reference Example 24.

TLC: Rf 0.32(hexane:AcOEt=4:1); MS (EI): m/z 468 ($M^+$).

REFERENCE EXAMPLE 25

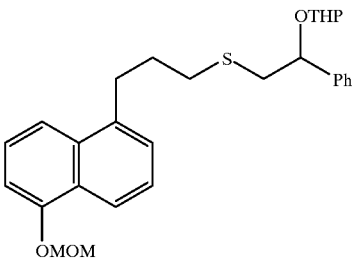

To a solution of the compound prepared in Reference Example 21(2) (61 mg) and the compound prepared in Reference Example 8 (75 mg) in ethanol (4 ml), sodium ethoxide (28 mg) was added. The mixture was stirred for 1 hour at room temperature. The reaction mixture was concentrated. Water was added to the residue. The mixture was extracted with ethyl acetate. The organic layer was washed with water and a saturated aqueous solution of sodium chloride, dried over with anhydrous sodium sulfate and concentrated. The residue was purified on silica gel column chromatography (hexane:AcOEt=5:1) to give the title compound (68 mg) having the following physical data.

TLC: Rf 0.65 (hexane:AcOEt=5:1); MS (EI): m/z 466 ($M^+$).

REFERENCE EXAMPLE 26

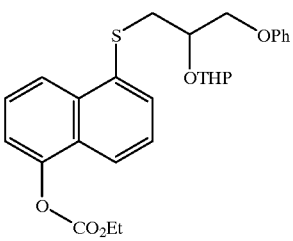

To a solution of sodium hydride (400 mg) in DMF (30 ml), the compound prepared in Reference Example 23 (2.48 g) was added under an atmosphere of Argon gas. The mixture was stirred for 30 minutes at room temperature. A solution of the compound prepared in Reference Example 5 (4.06 9) in DMF (5 ml) was added dropwise to the reaction solution at 0° C. The mixture was stirred for 6 hours at room temperature. Water (30 ml) was added to the reaction solution. The mixture was extracted with ethyl acetate. The organic layer was dried over with anhydrous magnesium sulfate and concentrated. The residue was purified on silica gel column chromatography (hexane:AcOEt=2:1) to give the title compound (3.44 g) having the following physical data.

TLC: Rf 0.49(hexane:AcOEt=5:1); MS (EI): m/z 482 ($M^+$).

REFERENCE EXAMPLE 27

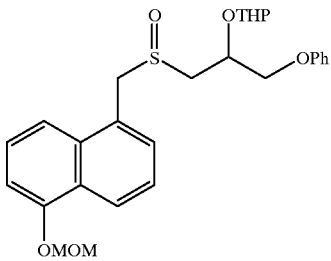

To a suspension of the compound prepared in Reference Example 24(3) (466 mg) and sodium hydrogen carbonate (170 mg) in methylene chloride (2 ml), 70% mCPBA (245 mg) was added at 0° C. The mixture was stirred for 1 hour at 0° C. Water was added to the reaction mixture. The mixture was extracted with ether. The organic layer was washed with water and a saturated aqueous solution of sodium chloride, dried over with anhydrous magnesium sulfate and concentrated. The residue was purified on silica gel column chromatography (hexane:AcOEt=1:4) to give the title compound (324 mg) having the following physical data.

TLC: Rf 0.12 (hexane:AcOEt=1:1); MS (EI): m/z 468 ($M^+$—O).

REFERENCE EXAMPLE 27(1)

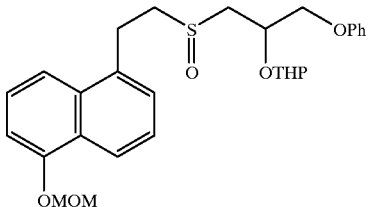

By using the compound prepared in Reference Example 24, the title compound having the following physical data was obtained by the same procedure of Reference Example 27.

TLC: Rf 0.44 (hexane:AcOEt=1:1); MS (EI): m/z 498 ($M^+$).

REFERENCE EXAMPLE 27(2)

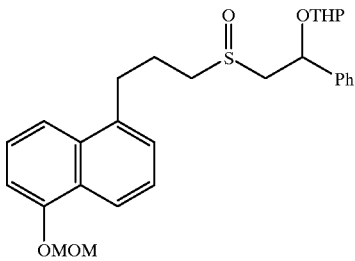

By using the compound prepared in Reference Example 25, the title compound having the following physical data was obtained by the same procedure of Reference Example 27.

TLC: Rf 0.61 (AcOEt); MS (EI): m/z 482 ($M^+$).

REFERENCE EXAMPLE 27(3)

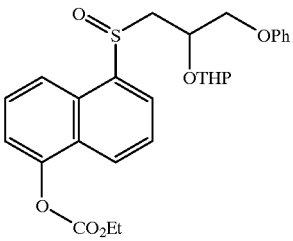

By using the compound prepared in Reference Example 26, the title compound having the following physical data was obtained by the same procedure of Reference Example 27.

TLC: Rf 0.33 (hexane:AcOEt=1:1); MS (EI): m/z 498 ($M^+$).

REFERENCE EXAMPLE 28

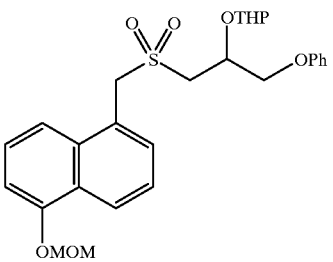

To a suspension of the compound prepared in Reference Example 24(3) (466 mg) and sodium hydrogen carbonate (340 mg) in methylene chloride (3 ml), 70% mCPBA (735 mg) was added at 0° C. The mixture was stirred for 2 hours at 0° C. Water was added to the reaction mixture. The mixture was extracted with ether. The organic layer was washed with water and a saturated aqueous solution of sodium chloride, dried over with anhydrous magnesium sulfate and concentrated. The residue was purified on silica gel column chromatography (hexane:AcOEt=2:1) to give the title compound (300 mg) having the following physical data.

TLC: Rf 0.37 (hexane:AcOEt=1:1); MS (EI): m/z 500 ($M^+$).

REFERENCE EXAMPLE 28(1)

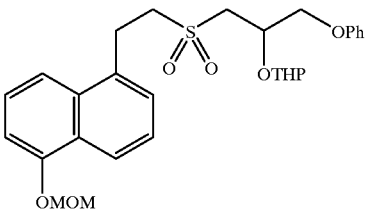

By using the compound prepared in Reference Example 24, the title compound having the following physical data was obtained by the same procedure of Reference Example 28.

TLC: Rf 0.49 (hexane:AcOEt=1:1); MS (EI): m/z 514 ($M^+$).

REFERENCE EXAMPLE 28(2)

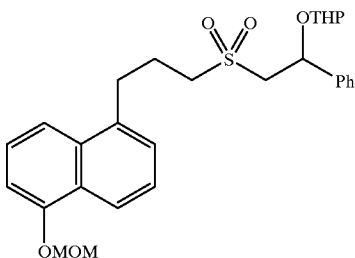

By using the compound prepared in Reference Example 25, the title compound having the following physical data was obtained by the same procedure of Reference Example 28.

TLC: Rf 0.27 (hexane:AcOEt=5:1); MS (EI): m/z 498 (M+).

REFERENCE EXAMPLE 28(3)

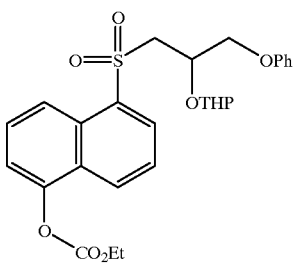

By using the compound prepared in Reference Example 26, the title compound having the following physical data was obtained by the same procedure of Reference Example 28.

TLC: Rf 0.35 (hexane:AcOEt=1:1); MS (EI): m/z 514 (M+).

REFERENCE EXAMPLE 29

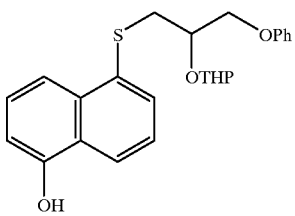

To a solution of potassium hydroxide (62 mg) in methanol (10 ml), the compound prepared in Reference Example 26 (446 mg) was added at room temperature. The mixture was stirred overnight at room temperature. 2N aqueous solution of hydrochloric acid was added to the reaction mixture in order to adjust to pH 7 at 0° C. The mixture was extracted with ethyl acetate. The organic layer was washed with water and a saturated aqueous solution of sodium chloride, dried over with anhydrous magnesium sulfate and concentrated, The white crystal was washed with ether to give the title compound (341 mg) having the following physical data.

TLC: Rf 0.34 (hexane:AcOEt=5:1); MS (EI): m/z 410 (M+).

REFERENCE EXAMPLE 29(1)

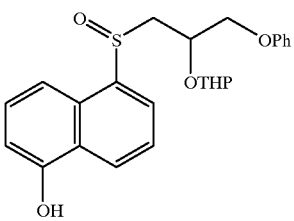

By using the compound prepared in Reference Example 27(3), the title compound having the following physical data was obtained by the same procedure of Reference Example 29.

TLC: Rf 0.31 (hexane:AcOEt=1:1); MS (EI): m/z 426 (M+).

REFERENCE EXAMPLE 29(2)

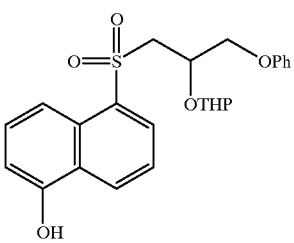

By using the compound prepared in Reference Example 28(3), the title compound having the following physical data was obtained by the same procedure of Reference Example 29.

TLC: Rf 0.32 (hexane:AcOEt=1:1); MS (EI): m/z 442 (M+).

EXAMPLE 1

1-[2-(5-Hydroxy-1-naphthyl)ethylthio]-3-phenoxy-2RS-propanol

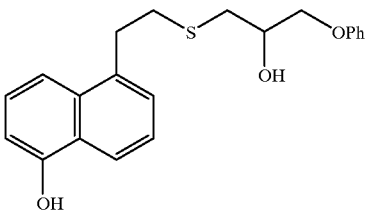

To a solution of the compound prepared in Reference Example 24 (482 mg) in mixture solvent of AcOEt-methanol (3 ml–2 ml), 4N aqueous solution of hydrochloric acid (3 ml, solution of ethyl acetate) was added. The mixture was stirred for 2 hours at room temperature. The reaction solution was concentrated. The residue was diluted with ethyl acetate, washed with water and a saturated aqueous solution of sodium chloride, dried over with anhydrous magnesium sulfate and concentrated. The residue was purified on silica gel column chromatography (hexane:AcOEt=7:3) to give the present invention compound (320 mg) having the following physical data.

TLC: Rf 0.42 (hexane:AcOEt=2:1); MS (APCI): m/z 353 (M$^+$−1), 169, 156; NMR (CDCl$_3$) δ 8.15–8.08 (1 H, m), 7.59 (1 H, d, J=8.6Hz), 7.45–7.23 (5H, m), 7.02–6.80 (4H, m), 5.35 (1 H, s), 4.16–3.98 (3H, m), 3.40–3.30 (2H, m), 3.01–2.68 (5H, m).

EXAMPLE 1(1)

1-[2-(5-Hydroxy-1-naphthyl)ethylsulfinyl]-3-phenoxy-2RS-propanol

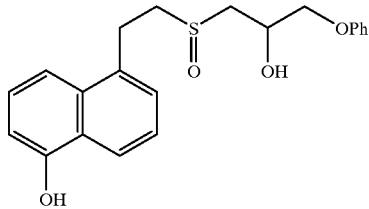

By using the compound prepared in Reference Example 27(1), the present invention compound having the following physical data was obtained by the same procedure as Example 1.

TLC: Rf 0.23 (hexane:AcOEt=1:1); MS (EI): m/z 370 (M$^+$).

EXAMPLE 1(2)

1-[2-(5-Hydroxy-1-naphthyl)ethylsulfonyl]-3-phenoxy-2RS-propanol

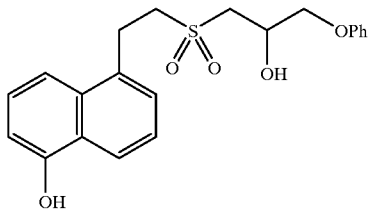

By using the compound prepared in Reference Example 28(1), the present invention compound having the following physical data was obtained by the same procedure as Example 1.

TLC: Rf 0.26 (hexane:AcOEt=1:1); MS (EI): m/z 386 (M$^+$).

EXAMPLE 1(3)

1-[2-(5-Hydroxy-1-naphthyl)ethylthio]-3-phenoxy-2R-propanol

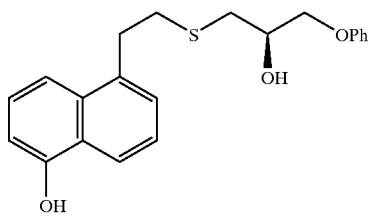

By using the compound prepared in Reference Example 24(1), the present invention compound having the following physical data was obtained by the same procedure as Example 1.

TLC: Rf 0.42 (hexane:AcOEt=2:1); MS (APCI): m/z 353 (M$^+$−1), 169, 156.

EXAMPLE 1(4)

1-[2-(5-Hydroxy-1-naphthyl)ethylthio]-3-phenoxy-2S-propanol

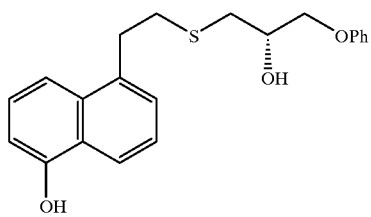

By using the compound prepared in Reference Example 24(2), the present invention compound having the following physical data was obtained by the same procedure as Example 1.

TLC: RF 0.42 (hexane:AcOEt=2:1); MS (APCI): m/z 353 (M$^+$−1), 169, 156.

EXAMPLE 1(5)

1-(5-Hydroxy-1-naphthyl)methylthio-3-phenoxy-2RS-propanol

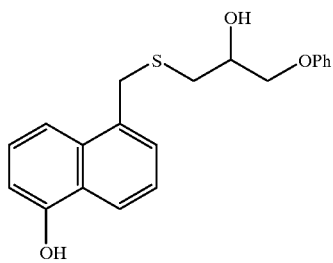

By using the compound prepared in Reference Example 24(3), the present invention compound having the following physical data was obtained by the same procedure as Example 1.

TLC: Rf 0.40 (hexane:AcOEt=1:1); MS (EI): m/z 340 (M$^+$).

EXAMPLE 1(6)

1-(5-Hydroxy-1-naphthyl)methylsulfinyl-3-phenoxy-2RS-propanol

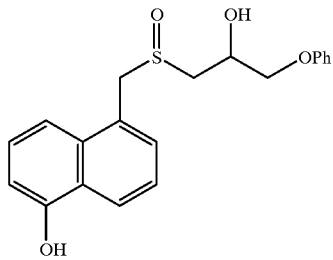

By using the compound prepared in Reference Example 27, the present invention compound having the following physical data was obtained by the same procedure as Example 1.

TLC: Rf 0.42 (AcOEt); MS (EI): m/z 356 (M$^+$).

EXAMPLE 1(7)

1-(5-Hydroxy-1-naphthyl)methylsulfonyl-3-phenoxy-2RS-propanol

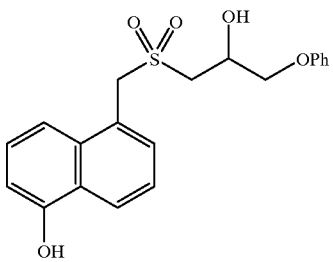

By using the compound prepared in Reference Example 28, the present invention compound having the following physical data was obtained by the same procedure as Example 1.

TLC: Rf 0.24 (hexane: AcOEt=1:1); MS (EI): m/z 372 (M$^+$).

EXAMPLE 1(8)

2-[3-(5-Hydroxy-1-naphthyl)propylthio]-1-phenyl-1RS-ethanol

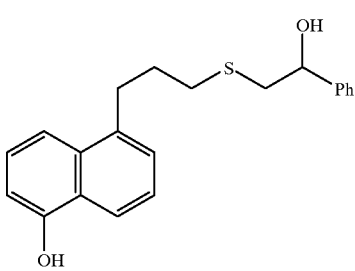

By using the compound prepared in Reference Example 25, the present invention compound having the following physical data was obtained by the same procedure as Example 1.

TLC: Rf 0.33(hexane:AcOEt=2:1); MS (EI): m/z 338 (M$^+$).

EXAMPLE 1(9)

2-[3-(5-Hydroxy-1-naphthyl)propylsulfinyl]-1-phenyl-1RS-ethanol

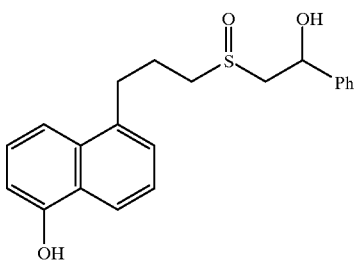

By using the compound prepared in Reference Example 27(2), the present invention compound having the following physical data was obtained by the same procedure as Example 1.

TLC: Rf 0.34 (AcOEt); MS (EI): m/z 354 (M$^+$).

EXAMPLE 1(10)

2-[3-(5-Hydroxy-1-naphthyl)propylsulfonyl]-1-phenyl-1RS-ethanol

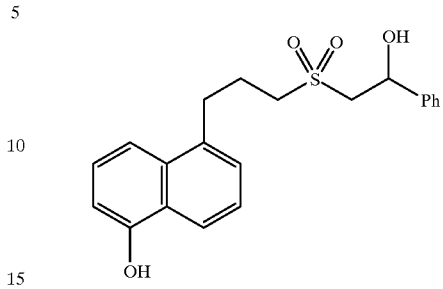

By using the compound prepared in Reference Example 28(2), the present invention compound having the following physical data was obtained by the same procedure as Example 1.

TLC: Rf 0.10 (hexane:AcOEt=2:1); MS (EI): m/z 370 (M$^+$).

EXAMPLE 1(11)

1-(5-Hydroxy-1-naphthyl)thio-3-phenoxy-2RS-propanol

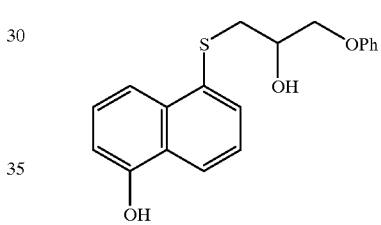

By using the compound prepared in Reference Example 29, the present invention compound having the following physical data was obtained by the same procedure as Example 1.

TLC: Rf 0.40 (hexane:AcOEt=1:1); MS (EI): m/z 326 (M$^+$).

EXAMPLE 1(12)

1-(5-Hydroxy-1-naphthyl)sulfinyl-3-phenoxy-2RS-propanol

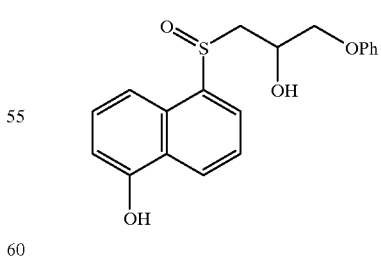

By using the compound prepared in Reference Example 29(1), the present invention compound having the following physical data was obtained by the same procedure as Example 1.

TLC: Rf 0.24(hexane:AcOEt=1:1); MS (EI): m/z 342 (M$^+$).

EXAMPLE 1(13)

1-(5-Hydroxy-1-naphthyl)sulfonyl-3-phenoxy-2RS-propanol

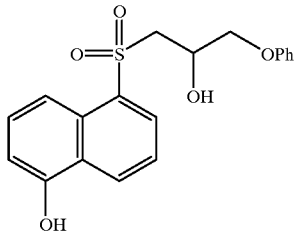

By using the compound prepared in Reference Example 29(2), the present invention compound having the following physical data was obtained by the same procedure as Example 1.

TLC: Rf 0.26 (hexane:AcOEt=1:1); MS (EI): m/z 358 (M$^+$).

EXAMPLE 2

2-{5-[2-(2 RS -Hydroxy-3-phenoxypropylthio)ethyl]-1-naphthyloxy}acetic Acid Methyl Ester

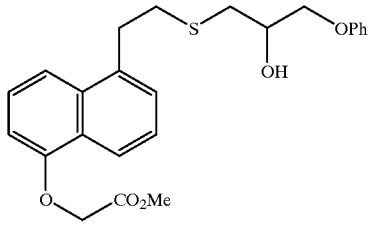

To a solution of the compound prepared in Example 1 (4.54 g) in acetone (25 ml), potassium carbonate (2.66 g) and bromoacetic acid methyl ester (1.46 ml) were added. The mixture was stirred overnight. Ethyl acetate (25 ml) was added to the reaction mixture. The mixture was filtrated. The filtrate was concentrated. The residue was purified on silica gel column chromatography (hexane:AcOEt=7:3) to give the present invention compound (4.95 g) having the following physical data.

TLC: Rf 0.46 (AcOEt:benzene=3:17); MS (APCI): m/z 409 (M$^+$+1-H$_2$O).

EXAMPLE 2(1)

2-{5-[2-(2RS-Hydroxy-3-phenoxypropylsulfinyl)ethyl]-1-naphthyloxy}acetic Acid Methyl Ester

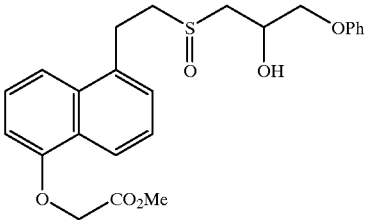

By using the compound prepared in Example 1(1), the present invention compound having the following physical data was obtained by the same procedure as Example 2.

TLC: Rf 0.36 (hexane:AcOEt=1:1); MS (EI): m/z 442 (M$^+$).

EXAMPLE 2(2)

2-{5-[2-(2RS-Hydroxy-3-phenoxypropylsulfonyl)ethyl]-1-naphthyloxy}acetic Acid Methyl Ester

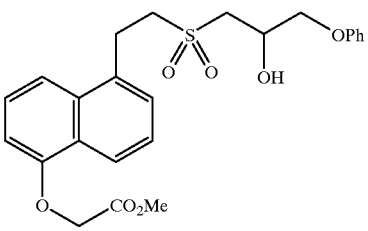

By using the compound prepared in Example 1(2), the present invention compound having the following physical data was obtained by the same procedure as Example 2.

TLC: Rf 0.40 (hexane:AcOEt=1:1); MS (EI): m/z 458 (M$^+$).

EXAMPLE 2(3)

2-{5-(2-(2R-Hydroxy-3-phenoxypropylthio)ethyl]-1-naphthyloxy}acetic Acid Methyl Ester

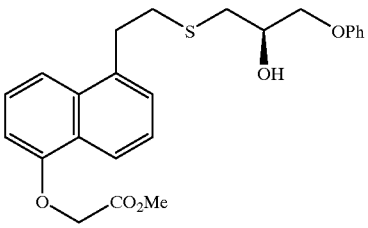

By using the compound prepared in Example 1(3), the present invention compound having the following physical data was obtained by the same procedure as Example 2.

TLC: Rf 0.46 (AcOEt:benzene=3:17); MS (APCI): m/z 409 (M$^+$+1-H$_2$O).

EXAMPLE 2(4)

2-{5-[2-(2S-Hydroxy-3-phenoxypropylthio)ethyl]-1-naphthyloxy}acetic Acid Methyl Ester

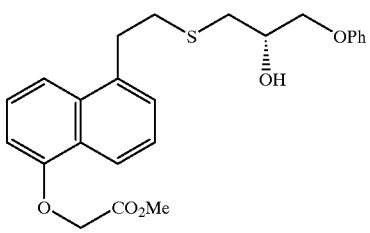

By using the compound prepared in Example 1(4), the present invention compound having the following physical data was obtained by the same procedure as Example 2.

TLC: Rf 0.46 (AcOEt:benzene=3:17); MS (APCI): m/z 409 ($M^+$+1−$H_2O$).

EXAMPLE 2(5)

2-[5-(2RS-Hydroxy-3-phenoxypropylthio)methyl-1-naphthyloxy]acetic Acid Methyl Ester

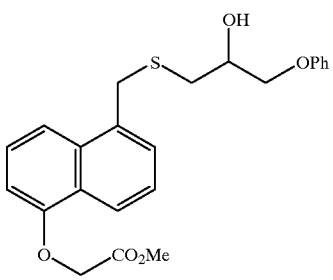

By using the compound prepared in Example 1(5), the present invention compound having the following physical data was obtained by the same procedure as Example 2.

TLC: Rf 0.30 (AcOEt:benzene=3:17); MS (EI): m/z 412 ($M^+$).

EXAMPLE 2(6)

2-[5-(2RS-Hydroxy-3-phenoxypropylsulfinyl)methyl-1-naphthyloxy]acetic Acid Methyl Ester

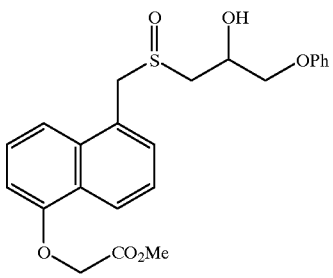

By using the compound prepared in Example 1(6), the present invention compound having the following physical data was obtained by the same procedure as Example 2.

TLC: Rf 0.22 (AcOEt); MS (EI): m/z 412 ($M^+$−O).

EXAMPLE 2(7)

2-[5-(2RS-Hydroxy-3-phenoxypropylsulfonyl)methyl-1-naphthyloxy]acetic Acid Methyl Ester

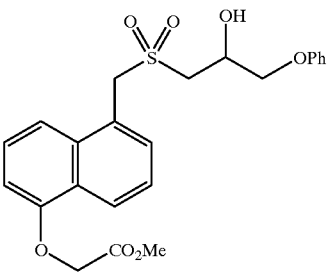

By using the compound prepared in Example 1(7), the present invention compound having the following physical data was obtained by the same procedure as Example 2.

TLC: RF 0.18 (AcOEt:benzene=1:4); MS (EI): m/z 444 ($M^+$).

EXAMPLE 2(8)

2-{5-[3-(2RS-Hydroxy-2-phenylethylthio)propyl]-1-naphthyloxy}acetic Acid Methyl Ester

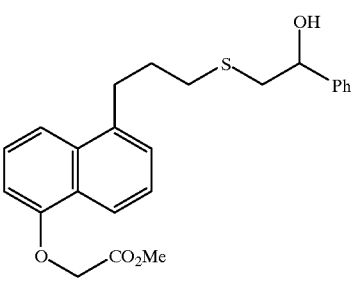

By using the compound prepared in Example 1(8), the present invention compound having the following physical data was obtained by the same procedure as Example 2.

TLC: Rf 0.35(hexane:AcOEt=2:1); MS (EI): m/z 410 ($M^+$).

EXAMPLE 2(9)

2-{5-[3-(2RS-Hydroxy-2-phenylethylsulfinyl)propyl]-1-naphthyloxy}acetic Acid Methyl Ester

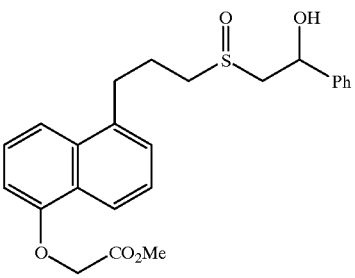

By using the compound prepared in Example 1(9), the present invention compound having the following physical data was obtained by the same procedure as Example 2.

TLC: Rf 0.36 (AcOEt); MS (EI): m/z 426 ($M^+$).

EXAMPLE 2(10)

2-{5-[3-(2RS-Hydroxy-2-phenylethylsulfonyl)propyl]-1-naphthyloxy}acetic Acid Methyl Ester

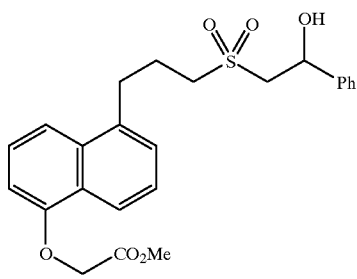

By using the compound prepared in Example 1(10), the present invention compound having the following physical data was obtained by the same procedure as Example 2.

TLC: Rf 0.10 (hexane:AcOEt=2:1); MS (EI): m/z 442 (M$^+$).

EXAMPLE 2(11)

2-[5-(2RS-Hydroxy-3-phenoxypropylthio)-1-naphthyloxy]acetic Acid Methyl Ester

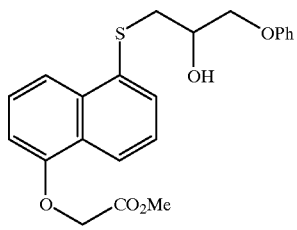

By using the compound prepared in Example 1(11), the present invention compound having the following physical data was obtained by the same procedure as Example 2.

TLC: Rf 0.42 (hexane: AcOEt=1:1); MS (EI): m/z 398 (M$^+$).

EXAMPLE 2(12)

2-[5-(2RS-Hydroxy-3-phenoxypropylsulfinyl)-1-naphthyloxy]acetic Acid Methyl Ester

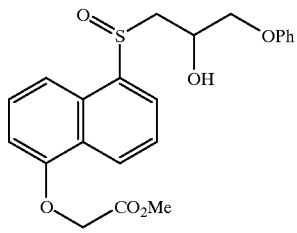

By using the compound prepared in Example 1(12), the present invention compound having the following physical data was obtained by the same procedure as Example 2.

TLC: Rf 0.29 (hexane:AcOEt=1:1); MS (EI): m/z 414 (M$^+$).

EXAMPLE 2(13)

2-[5-(2RS-Hydroxy-3-phenoxypropylsulfonyl)-1-naphthyloxy]acetic Acid Methyl Ester

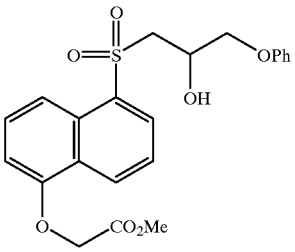

By using the compound prepared in Example 1(13), the present invention compound having the following physical data was obtained by the same procedure as Example 2.

TLC: Rf 0.31 (hexane:AcOEt=1:1); MS (EI): m/z 430 (M$^+$).

EXAMPLE 3

2-{5-[2-(2RS-Hydroxy-3-phenoxypropylthio)ethyl]-1-naphthyloxy}acetic Acid

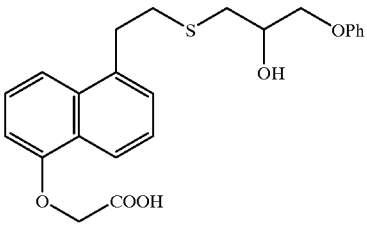

To a solution of the compound prepared in Example 2 (4.80 g) in dimethoxyethane-methanol (30 ml–1 5 ml), 2N aqueous solution of sodium hydroxide (8 ml) was added at 0° C. The mixture was stirred for 1 hour at 0° C. 2N aqueous solution of hydrochloric acid (8.5 ml) was added to the reaction solution in order to be neutralized. The mixture was extracted with ethyl acetate. The organic layer was washed with a saturated aqueous solution of sodium chloride, dried over with anhydrous magnesium sulfate and concentrated. The residue was recrystalized from AcOEt-hexane to give the present invention compound (4.07 g) having the following physical data.

TLC: Rf 0.22 (CHCl$_3$:MeOH=15:1); MS (EI): m/z 412 (M$^+$); NMR (DMSO-d6): δ 8.25 (1H, d, J=8 Hz), 7.71 (1H, d, J=8 Hz), 7.50–7.16 (5H, m), 7.02–6.69 (4H, m), 4.78 (2H, s), 4.24–4.38 (7H, m), 2.90–2.53 (2H, m).

EXAMPLE 3(1)

2-{5-[2-(2RS-Hydroxy-3-phenoxypropylsulfinyl)ethyl]-1-naphthyloxy}acetic Acid

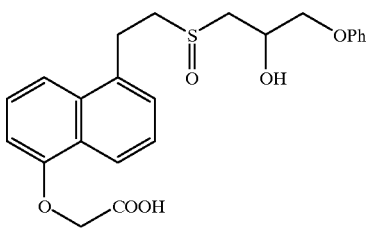

By using the compound prepared in Example 2(1), the present invention compound having the following physical data was obtained by the same procedure as Example 3.

TLC: Rf 0.26 (CHCl$_3$:MeOH=15:1); MS (EI): m/z 428 (M$^+$); NMR (DMSO-d6): δ 8.42 (1H, d, J=8 Hz), 7.73 (1H, d, J=8 Hz), 7.60–7.21 (5H, m), 6.98–6.82 (4H, m), 4.81 (2H, s), 4.76–4.38 (6H, m), 4.06–3.97 (1H, m), 2.90–2.53 (2H, m).

EXAMPLE 3(2)

2-{5-[2-(2RS-Hydroxy-3-phenoxypropylsulfonyl)ethyl]-1-naphthyloxy}acetic Acid

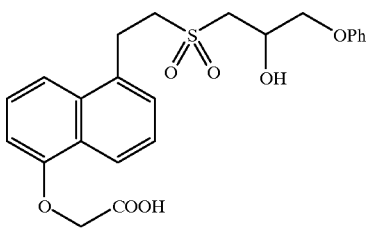

By using the compound prepared in Example 2(2), the present invention compound having the following physical data was obtained by the same procedure as Example 3.

TLC: Rf 0.18(CHCl$_3$:MeOH=15:1); MS (EI): m/z 444 (M$^+$), 404, 167, 115; NMR (DMSO-d6): δ 8.22 (1H, d, J=8 Hz), 7.59 (1H, d, J=8 Hz), 7.42–7.14 (7H, m), 6.89–6.66 (2H, m), 4.78 (2H, s), 4.24–3.88 (7H, m), 2.90–2.53 (2H, m).

EXAMPLE 3(3)

2-{5-[2-(2R-Hydroxy-3-phenoxypropylthio)ethyl]-1-naphthyloxy}acetic Acid

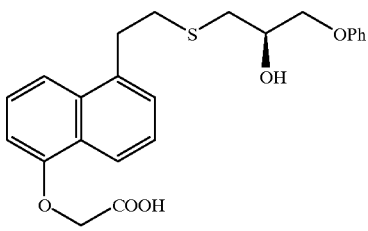

By using the compound prepared in Example 2(3), the present invention compound having the following physical data was obtained by the same procedure as Example 3.

TLC: Rf 0.26 (CHCl$_3$:MeOH:AcOH=19 1:0.1); MS (APCI): m/z 411 (M$^+$−1), 353; m.p. 114.0–115.5° C.; NMR (DMSO-d6): δ 8.20–8.10 (1H, m), 7.64 (1H, d, J=8.6 Hz), 7.50–7.35 (3H, m), 7.35–7.20 (2H, m), 7.00–6.85 (4H, m), 5.25 (1H, br.), 4.87 (2H, s), 3.96 (3H, m), 3.37–3.22 (2H, m), 2.98–2.65 (4H, m).

EXAMPLE 3(4)

2-{5-[2-(2S-Hydroxy-3-phenoxypropylthio)ethyl]-1-naphthyloxy}acetic Acid

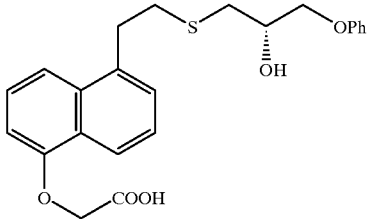

By using the compound prepared in Example 2(4), the present invention compound having the following physical data was obtained by the same procedure as Example 3.

TLC: Rf 0.26(CHCl$_3$:MeOH:AcOH=19:1:0.1); MS (APCI): m/z 411 (M$^+$−1), 353; m.p. 114.0–115.5° C.; NMR (DMSO-d6): δ 8.20–8.1 0 (1H, m), 7.64 (1H. d, J=8.6 Hz), 7.50–7.35 (3H, m), 7.35–7.20 (2H, m), 7.00–6.85 (4H, m), 5.25 (1H, br.), 4.87 (2H, s), 3.96 (3H, m), 3.37–3.22 (2H, m), 2.98–2.65 (4H, m).

EXAMPLE 3(5)

2-[5-(2RS-Hydroxy-3-phenoxypropylthio)methyl-1-naphthyloxy]acetic Acid

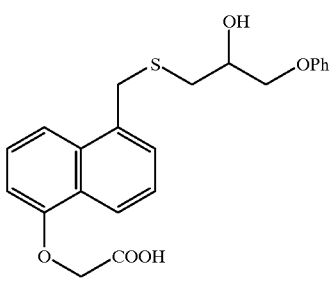

By using the compound prepared in Example 2(5), the present invention compound having the following physical data was obtained by the same procedure as Example 3.

TLC: Rf 0.21 (MeOH:CHCl$_3$=3:7); MS (EI): m/z 398 (M$^+$); m.p. 105–107° C.; NMR (DMSO-d6+CDCl$_3$): δ 8.32 (1H, d, J=8 Hz), 7.75 (1H, d, J=8 Hz), 7.58–7.14 (5H, m), 7.00–6.70 (4H, m), 4.78 (2H, s, CH$_2$COO), 4.60–3.80 (7H, m), 2.87–2.60 (2H, m).

EXAMPLE 3(6)

2-[5-(2RS-Hydroxy-3-phenoxypropylsulfinyl)methyl-1-naphthyloxy]acetic Acid

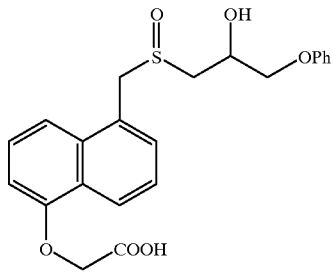

By using the compound prepared in Example 2(6), the present invention compound having the following physical data was obtained by the same procedure as Example 3.

TLC: Rf 0.16 (MeOH:CHCl$_3$=3:7); MS (EI): m/z 414 (M$^+$), 396 (M$^+$–H$_2$O) NMR (CD$_3$OD+CDCl$_3$): δ 8.45 (1H, d, J=8 Hz), 7.73 (1H, d, J=8 Hz), 7.62–7.38 (3H, m), 7.34–7.19 (2H, m), 7.00–6.82 (4H, m), 5.05–4.40 (5H, m), 4.08–3.96 (2H, m), 3.44–3.05 (2H, m).

EXAMPLE 3(7)

2-[5-(2RS-Hydroxy-3-phenoxypropylsulfonyl)methyl-1-naphthyloxy]acetic Acid

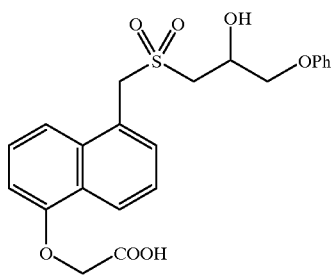

By using the compound prepared in Example 2(7), the present invention compound having the following physical data was obtained by the same procedure as Example 3.

TLC: RF 0.17 (MeOH:CH$_2$Cl$_2$=1:5); MS (EI): m/z 430 (M$^+$); m.p. 186–190° C.; NMR (CD$_3$OD+CDCl$_3$): δ 8.48 (1H, d, J=8 Hz), 7.82 (1H, d, J=8 Hz), 7.70 (1H, d, J=7 Hz), 7.63–7.40 (2H, m), 7.40–7.22 (2H, m), 7.10–6.77 (4H, m), 5.02 (1H, d, J=15 Hz), 4.92 (1H, d, J=15 Hz), 4.81 (2H, s), 4.75–4.54 (1H, m), 4.20–3.70 (2H, m), 3.40–3.33 (1H, m), 3.33–3.15 (1H, m).

EXAMPLE 3(8)

2-{5-[3-(2RS-Hydroxy-2-phenylethylthio)propyl]-1-naphthyloxy}acetic Acid

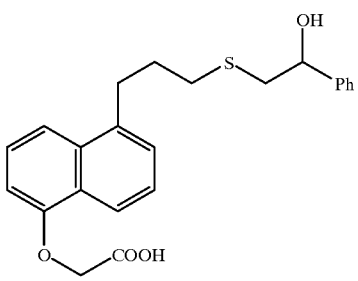

By using the compound prepared in Example 2(8), the present invention compound having the following physical data was obtained by the same procedure as Example 3.

TLC: Rf 0.13 (MeOH:CH$_2$Cl$_2$=1:5); MS (EI): m/z 396 (M$^+$), 290, 276; NMR (DMSO-d6): δ 14.00–12.40 (1H, br), 8.12 (1H, d, J=8 Hz), 7.65 (1H, d, J=8 Hz), 7.50–7.16 (8H, m), 6.88 (1H, d, J=7 Hz), 5.47 (1H, m), 4.87 (2H, s), 4.63 (1H, m), 3.06 (2H, m), 2.75 (2H, m), 2.60–2.40 (2H, m), 1.87 (2H, m).

EXAMPLE 3(9)

2-[5-(2RS-Hydroxy-3-phenoxypropylthio)-1-naphthyloxy]acetic Acid

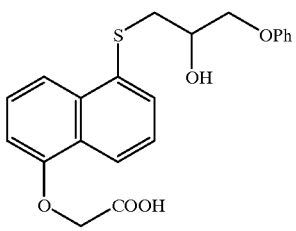

By using the compound prepared in Example 2(11), the present invention compound having the following physical data was obtained by the same procedure as Example 3.

TLC: Rf 0.25 (MeOH:CH$_2$Cl$_2$=1:5); MS (EI): m/z 384 (M$^+$); NMR (DMSO-d6): δ 8.68 (1H, d, J=4 Hz), 8.43 (1H, d, J=8 Hz), 8.40 (1H, d, J=8 Hz), 7.81 (1H, t, J=4 Hz), 7.66 (1H, d, J=4 Hz), 7.61–7.28 (3H, m), 7.01–6.90 (3H, m), 4.92–4.79 (1H, m), 4.87 (2H, s), 4.21–3.83 (4H, m).

EXAMPLE 3(10)

2-[5-(2RS-Hydroxy-3-phenoxypropylsulfinyl)-1-naphthyloxy]acetic Acid

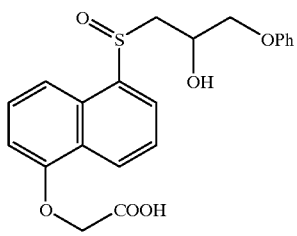

By using the compound prepared in Example 2(12), the present invention compound having the following physical data was obtained by the same procedure as Example 3.

TLC: Rf 0.29 (MeOH:$CH_2Cl_2$=1:5); MS (EI): m/z 401 ($M^+$+1); NMR (DMSO-d6): δ 8.68 (1H, d, J=4 Hz), 8.43 (1H, d, J=8 Hz), 8.40 (1H, d, J=8 Hz), 7.81 (1H, t, J=4 Hz), 7.66 (1H, d, J=4 Hz), 7.61–7.28 (3H, m), 7.01–6.90 (3H, m), 4.92–4.79 (1H, m), 4.87 (2H, s), 4.21–3.83 (4H, m).

EXAMPLE 3(11)

2-[5-(2RS-Hydroxy-3-phenoxypropylsulfonyl)-1-naphthyloxy]acetic Acid

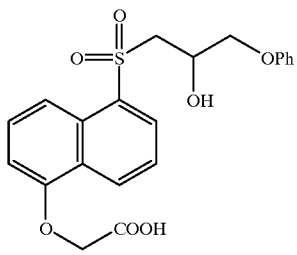

By using the compound prepared in Example 2(13), the present invention compound having the following physical data was obtained by the same procedure as Example 3.

TLC: Rf 0.22 (MeOH:$CH_2Cl_2$=1:5); MS (EI): m/z 416 ($M^+$); NMR (DMSO-d6): δ 8.68 (1H, d, J=4 Hz), 8.43 (1H, d, J=8 Hz), 8.40 (1H, d, J=8 Hz), 7.81 (1H, t, J=4 Hz), 7.66 (1H, d, J=4 Hz), 7.61–7.28 (3H, m), 7.01–6.90 (3H, m), 4.92–4.79 (1H, m), 4.87 (2H, s), 4.21–3.83 (4H, m).

EXAMPLE 4

2-[5-(3-Styrylsulfonylpropyl)-1-naphthyloxy]acetic Acid Methyl Ester

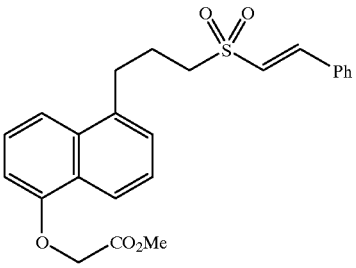

To a solution of the compound prepared in Example 2(10) (96 ml) in methylene chloride (10 ml), triethylamine (0.091 ml) and mesylchloride (37.3 ml) were added at 0° C. The mixture was heated to room temperature and stirred for 30 minutes. Water was added to the reaction mixture. The mixture was extracted with ethyl acetate. The organic layer was washed with water and a saturated aqueous solution of sodium chloride, dried over with anhydrous sodium sulfate and concentrated. The residue was purified on silica gel column chromatography (hexane:AcOEt=2:1) to give the present invention compound (94 mg) having the following physical data.

TLC: Rf 0.18 (hexane:AcOEt=2:1); MS (EI): m/z 424 ($M^+$).

EXAMPLE 4(1)

2-[5-(3-Styrylsulfinylpropyl)-1-naphthyloxy]acetic Acid Methyl Ester

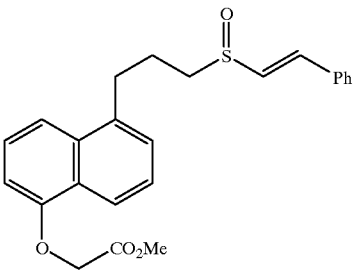

By using the compound prepared in Example 2(9), the present invention compound having the following physical data was obtained by the same procedure as Example 4.

TLC: Rf 0.50 (benzene:AcOEt=1:2); MS (EI): m/z 408 ($M^+$).

EXAMPLE 5

2-[5-(3-Styrylsulfinylpropyl)-1-naphthyloxy]acetic Acid

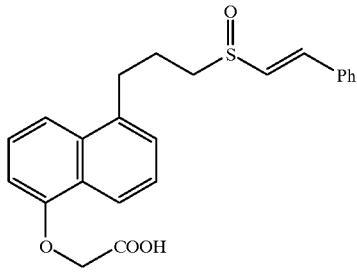

By using the compound prepared in Example 4(1), the present invention compound having the following physical data was obtained by the same procedure as Example 3.

TLC: Rf 0.23 (MeOH:$CH_2Cl_2$=1:5); MS (EI): m/z 394 ($M^+$), 378, 320, 242, 183; NMR ($CDCl_3$—$CD_3OD$): δ 8.38 (0.13H, dd, J=8, 2 Hz), 8.30 (0.87H, d, J=8 Hz), 7.64–7.20 (10H, m), 6.82–6.67 (1.87H, m), 6.61 (0.13H, d, J=8 Hz), 4.77 (1.74H, s), 4.75 (0.26H, s), 3.30–3.03 (4H, m), 2.40–2.15 (2H, m).

EXAMPLE 5(1)

2-[5-(3-Styrylsulfonylpropyl)-1-naphthyloxy]acetic Acid

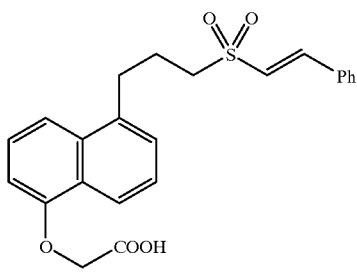

By using the compound prepared in Example 4, the present invention compound having the following physical data was obtained by the same procedure as Example 5.

TLC: Rf 0.26 (MeOH:$CH_2Cl_2$=1:5); MS (EI): m/z 410 ($M^+$), 378, 352, 276, 253, 242, 215; NMR ($CDCl_3$): δ 8.26 (1H, d, J=8 Hz), 7.57 (1H, d, J=9 Hz), 7.50–7.13 (9H, m), 7.13–6.40 (1H, br), 6.79 (1H, d, J=15 Hz), 6.65 (1H, d, J=7 Hz), 4.75 (2H, s), 3.19 (2H, t, J=8 Hz), 2.90 (2H, t, J=8 Hz), 2.22 (2H, m).

EXAMPLE 6

1-[2-(5-Hydroxy-1-naphthyl)ethylthio]-3-(4-chlorophenoxy)-2RS-propanol

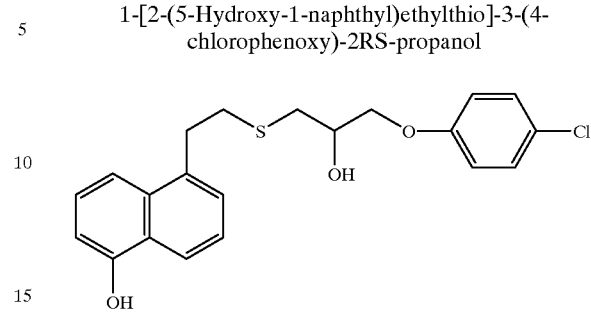

By using 4-chlorophenol instead of phenol in Reference Example 2, the present invention compound having the following physical data was obtained by the same procedure as Reference Example 2→Reference Example 3→Reference Example 4→Reference Example 5→Reference Example 24→Example 1.

TLC: Rf 0.34 (hexane: AcOEt=2:1); MS (APCI): m/z 389, 387 (1:3, M–$H^+$); NMR ($CDCl_3$): δ 8.12 (1H, d, J=7.4 Hz), 7.58 (1H, d, J=8.4 Hz), 7.38 (3H, m), 7.22 (2H, d, J=6.8 Hz), 6.82 (2H, d, J=6.8 Hz), 6.82 (1H, m), 5.32 (1H, s), 4.07 (1H, m), 3.96 (2H, m), 3.35 (2H, m), 2.96 (2H, m), 2.86 (1H, dd, J=14, 5 Hz), 2.74 (1H, dd, J=14, 6.8 Hz), 2.66 (1H, d, J=3.4 Hz).

EXAMPLE 6(1)

1-[2-(5-Hydroxy-1-naphthyl)ethylthio]-3-(4-methylphenoxy)-2RS-propanol

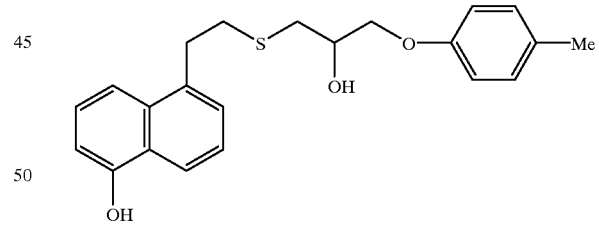

By using 4-methylphenol instead of phenol in Reference Example 2, the present invention compound having the following physical data was obtained by the same procedure as Example 6.

TLC: Rf 0.35 (hexane:AcOEt=2:1); NMR ($CDCl_3$): δ 8.11 (1H, d, J=8.4 Hz), 7.58 (1H, d, J=8.6 Hz), 7.37 (3H, m), 7.07 (2H, d, J=8 Hz), 6.82 (1H, d, J=7.4 Hz), 6.80 (2H, d, J=8 Hz), 5.39 (1H, s), 4.08 (1H, m), 4.00 (2H, m), 3.35 (2H, m), 2.95 (2H, m), 2.91 (1H, dd, J=13.6, 5.2 Hz), 2.46 (1H, dd, J=13.6, 6.8 Hz), 2.70 (1H, d, J=4 Hz), 2.29 (3H, s).

EXAMPLE 6(2)

1-[2-(5-Hydroxy-1-naphthyl)ethylthio]-3-(4-methoxyphenoxy)-2RS-propanol

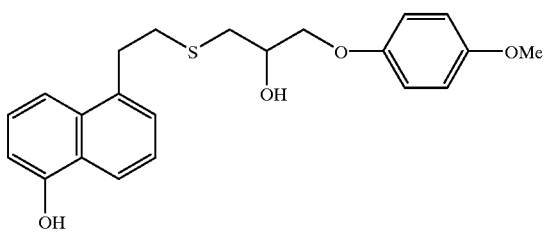

By using 4-metyhoxyphenol instead of phenol in Reference Example 2, the present invention compound having the following physical data was obtained by the same procedure as Example 6.

TLC: Rf 0.55 (hexane:AcOEt=2:1).

EXAMPLE 6(3)

1-[2-(5-Hydroxy-1-naphthyl)ethylthio]-3-diphenylmethoxy-2RS-propanol

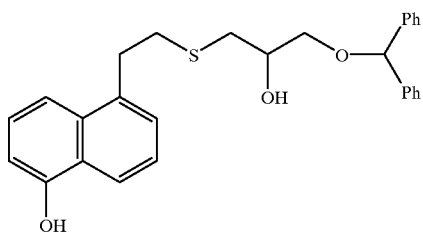

By using diphenylmethanol instead of phenol in Reference Example 2, the present invention compound having the following physical data was obtained by the same procedure as Example 6.

TLC: Rf 0.29 (hexane:AcOEt=2:1); NMR (CDCl$_3$): δ 8.11 (1H, m), 7.57 (1H, d, J=8.6 Hz), 7.34 (13H, m), 6.81 (1H, d, J=7.4 Hz), 5.43 (1H, s), 5.38 (1H, S), 3.96 (1H, m), 3.52 (2H, d, J=5.6 Hz), 3.31 (2H, m), 2.91 (2H, m), 2.80 (1H, dd, J=5.3, 13.6 Hz), 2.69 (1H, dd, J=7.2, 13.6 Hz), 2.67 (1H, d, J=4.3 Hz).

EXAMPLE 6(4)

1-[2-(5-Hydroxy-1-naphthyl)ethylthio]-3-[1-phenyl-1-(4-chlorophenyl)methoxyl-2RS-propanol

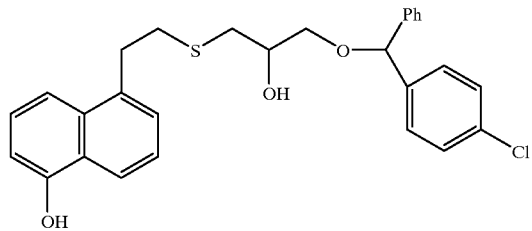

By using 1-phenyl-1-(4-chlorophenyl)methanol instead of phenol in Reference Example 2, the present invention compound having the following physical data was obtained by the same procedure as Example 6.

TLC: Rf 0.35 (hexane:AcOEt=2:1); NMR (CDCl$_3$): δ 8.12 (1H, d, J=9.1 Hz), 7.57 (1H, d, J=8.4 Hz), 7.33 (12H, m), 6.82 (1H, d, J=7.5 Hz), 5.40 (1H, m), 5.35 (1H, s), 3.94 (1H, m), 3.50 (2H, d, J=4.8 Hz), 3.32 (2H, m), 2.91 (2H, m), 2.73 (3H, m).

EXAMPLE 6(5)

1-[2-(5-Hydroxy-1-naphthyl)ethylthio]-3-phenylthio-2RS-propanol

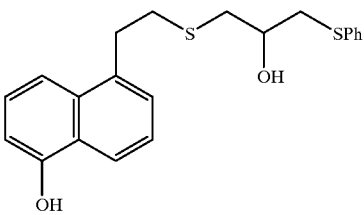

By using thiophenol instead of phenol in Reference Example 2, the present invention compound having the following physical data was obtained by the same procedure as Example 6.

TLC: Rf 0.41 (hexane:AcOEt=2:1).

EXAMPLE 6(6)

1-(5-Hydroxy-1-naphthyl)methylthio-3-diphenylmethoxy-2RS-propanol

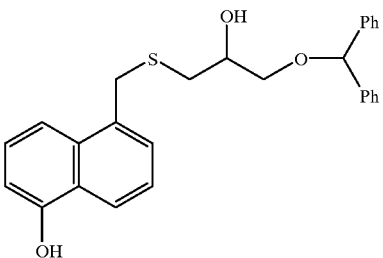

By using diphenylmethanol instead of phenol in Reference Example 2, the present invention compound having the following physical data was obtained by the same procedure as Reference Example 2→Reference Example 3→Reference Example 4→Reference Example 5→Reference Example 24(3)→Example 1.

TLC: Rf 0.17 (acetone:benzene=1:19); NMR (CDCl$_3$): δ 8.15 (1H, dd, J=3.0, 6.6 Hz), 7.69 (1H, d, J=8.6 Hz), 7.32 (13H, m), 6.82 (1H, d, J=7.3 Hz), 5.50 (1H, s), 5.35 (1H, s), 4.17 (2H, s), 3.94 (1H, m), 3.48 (1H, d, J=5.2 Hz), 2.55–2.77 (3H, m).

EXAMPLE 6(7)

1-(5-Hydroxy-1-naphthyl)methylthio-3-[1-phenyl-1-(4-chlorophenyl)methoxy]-2RS-propanol

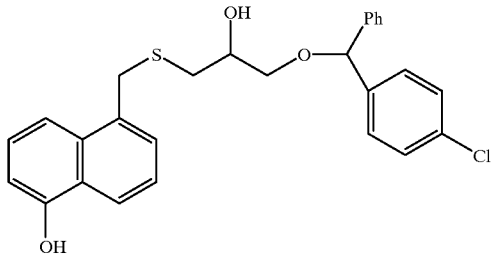

By using 1-phenyl-1-(4-chlorophenyl)methanol instead of phenol in Reference Example 2, the present invention compound having the following physical data was obtained by the same procedure as Example 6(6).

TLC: Rf 0.28 (hexane:AcOEt=2:1); NMR (CDCl$_3$): δ 8.16 (1H, dd, J=3.3, 6.3 Hz), 7.69 (1H, d, J=9.5 Hz), 7.29 (12H, m), 6.83 (1H, d, J=7.4 Hz), 5.41 (1H, s), 5.30 (1H, s), 4.17 (2H, s), 3.91 (1H, m), 3.45 (2H, d, J=5.2 Hz), 2.71 (1H, dd, J=5.2, 13.8 Hz), 2.63 (1H, dd, J=2.3, 7.2 Hz), 2.57 (1H, d, J=4.1 Hz).

REFERENCE EXAMPLE 30

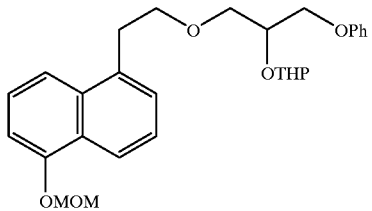

To the suspension of sodium hydride (42 mg) in DMF (1 ml), the solution of the compound prepared in Reference Example 15 (232 mg) in DMF (2 ml) was added at room temperature. To the mixture, THF (1 ml) and hexamethylphosphoramide (0.2 ml) were added at room temperature. The mixture was stirred for 30 minutes at room temperature and for 30 minutes at 40° C. To the mixture, the solution of the compound prepared in Reference Example 5 (406 mg) in DMF (2 ml) was added at room temperature. The mixture was stirred for 6 hours at 50° C. The reaction mixture was added to the aqueous solution of ammonium chloride, extracted with diethylether. The organic layer was washed with water and a saturated aqueous solution of sodium chloride, dried over with anhydrous sodium sulfate and concentrated. The residue was purified on silica gel column chromatography (hexane:AcOEt=87:13) to give the title compound (54.8 mg) having the following physical data.

TLC: Rf 0.37 (hexane:AcOEt=3:1); NMR (CDCl$_3$): δ 8.18 (1H, m), 7.68 (1H, d, J=8 Hz), 7.45–7.20 (5H, m), 7.09 (1H, d, J=8 Hz), 7.01–6.83 (3H, m), 5.39 (2H, s), 4.88–4.72 (1H, m), 4.25–3.26 (14H, m), 1.90–1.40 (6H, m).

REFERENCE EXAMPLE 31

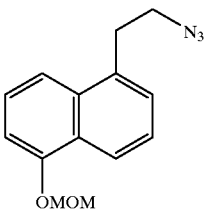

To the solution of the compound prepared in Reference Example 15 (5.0 g) in pyridine (15 ml), tosylchloride (6.28 9) was added at −20° C. The mixture was stirred for 2 hours at room temperature. The water (2 ml) was added dropwise to the mixture to decompose superfluous tosylchloride. To the mixture, 2N aqueous solution of hydrochloric acid (80 ml) was added. The mixture was extracted with ethyl acetate. The organic layer was washed with water and a saturated aqueous solution of sodium chloride, dried over with anhydrous sodium sulfate and concentrated to obtain crude tosyl compound. The tosyl compound was dissolved in acetone (25 ml). To the solution, sodium azide (2.8 g) and tetrabutylammonium bromide (400 mg) were added. The solution was refluxed over night. To the solution, sodium azide (2.8 g) was added. The solution was refluxed for 4 hours and cooled. The solvent was distilled off. The residue was diluted with ethyl acetate, washed with water and a saturated aqueous solution of sodium chloride, dried over with anhydrous sodium sulfate and concentrated to give the title compound (5.38 g) having the following physical data.

TLC: Rf 0.52 (hexane:AcOEt=7:3).

REFERENCE EXAMPLE 32

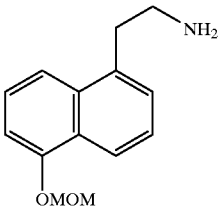

To the solution of the compound prepared in Reference Example 31 (1.56 g) in ethyl acetate (20 ml), 5% Pd—C (50 mg) was added. The mixture was stirred under an atmosphere of H$_2$ gas for 5 hours at room temperature. The solution was filtrated by Celite (Registered trade mark). The filtrate was concentrated and purified on silica gel column chromatography (MeOH:CHCl$_3$=3:97→MeOH:CHCl$_3$:propylamine=10:90:1) to give the title compound (1.02 g) having the following physical data.

TLC: Rf 0.17 (MeOH:CHCl$_3$=1:3); NMR (CDCl$_3$): δ 8.20 (1H, m), 7.69 (1H, d, J=8 Hz), 7.48–7.27 (3H, m), 7.11 (1H, d, J=8 Hz), 5.40 (2H, s), 3.53 (3H, s), 3.27–3.04 (4H, m), 1.35 (2H, brs, NH$_2$).

REFERENCE EXAMPLE 33

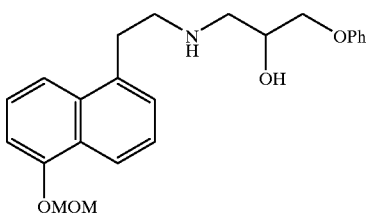

The solution of the compound prepared in Reference Example 32 (300 mg) and (±)-1,2-epoxy-3-phenoxypropane (195 mg) in iso-propanol (3 ml) was stirred for 2 days at room temperature. The reaction mixture was concentrated. The residue was purified on silica gel column chromatography (MeOH:CHCl$_3$=3:97→1:9) to give the title compound (270 mg) having the following physical data.

TLC: Rf 0.26 (MeOH:CHCl$_3$=1:9); NMR (CDCl$_3$): δ 88.22 (1H, m), 7.71 (1H, d, J=8 Hz), 7.47–7.21 (5H, m), 7.11(1H, d, J=8 Hz), 6.99–6.84 (3H, m), 5.40 (2H, s), 4.15–3.92 (3H, m), 3.55 (3H, s), 3.20 (2H, t, J=8 Hz), 3.13–2.76 (4H, m), 2.53 (2H, brs, OH & NH).

EXAMPLE 7

1-[2-(5-Hydroxy-1-naphthyl)ethoxy]-3-phenoxy-2RS-propanol

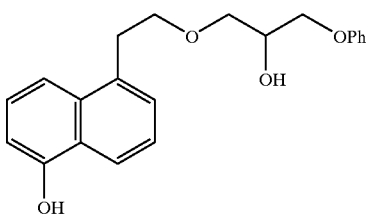

By using the compound prepared in Reference Example 30, the present invention compound having the following physical data was obtained by the same procedure as Example 1.

TLC: Rf 0.18 (hexane:AcOEt=2:1); NMR (CDCl$_3$): δ 8.11 (1H, m), 7.63 (1H, d, J=8 Hz), 7.46–7.21 (5H, m), 7.02–6.77 (4H, m), 5.49 (1H, s), 4.14 (1H, m), 3.96 (2H, d, J=5 Hz), 3.85 (2H, t, J=7 Hz), 3.63 (2H, m), 3.35 (2H, t, J=7 Hz), 2.48 (1H, d, J=4 Hz).

EXAMPLE 7(1)

1-[2-(5-Hydroxy-1-naphthyl)ethylamino]-3-phenoxy-2RS-propanol

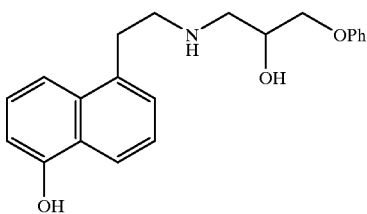

By using the compound prepared in Reference Example 33, the present invention compound having the following physical data was obtained by the same procedure as Example 1.

TLC: Rf 0.10 (MeOH:CHCl$_3$=1:9); NMR (CDCl$_3$+DMSO=1:4): δ 8.15 (1H, m), 7.54 (1H, d, J=8 Hz), 7.40–7.20 (5H, m), 7.00–6.84 (4H, m), 4.16–3.90 (3H, m), 3.80–2.50 (3H, br), 3.29 (2H, t, J=7 Hz), 3.14–2.75 (4H, m).

REFERENCE EXAMPLE 34

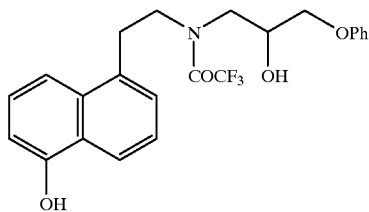

The mixture of the compound prepared in Example 7(1) (150 mg), trifluoroacetic acid ethyl ester (1 ml), triethylamine (0.5 ml) and ethanol (3 ml) was stirred for 5 hours at room temperature. The reaction mixture was concentrated and purified on silica gel column chromatography (hexane:AcOEt=5:2) to give the title compound (155 mg) having the following physical data.

TLC: Rf 0.53 (hexane:AcOEt=1:1); NMR (CDCl$_3$): rotational isomer, δ 8.21–8.10 (1H, m), 7.38 and 7.53 (combined 1H, each d, J=8 Hz), 7.48–7.20 (5H, m), 7.04–6.89 (4H, m), 5.53 (1H, brs), 4.40–3.27 (9H, m), 3.10 and 2.40 (combined 1H, each m).

EXAMPLE 8

2-{5-[2-(2 RS-Hydroxy-3-(4-chlorophenoxy)propylthio)ethyl]-1-naphthyloxy}acetic Acid Methyl Ester

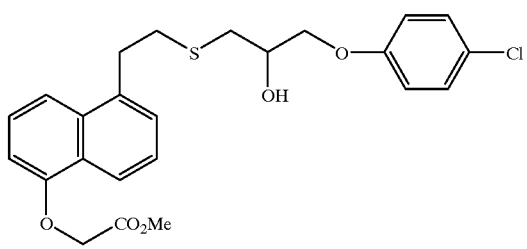

By using the compound prepared in Example 6, the present invention compound having the following physical data was obtained by the same procedure as Example 2.

TLC: Rf 0.27 (acetone:benzene=1:19); NMR (CDCl$_3$): δ 8.30 (1H, d, J=7.4 Hz), 7.62 (1H, d, J=8.6 Hz), 7.41 (3H, m), 7.22 (2H, d, J=9 Hz), 6.82 (2H, d, J=9 Hz), 6.72 (1H, d, J=7.4 Hz), 4.83 (2H, s), 4.06 (1H, m), 3.96 (2H, m), 3.04 (3H, s), 3.35 (2H, m), 2.95 (2H, m), 2.84 (1H, dd, J=14, 5 Hz), 2.73 (1H, dd, J=14, 7 Hz), 2.65 (1H, d, J=4 Hz).

EXAMPLE 8(1)

2-{5-[2-(2RS-Hydroxy-3-(4-methylphenoxy)propylthio)ethyl]-1-naphthyloxy}acetic Acid Methyl Ester

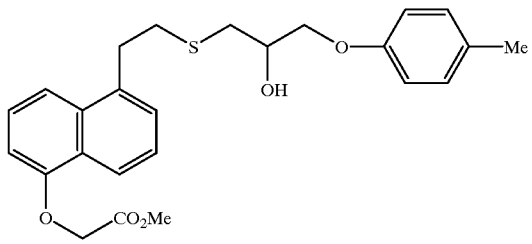

By using the compound prepared in Example 6(1), the present invention compound having the following physical data was obtained by the same procedure as Example 2.

TLC: Rf 0.37 (acetone:benzene=1:19); NMR (CDCl$_3$): δ 8.29 (1H, d, J=8 Hz), 7.64 (1H, d, J=8.8 Hz), 7.39 (3H, m), 7.07 (2H, d, J=8.8 Hz), 6.80 (2H, d, J=8.8 Hz), 6.72 (1H, d, J=8.8 Hz), 4.82 (2H, s), 4.08 (1H, m), 3.98 (2H, m), 3.83 (3H, s), 3.45 (2H, t, J=8.6 Hz), 2.94 (2H, t, J=8.6 Hz), 2.88 (2H, dd, J=14, 5.2 Hz), 7.75 (2H, dd, J=1 4, 6.8 Hz), 2.68 (1H, d, J=4 Hz), 2.29 (3H, s).

EXAMPLE 8(2)

2-{5-[2-(2RS-Hydroxy-3-(4-methoxyphenoxy)propylthio)ethyl]-1-naphthyloxy}acetic Acid Methyl Ester

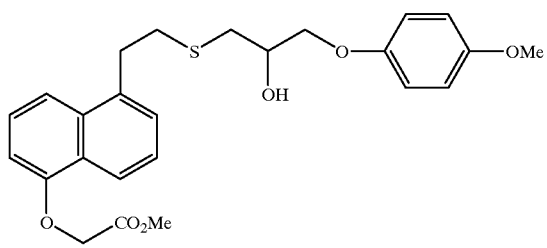

By using the compound prepared in Example 6(2), the present invention compound having the following physical data was obtained by the same procedure as Example 2.

TLC: Rf 0.41 (acetone:benzene=1:9); NMR (CDCl$_3$): δ 8.30 (1H, d, J=7.8 Hz), 7.63 (1H, d, J=8.6 Hz), 7.41 (3H, m), 6.83 (4H, s), 6.72 (1H, d, J=8.6 Hz), 4.82 (2H, s), 4.05 (1H, m), 3.96 (2H, m), 3.83 (3H, s), 3.77 (3H, s), 3.34 (2H, t, J=6.6 Hz), 2.93 (2H, t, J=6.6 Hz), 2.88 (1H, dd, J=14, 5 Hz), 2.75 (1H, dd, J=14, 7.2 Hz), 2.69 (1H, d, J=4 Hz).

EXAMPLE 8(3)

2-{5-[2-(2RS-Hydroxy-3-diphenylmethoxypropylthio)ethyl]-1-naphthyloxy}acetic Acid Methyl Ester

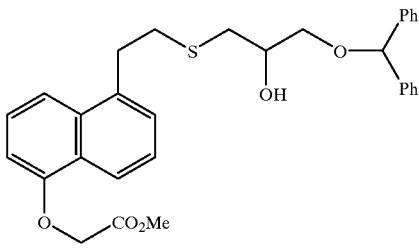

By using the compound prepared in Example 6(3), the present invention compound having the following physical data was obtained by the same procedure as Example 2.

TLC: Rf 0.33 (acetone:benzene=1:19); NMR (CDCl$_3$): δ 8.29 (1H, m), 7.62 (1H, d, J=8.6 Hz), 7.33 (13H, m), 6.72 (1H, d, J=7.7 Hz), 5.39 (1H, s), 4.82 (2H, s), 3.95 (1H, m), 3.83 (3H, s), 3.53 (2H, d, J=5.7 Hz), 2.90 (2H, m), 2.79 (1H, dd, J=5.3, 13.6 Hz), 2.69 (1H, dd, J=7.2, 13.6 Hz), 2.63 (1H, d, J=2.8 Hz).

EXAMPLE 8(4)

2-{5-[2-(2RS-Hydroxy-3-(1-phenyl-1-(4-chlorophenyl)methoxy)propylthio)ethyl]-1-naphthyloxy}acetic Acid Methyl Ester

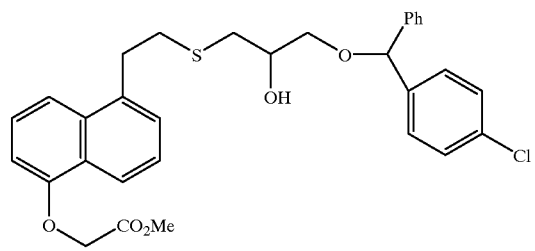

By using the compound prepared in Example 6(4), the present invention compound having the following physical data was obtained by the same procedure as Example 2.

TLC: Rf 0.26 (acetone:benzene=1:19); NMR (CDCl$_3$): δ 8.29 (1H, d, J=8.1 Hz), 7.62 (1H, d, J=8.5 Hz), 7.33 (12H, m), 6.72 (1H, d, J=7.6 Hz), 5.35 (1H, s), 4.82 (2H, s), 3.93 (1H, m), 3.83 (3H, s), 3.50 (1H, d, J=4.8 Hz), 3.32 (2H, m), 2.90 (2H, m), 2.76 (2H, m), 2.60 (1H, d, J=4.3 Hz).

EXAMPLE 8(5)

2-{5-[2-(2RS-Hydroxy-3-phenylthiopropylthio)ethyl]-1-naphthyloxy}acetic Acid Methyl Ester

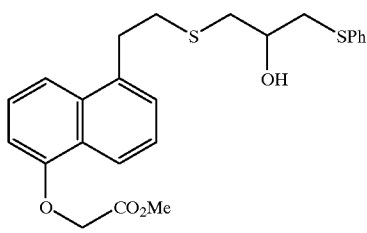

By using the compound prepared in Example 6(5), the present invention compound having the following physical data was obtained by the same procedure as Example 2.

TLC: Rf 0.33 (acetone:benzene=1:19).

EXAMPLE 8(6)

2-[5-(2RS-Hydroxy-3-diphenylmethoxypropylthio)methyl-1-naphthyloxy]acetic Acid Methyl Ester

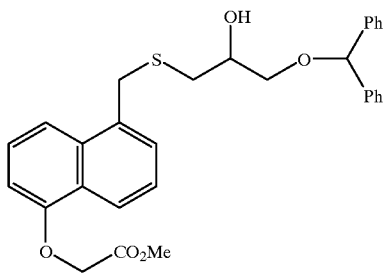

By using the compound prepared in Example 6(6), the present invention compound having the following physical data was obtained by the same procedure as Example 2.

TLC: Rf 0.33 (acetone:benzene=1: 19); NMR (CDCl$_3$): δ 8.33 (1H, m), 7.75 (1H, d, J=8.6Hz), 7.33 (13H, m), 6.74 (1H, d, J=7.7 Hz), 5.35 (1H, s), 4.82 (2H, s), 4.18 (2H, s), 3.94 (1H, m), 3.83 (3H, s), 3.48 (2H, d, J=5.2 Hz), 2.71 (1H, dd, J=5.3, 13.9 Hz), 2.59 (1H, dd, J=7.2, 13.9 Hz), 2.58 (1H, d, J=4.1 Hz).

EXAMPLE 8(7)

2-{5-[2RS-Hydroxy-3-(1-phenyl-1-(4-chlorophenyl)methoxy)propylthio]methyl-1-naphthyloxy}acetic Acid Methyl Ester

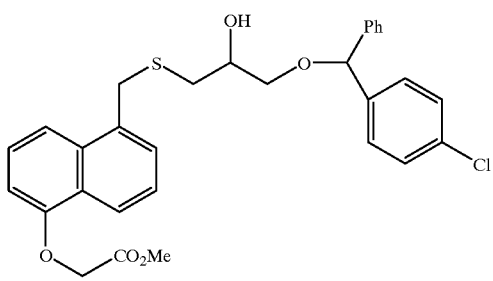

By using the compound prepared in Example 6(7), the present invention compound having the following physical data was obtained by the same procedure as Example 2.

TLC: Rf 0.29 (acetone: benzene=1:19); NMR (CDCl$_3$): δ 8.33 (1H, m), 7.74 (1H, d, J=8.8 Hz), 7.33 (12H, m), 6.74 (1H, d, J=7.7 Hz), 5.30 (1H, s), 4.82 (2H, s), 4.17 (2H, s), 3.91 (1H, m), 3.83 (3H, s), 3.44 (2H, d, J=5.2 Hz), 2.70 (1H, dd, J=5.3, 13.9 Hz), 2.62 (1H, dd, J=2.0, 7.2 Hz), 2.54 (1H, d, J=3.8 Hz).

EXAMPLE 8(8)

2-{5-[2-(2RS-Hydroxy-3-phenoxypropoxy)ethyl]-1-naphthyloxy}acetic Acid Methyl Ester

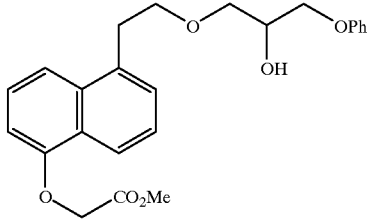

By using the compound prepared in Example 7, the present invention compound having the following physical data was obtained by the same procedure as Example 2.

TLC: Rf 0.37 (AcOEt:CH$_2$Cl$_2$=1:9); NMR (CDCl$_3$): δ 8.29 (1H, m), 7.69 (1H, d, J=8 Hz), 7.47–7.20 (5H, m), 7.01–6.82 (3H, m), 6.71 (1H, d, J=8 Hz), 4.82 (2H, s), 4.12 (1H, m), 3.95 (2H, d, J=5.5 Hz), 3.96–3.77 (5H, m), 3.62 (2H, m), 3.35 (2H, t, J=7 Hz), 2.44 (1H, d, J=3 Hz).

EXAMPLE 9

2-{5-[2-(2RS-Hydroxy-3-(4-chlorophenoxy)propylthio)ethyl]-1-naphthyloxy}acetic Acid

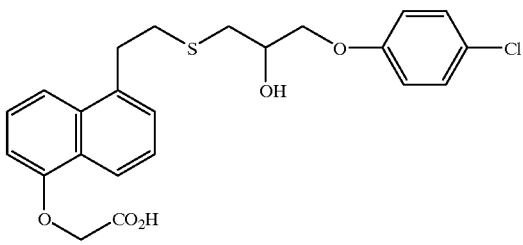

By using the compound prepared in Example 8, the present invention compound having the following physical data was obtained by the same procedure as Example 3.

TLC: Rf 0.61 (MeOH:CHCl$_3$:AcOH=1:8:1); MS (APCI): m/z 445, 447 (3:1), (M–H)+; NMR (DMSO-d6): δ 13.08 (1H, brs), 8.15 (1H, t, J=4.4 Hz), 7.63 (1H, d, J=8.8 Hz), 7.43 (3H, m), 7.31 (2H, d, J=8.8 Hz), 6.95 (2H, d, J=8.8 Hz), 6.89 (1H, d, J=8.8 Hz), 5.29 (1H, m), 4.87 (2H, s), 3.95 (3H, m), 3.30 (2H, m), 2.90 (2H, t, J=7 Hz), 2.80 (1H, dd, J=14, 4 Hz), 2.70 (1H, dd, J=14, 6 Hz).

EXAMPLE 9(1)

2-{5-[2-(2RS-Hydroxy-3-(4-methylphenoxy)propylthio)ethyl]-1-naphthyloxy}acetic Acid

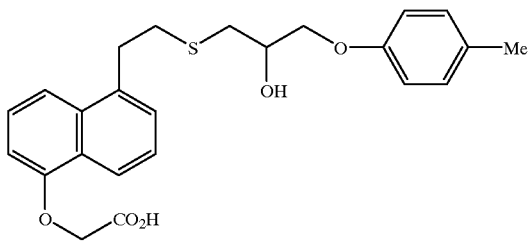

By using the compound prepared in Example 8(1), the present invention compound having the following physical data was obtained by the same procedure as Example 3.

TLC: Rf 0.60 (MeOH:CHCl$_3$:ACOH=1:18:1); MS (APCI): m/z 425 (M−H)+; NMR (DMSO-d6): δ 13.07 (1H, brs), 8.14 (1H, t, J=4.2 Hz), 7.63 (1H, d, J=8.6 Hz), 7.43 (3H, m), 7.07 (2H, d, J=8.2 Hz), 6.89 (1H, d, J=8.6 Hz), 6.72 (2H, d, J=8.2 Hz), 5.23 (1H, d, J=5 Hz), 4.87 (2H, s), 3.95 (3H, m), 3.30 (2H, m), 2.90 (2H, t, J=8 Hz), 2.82 (1H, dd, J=14, 6 Hz), 2.70 (1H, dd, J=14, 6 Hz), 2.22 (3H, s).

EXAMPLE 9(2)

2-{5-[2-(2RS-Hydroxy-3-(4-methyoxyphenoxy)propylthio)ethyl]-1-naphthyloxy}acetic Acid

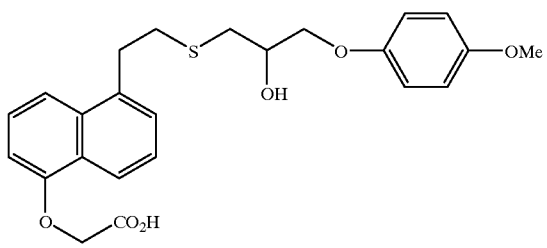

By using the compound prepared in Example 8(2), the present invention compound having the following physical data was obtained by the same procedure as Example 3.

TLC: Rf 0.56 (MeOH:CHCl$_3$:AcOH=1:18:1); MS (APCI): m/z 441 (M−H)+; NMR (DMSO-d6): δ 13.07 (1H, brs), 8.14 (1H, t, J=6 Hz), 7.63 (1H, d, J=8.4 Hz), 7.43 (3H, m), 6.89 (1H, d, J=6 Hz), 6.85 (4H, s), 5.22 (1H, d, J=4.4 Hz),4.88 (2H, s), 3.90 (3H, m), 3.69 (3H, s), 3.25 (2H, m), 2.88 (2H, t, J=9 Hz), 2.82 (1H, dd, J=13, 4 Hz), 2.68 (1H, dd, J=13, 6 Hz).

EXAMPLE 9(3)

2-{5-[2-(2RS-Hydroxy-3-diphenylmethoxypropylthio)ethyl]-1-naphthyloxy}acetic Acid

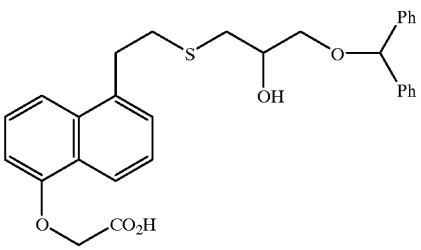

By using the compound prepared in Example 8(3), the present invention compound having the following physical data was obtained by the same procedure as Example 3.

TLC: Rf 0.60 (MeOH:CHCl$_3$ :AcOH=10:100:1); MS (FAB): m/z 503 (M+1)+, 229, 207; NMR (CDCl$_3$): δ 8.25 (1H, d, J=8.0 Hz), 7.63 (1H, d, J=8.4 Hz), 7.33 (13H, m), 6.74 (1H, d, J=7.7 Hz), 5.38 (1H, s), 4.84 (2H, s), 3.94 (1H, m), 3.51 (2H, d, J=4.8 Hz), 3.31 (2H, m), 2.89 (2H, m), 2.78 (1H, dd, J=5.6, 13.8 Hz), 2.66 (1H, dd, J=7.2, 1 3.8 Hz).

EXAMPLE 9(4)

2-{5-[2-(2 RS-Hydroxy-3-phenylthiopropylthio)ethyl]-1-naphthyloxy}acetic Acid

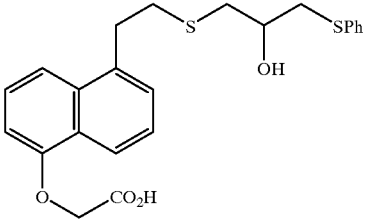

By using the compound prepared in Example 8(5), the present invention compound having the following physical data was obtained by the same procedure as Example 3.

TLC: Rf 0.56 (MeOH:CHCl$_3$:AcOH=1:18:1); MS (APCI): m/z 427 (M−H)+; NMR (DMSO-d6): δ 13.09 (1H, brs), 8.14 (1H, dd, J=7, 3.2 Hz), 7.62 (1H, d, J=8.6 Hz), 7.50–7.22 (7H, m), 7.22–7.10 (1H, m), 6.89 (1H, d, J=7.2 Hz), 5.31 (1H, d, J=4.8 Hz), 4.87 (2H, s), 3.78 (1H, m), 3.25 (2H, t, J=8 Hz), 3.16 (1H, dd, J=13, 5 Hz), 3.03 (1H, dd, J=13, 6 Hz), 2.85 (2H, t, J=8 Hz), 2.80 (1H, dd, J=13, 5Hz), 2.69 (1H, dd, J=13, 6 Hz).

EXAMPLE 9(5)

2-[5-(2RS-Hydroxy-3-diphenylmethoxypropylthio)methyl-1-naphthyloxy]acetic Acid

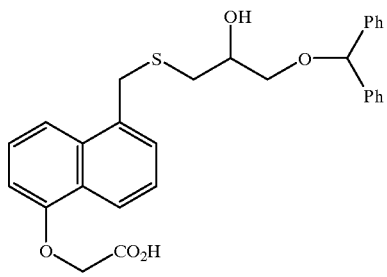

By using the compound prepared in Example 8(6), the present invention compound having the following physical data was obtained by the same procedure as Example 3.

TLC: Rf 0.55 (MeOH:CHCl$_3$:AcOH=10:100:1); MS (FAB): m/z 489 (M+1)+, 338; NMR (CDCl$_3$): δ 8.30 (1H, m), 7.77 (1H, d, J=8.5 Hz), 7.35 (13H, m), 6.76 (1H, d, J=7.9 Hz), 5.34 (1H, s), 4.85 (2H, s), 4.16 (2H, s), 3.94 (1H, m), 3.47 (2H, d, J=5.1 Hz), 2.71 (1H, dd, J=5.2, 13.8 Hz), 2.59 (1H, dd, J=7.2, 13.8 Hz).

EXAMPLE 9(6)

2-{5-[2-(2RS-Hydroxy-3-phenoxypropoxy)ethyl]-1-naphthyloxy}acetic Acid

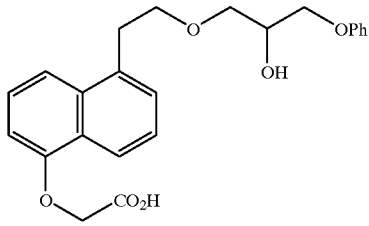

By using the compound prepared in Example 8(8), the present invention compound having the following physical data was obtained by the same procedure as Example 3.

TLC: Rf 0.17 (MeOH:CHCl$_3$=1:3); NMR (DMSO-d6): δ 13.00 (1H, brs), 8.13 (1H, dd, J=8, 2 Hz), 7.66 (1H, d, J=9 Hz), 7.50–7.20 (5H, m), 6.98–6.82 (4H, m), 5.07 (1H, m), 4.87 (2H, s), 4.00–3.10 (9H, m).

EXAMPLE 10

1-Cyanomethoxy-5-[2-(2RS-hydroxy-3-phenoxypropylthio)ethyl]naphthalene

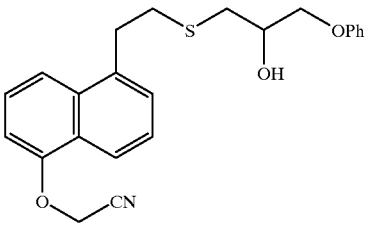

By using bromoacetonitrile instead of bromoacetic acid methyl ester in Example 2 and the compound prepared in Example 1, the present invention compound having the following physical data was obtained by the same procedure as Example 2.

TLC: Rf 0.33 (benzene:AcOEt=17:3); NMR (CDCl$_3$): δ 8.17 (1H, m), 7.73 (1H, d, J=8 Hz), 7.52–7.23 (5H, m), 7.05–6.85 (4H, m), 4.95 (2H, s, —OCH$_2$), 4.20–3.96 (3H, m), 3.38 (2H, t, J=7 Hz), 3.03–2.60 (5H, m).

EXAMPLE 10(1)

1-Cyanomethoxy-5-{2-[2RS-hydroxy-3-(4-chlorophenoxy)propylthio]ethyl}naphthalene

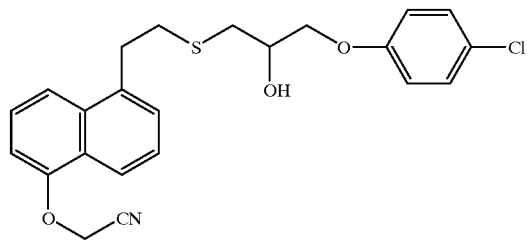

By using the compound prepared in Example 6, the present invention compound having the following physical data was obtained by the same procedure as Example 10.

TLC: Rf 0.45 (acetone:benzene=1:9); MS (EI): m/z 427, 429 (3:1) (M)+, 387, 389 (3:1) (M−40)+; NMR (CDCl$_3$): δ 8.14 (1H, d, J=7.6 Hz), 7.72 (1H, d, J=8.6 Hz), 7.43 (3H, m), 7.24 (2H, d, J=9.2 Hz), 6.93 (1H, d, J=7.6 Hz), 6.82 (2H, d, J=9.2 Hz), 4.97 (2H, s), 4.06 (1H, m), 3.97 (2H, m), 3.36 (2H, t, J=7 Hz), 2.95 (2H, t, J=7 Hz), 2.89 (1H, dd, J=13, 5.2 Hz), 2.75 (1H, dd, J=13, 7 Hz), 2.66 (1H, d, J=4.2 Hz).

EXAMPLE 10(2)

1-Cyanomethoxy-5-{2-[2RS-hydroxy-3-(4-methylphenoxy)propylthio]ethyl}naphthalene

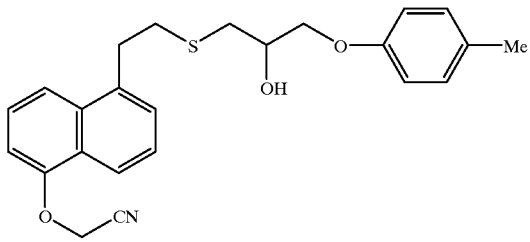

By using the compound prepared in Example 6(1), the present invention compound having the following physical data was obtained by the same procedure as Example 10.

TLC: Rf 0.45 (acetone:benzene=1:9); MS (EI): m/z 407 (M)+, 367 (M−40)+; NMR (DMSO-d6): δ 8.14 (1H, t, J=7.6 Hz), 7.73 (1H, d, J=8.8 Hz), 7.43 (3H, m), 7.08 (2H, d, J=8.8 Hz), 6.94 (1H, d, J=7.6 Hz), 6.80 (2H, d, J=8.2 Hz), 4.96 (2H, s), 4.08 (1H, m), 3.97 (2H, m), 3.37 (2H, t, J=7 Hz), 2.95 (2H, t, J=7 Hz), 2.90 (1H, dd, J=14, 5.2 Hz), 2.75 (1H, dd, J=14, 6.8 Hz), 2.68 (1H, d, J=4.2 Hz), 2.29 (3H, s).

EXAMPLE 10(3)

1-Cyanomethoxy-5-{2-[2RS-hydroxy-3-(4-methoxyphenoxy)propylthio]ethyl}naphthalene

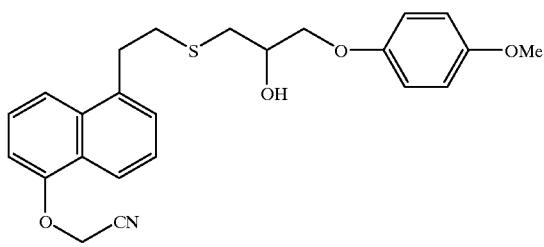

By using the compound prepared in Example 6(2), the present invention compound having the following physical data was obtained by the same procedure as Example 10.

TLC: Rf 0.38 (acetone:benzene=1:9); MS (EI): m/z 423 (M)+; NMR (DMSO-d6): δ 8.16 (1H, t, J=7.5 Hz), 7.73 (1H, d, J=8.6 Hz), 7.46 (3H, m), 6.94 (1H, d, J=7 Hz), 6.83 (4H, s), 4.97 (2H, s), 4.06 (1H, m), 3.97 (2H, m), 3.77 (3H, s), 3.37 (2H, t, J=7.4 Hz), 2.95 (2H, t, J=7.4 Hz), 2.89 (1H, dd, J=14, 6.4 Hz), 2.76 (1H, dd, J=13, 6.8 Hz), 2.68 (1H, d, J=4 Hz).

EXAMPLE 10(4)

1-Cyanomethoxy-5-[2-(2RS-hydroxy-3-diphenylmethoxypropylthio)ethyl]naphthalene

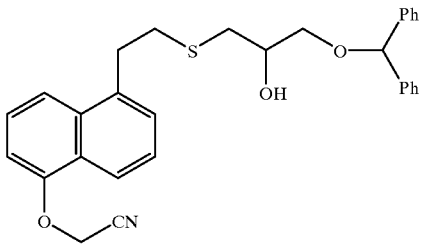

By using the compound prepared in Example 6(3), the present invention compound having the following physical data was obtained by the same procedure as Example 10.

TLC: Rf 0.32 (acetone:benzene=1:19); MS (FAB): m/z 484 (M+1)+, 443,391, 168; NMR (CDCl3): δ 8.13 (1H, d, J=9.2 Hz), 7.72 (1H, d, J=8.7 Hz), 7.34 (13H, m), 6.93 (1H, d, J=7.7 Hz), 5.39 (1H, s), 4.95 (1H, s), 3.95 (1H, m), 3.52 (1H, d, J=5.7 Hz), 3.33 (2H, dd, J=7.3, 9.7 Hz), 2.90 (2H, m), 2.83 (1H, dd, J=5.3, 13.7 Hz), 2.68 (1H, dd, J=7.2, 13.7 Hz), 2.63 (1H, d, J=4.2 Hz).

EXAMPLE 10(5)

1-Cyanomethoxy-5-[2-(2RS-hydroxy-3-phenylthiopropylthio)ethyl]naphthalene

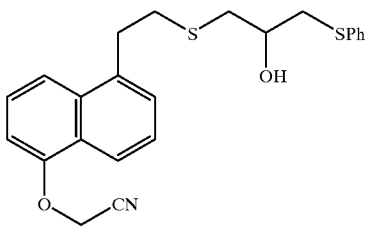

By using the compound prepared in Example 6(5), the present invention compound having the following physical data was obtained by the same procedure as Example 10.

TLC: Rf 0.33 (acetone:benzene=1:19); MS (EI): m/z 409 (M)+; NMR (CDCl3): δ 8.13 (1H, d, J=7.8 Hz), 7.70 (1H, d, J=8.8 Hz), 7.47 (1H, d, J=7.2 Hz), 7.42–7.34 (4H, m), 7.34–7.10 (3H, m), 4.97 (2H, s), 3.82 (1H, m), 3.33 (2H, t, J=7 Hz), 3.15 (1H, dd, J=3.8, 5.2 Hz), 3.03 (1H, dd, J=1 3.8, 6.6 Hz), 2.89 (2H, t, J=7 Hz), 2.84 (1H, dd, J=13.8, 4.6 Hz), 2.68 (1H, dd, J=1 3.8, 7.4 Hz).

EXAMPLE 10(6)

1-Cyanomethoxy-5-[(2RS-hydroxy-3-diphenylmethoxy)propylthiomethyl]naphthalene

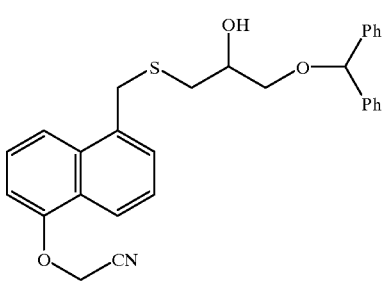

By using the compound prepared in Example 6(6), the present invention compound having the following physical data was obtained by the same procedure as Example 10.

TLC: Rf 0.30 (acetone:benzene=1:19); MS (FAB): m/z 302 (M−C13H11)+, 196, 168; NMR (CDCl$_3$): δ 8.17 (1H, dd, J=2.9, 6.6 Hz), 7.85 (1H, d, J=8.7 Hz), 7.36 (13H, m), 6.95 (1H. d, J=7.7 Hz), 5.35 (1H, s), 4.96 (2H, s), 4.18 (2H, s), 3.94 (1H, m), 3.49 (2H, d, J=5.3 Hz), 2.71 (1H, dd, J=5.2, 13.7 Hz), 2.59 (1H, dd, J=7.2, 13.7 Hz), 2.56 (1H, d, J=7.3 Hz).

EXAMPLE 11

2-{5-[2-(2RS-Hydroxy-3-pheoxypropylamino)ethyl]-1-naphthyloxy}acetic Acid

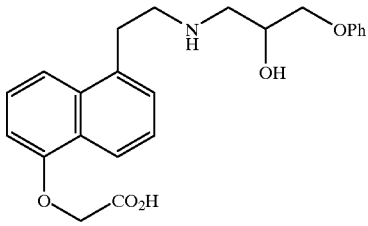

By using the compound prepared in Reference Example 34, the present invention compound having the following physical data was obtained by the same procedure as Example 2→Example 3.

TLC: Rf 0.37 (MeOH:CHCl$_3$:AcOH=2:6:1); MS (FAB): m/z 396 ((M+H)+); NMR (DMSO-d6): δ 8.18 (1H, d, J=8 Hz), 7.40–7.20 (4H, m), 7.14–7.07 (4H, m), 6.72–6.60 (2H, m), 4.58 (2H, s), 4.37–2.90 (12H, m).

EXAMPLE 12

2-{5-[2-(2RS-Hydroxy-3-(1-phenyl-1-(4-chlorophenyl)methoxy)propylthio)ethyl]-1-naphthyloxy}ethanol

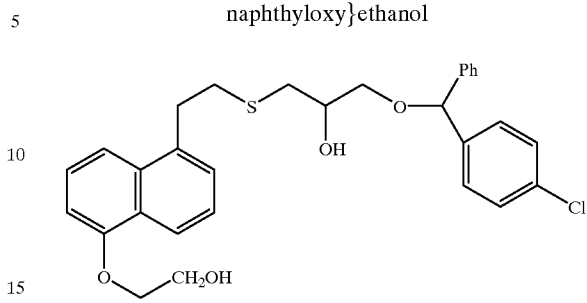

By using 2-bromo ethanol instead of bromoacetic acid methyl ester in Example 2 and the compound prepared in Example 6(4), the present invention compound having the following physical data was obtained by the same procedure as Example 2.

TLC: Rf 0.19 (hexane:AcOEt=2:1); MS (APCI): m/z 523 (M+1)+, 305, 215, 201; NMR (DMSO-d6): δ 8.20 (1H, dd, J=2.1, 7.6 Hz), 7.59 (1H, d, J=8.7 Hz), 7.32 (12H, m), 6.84 (1H, d, J=7.8 Hz), 5.34 (1H, s), 4.27 (2H, m), 4.11 (2H, m), 3.92 (1H, m), 3.49 (2H, d, J=5.4 Hz), 3.32 (2H, dd, J=7.1, 9.6 Hz), 2.90 (2H, m), 2.78 (1H, dd, J=5.3, 11.7 Hz), 2.70 (1H, dd, J=2.3, 7.1 Hz), 2.61 (1H, d, J=2.5 Hz), 2.08 (1H, m).

REFERENCE EXAMPLE 35

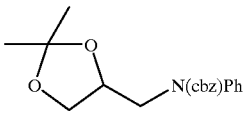

To the solution of benzyloxycarbonylaniline (2.32 g) in anhydrous DMF (30 ml), sodium hydride (426 mg) was added under an atmosphere of argon gas at 0° C. The mixture was stirred for 30 minutes at room temperature. To the mixture, the compound prepared in Reference Example 1 (2.65 g) was added. The mixture was stirred for 1 hour at 80° C. To the reaction mixture, water was added to decompose the superfluous sodium hydride. The mixture was extracted with ethyl acetate, washed with water and a saturated aqueous solution of sodium chloride, dried over with anhydrous magnesium sulfate and concentrated under the reduced pressure. The residue was purified on silica gel column chromatography (hexane:AcOEt=6:1) to give the title compound (2.52 g) having the following physical data.

TLC: Rf 0.36 (hexane:AcOEt=4:1).

REFERENCE EXAMPLE 36

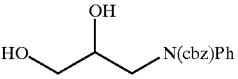

The solution of the compound prepared in Reference Example 35 (2.52 g) in aqueous 80% acetic acid solution (25 ml) was stirred for 10 hours at room temperature. The reaction mixture was concentrated under the reduced pressure. The residue was purified on silica gel column chromatography (CHCl$_3$:MeOH=30:1) to give the title compound (1.69 g) having the following physical data.

TLC: Rf 0.09 (hexane:AcOEt=1:1).

REFERENCE EXAMPLE 37

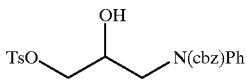

To the solution of the compound prepared in Reference Example 36 (328 mg) in pyridine (2.5 ml), tosylchloride (217 mg) was added under an atmosphere of argon gas at −20° C. The mixture was stirred for 3.5 hours at room temperature. To the reaction mixture, a small amount of water was added. The mixture was stirred for 10 minutes, extracted with ethyl acetate, washed with 1N aqueous solution of hydrochloric acid, water and a saturated aqueous solution of sodium chloride succeedingly, dried over with anhydrous magnesium sulfate and concentrated under the reduced pressure to give the title compound (522 mg) having the following physical data. This residue was used in the next reaction without purification.

TLC: Rf 0.55 (hexane:AcOEt=1:1).

REFERENCE EXAMPLE 38

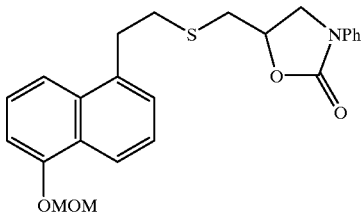

To the ethanol (3.0 ml), sodium hydride (56 mg) was added under an atmosphere of argon gas at 0° C. The mixture was stirred for 10 minutes. To the mixture, the compound prepared in Reference Example 21 (310 mg) and the compound prepared in Reference Example 37 (522 mg) in ethanol (3.0 ml) was added dropwise. The mixture was stirred for 2 hours at room temperature. To the reaction mixture, a saturated aqueous solution of ammonium chloride was added to decompose the superfluous reagent. The reaction mixture was extracted with ethyl acetate, washed with water and a saturated aqueous solution of sodium chloride, dried over with anhydrous magnesium sulfate and concentrated under the reduced pressure. The residue was purified on silica gel column chromatography (hexane:AcOEt=3:1) to give the title compound (427 mg) having the following physical data.

TLC: Rf 0.36 (hexane:AcOEt=2:1).

REFERENCE EXAMPLE 39

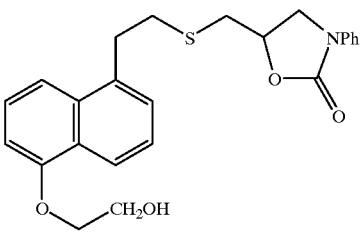

By using the compound prepared in Reference Example 38, the title compound having the following physical data was obtained by the same procedure as Example 1→Example 12.

TLC: Rf 0.20 (hexane:AcOEt=1:1); NMR (CDCl$_3$): δ 8.21 (1H, m), 7.60 (1H, d, J=8.6 Hz), 7.33–7.55 (7H, m), 7.18 (1H, m), 6.85 (1H, d, J=7.6 Hz), 6.69 (1H, m), 4.27 (2H, m), 3.99–4.14 (3H, m), 3.80 (1H, dd, J=6.6, 9.2 Hz), 3.35 (2H, m), 2.91–3.06 (3H, m), 2.78 (1H, dd, J=7.4, 13.8 Hz), 2.11 (1H, t, J=6.4 Hz).

EXAMPLE 13

2-{5-[2-(2RS-Hydroxy-3-phenylaminopropylthio) ethyl]-1-naphthyloxy}ethanol

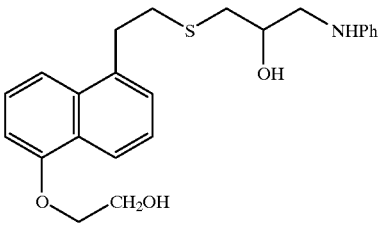

To the solution of the compound prepared in Reference Example 39 (138 mg) in methanol (10 ml), aqueous 40% sodium hydroxide solution (0.5 ml) was added at room temperature. The solution was stirred for 7 days. The mixture was concentrated to the volume of about 3.0 ml, extracted with ethyl acetate, washed with water and a saturated aqueous solution of sodium chloride, dried over with anhydrous magnesium sulfate and concentrated under the reduced pressure. The residue was purified on silica gel column chromatography (CHCl$_3$:MeOH=50:1) to give the present invention compound (116 mg) having the following physical data.

TLC: Rf 0.62 (MeOH:CHCl$_3$=1:10); MS (APCI): m/z 398 (M+1)+, 380, 245, 215; NMR (CDCl$_3$): δ 8.21 (1H, dd, J=2.2, 7.6 Hz), 7.59 (1H, d, J=8.6 Hz), 7.34–7.48 (3H, m), 7.12–7.24 (2H, m), 6.85 (1H, d, J=7.6 Hz), 6.73 (1H, t, J=7.2 Hz), 6.63 (2H, d, J=7.6 Hz), 4.27 (2H, t, J=4.2H), 3.82–4.18 (4H, m), 3.25–3.38 (3H, m), 3.06 (1H, dd, J=7.4, 13.0 Hz), 2.95 (1H, d, J=8.4 Hz), 2.92 (1H, d, J=9.2 Hz), 2.77 (1H, dd, J=4.4, 13.8 Hz), 2.57–2.68 (2H, m), 2.10 (1H, m).

EXAMPLE 14

1-(Tetrazol-5-yl-methoxy)-5-{2-{2RS-hydroxy-3-(4-methyoxyphenoxy)propylthio]ethyl}naphthalene

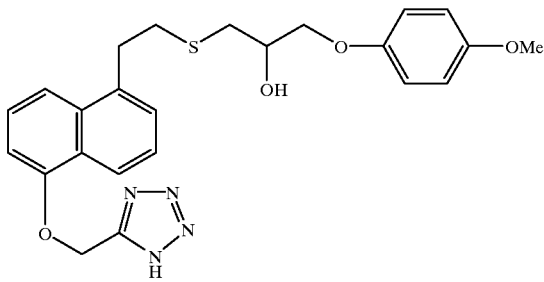

Under an atmosphere of argon gas, the compound prepared in Example 10(3) (178 mg), sodium azide (30 mg) and ammonium chloride (22 mg) were suspended in DMF (5 ml). The suspension was stirred for 20 hours at 80° C. The reaction mixture was cooled to room temperature. To the mixture, water was added. The mixture was stirred, extracted with ethyl acetate three times. The organic layer was washed with water two times and a saturated aqueous solution of sodium chloride one time, dried over with anhydrous magnesium sulfate and concentrated. The white powder obtained was washed with diethylether to give the present invention compound (120 mg) having the following physical data.

TLC: Rf 0.53 (MeOH:CHCl$_3$:AcOH=1:18:1); MS (FAB): m/z 467 (M+H)+; NMR (DMSO-d6): δ 8.19 (1H, t, J=5.2 Hz), 7.69 (1H, d, J=8.4 Hz), 7.49 (1H, d, J=8 Hz), 7.45 (2H, m), 7.16 (1H, d, J=7.4 Hz), 6.84 (4H, s), 5.67 (2H, s), 5.22 (1H, brs), 3.92 (1H, m), 3.90 (2H, m), 3.69 (3H, s), 3.30 (2H, t, J=8.2 Hz), 2.89 (2H, t, J=8.2 Hz), 2.81 (1H, dd, J=13, 5.2 Hz), 2.68 (1H, dd, J=13, 6.2 Hz).

EXAMPLE 15

N-methyl-{5-[2RS-hydroxy-3-(1-phenyl-1-(4-chlorophenyl)methoxy)propylthio]methyl-1-naphthyloxy}acetic Acid Amide

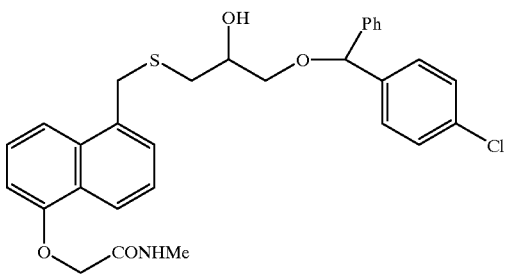

To the solution of the compound prepared in Example 8(7) (325 mg) in THF (3.0 ml), aqueous 40% methylamine solution (0.6 ml) was added. The solution was stirred for 2.5 hours at 45° C. The reaction mixture was diluted with ethyl acetate, washed with 1 N aqueous solution of hydrochloric acid, water and a saturated aqueous solution of sodium chloride, succeedingly, dried over with anhydrous magnesium sulfate and concentrated under the reduced pressure. The residue was purified on silica gel column chromatography (CHCl$_3$:MeOH=30:1) to give the present invention compound (312 mg) having the following physical data.

TLC: Rf 64 (MEOH:CHCl$_3$=1:10); MS (FAB): m/z 536 (M+1)+, 334, 261, 228, 201; NMR (CDCl$_3$): δ 8.18 (1H, m), 7.78 (1H, d, J=8.6 Hz), 7.34 (12H, m), 6.83 (1H, d, J=7.7 Hz), 6.58 (1H, brs), 5.32 (1H, s), 4.70 (2H, s), 4.18 (2H, s), 3.93 (1H, m), 3.46 (2H, d, J=5.1 Hz), 2.93 (3H, d, J=5.0 Hz), 2.71 (1H, dd, J=5.2, 13.8 Hz), 2.63 (1H, dd, J=1.8, 7.2 Hz), 2.56 (1H, d, J=4.0 Hz).

REFERENCE EXAMPLE 40

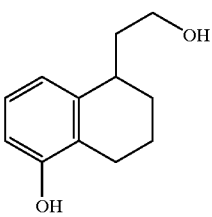

To the solution of 1-(2-hydroxy-ethyliden)-5-hydroxy-1,2,3,4-tetrahydronaphthalene (2.1 g) in ethanol (15 ml), 10% Pd—C (200 mg) was added under an atmosphere of argon gas. The mixture was stirred vigorously under an atmosphere of H$_2$ gas for 1 hour at room temperature. The reaction mixture was filtrated by Celite (Registered trade mark). The filtrate was concentrated under the reduced pressure to give the title compound (1.74 g) having the following physical data.

TLC: Rf 0.40 (hexane:AcOEt=2:1).

EXAMPLE 16

1-{2-[5-Hydroxy-1-(1,2,3,4-tetrahydronaphthyl)]ethylthio}-3-phenoxy-2RS-propanol

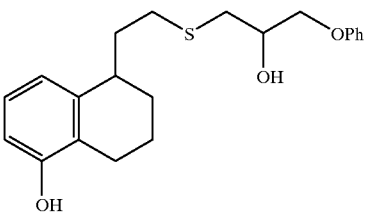

By using the compound prepared from the compound prepared in Reference Example 40 by the same procedure as Reference Example 12→Reference Example 21, and the compound prepared in Reference Example 5, the present invention compound having the following physical data was obtained by the same procedure as Reference Example 24→Example 1.

TLC: Rf 0.36 (hexane:AcOEt=2:1); NMR (CDCl$_3$): δ 7.30 (2H, m), 6.96 (4H, m), 6.75 (1H, d, J=7.9 Hz), 6.61 (1H, d, J=7.9 Hz), 4.75 (1H, m), 4.10 (3H, m), 2.50–3.00 (7H, m), 1.60–2.05 (6H, m).

EXAMPLE 17

2-{5-[2-(2RS-Hydroxy-3-phenoxypropylthio)ethyl]-1-(5,6,7,8-tetrahydronaphthyloxy)}acetic Acid Methyl Ester

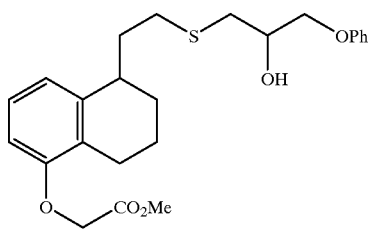

By using the compound prepared in Example 16, the present invention compound having the following physical data was obtained by the same procedure as Example 2.

TLC: Rf 0.33 (acetone:benzene=1:19); NMR (CDCl$_3$): δ 7.29 (2H, m), 7.00 (4H, m), 6.82 (1H, d, J=4.6 Hz), 6.52 (1H, d, J=4.8), 4.63 (2H, s), 4.10 (3H, m), 3.80 (3H, s), 2.55–2.97 (8H, m), 1.60–2.10 (6H, m).

EXAMPLE 18

2-{5-[2-(2RS-Hydroxy-3-phenoxypropylthio)ethyl]-1-(5,6,7,8-tetrahydronaphthyloxy)}acetic Acid

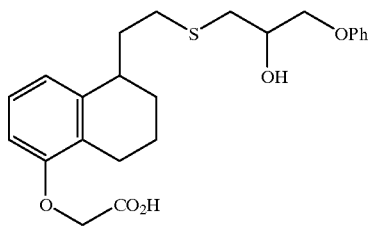

By using the compound prepared in Example 17, the present invention compound having the following physical data was obtained by the same procedure as Example 3.

TLC: Rf 0.5 (MeOH:CHCl$_3$:AcOH=10:100:1); MS (APCI): m/z 415 (M−1)+, 357, 263, 93; NMR (CDCl$_3$): δ 7.30 (2H, m), 6.82–7.13 (5H, m), 6.55 (1H, d, J=8.0 Hz), 4.66 (2H, s), 4.09 (3H, m), 2.50–2.98 (7H, m), 1.60–2.10 (6H, m).

EXAMPLE 19

1-Cyanomethoxy-5-[2-(2RS-hydroxy-3-phenoxypropylthio)ethyl]-5,6,7,8-tetrahydronaphthalene

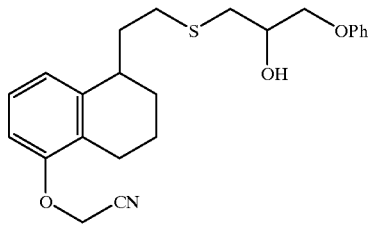

By using the compound prepared in Example 16, the present invention compound having the following physical data was obtained by the same procedure as Example 10.

TLC: Rf 0.33 (acetone:benzene=1:19); MS (EI): m/z 397 (M)+, 304, 286, 245, 213, 184, 173, 157, 145; NMR (CDCl$_3$): δ 7.30 (2H, m), 7.13 (1H, dd, J=8.0, 8.0 Hz), 6.95 (4H, m), 6.71 (1H, d, J=8.0 Hz), 4.76 (2H, s), 4.10 (3H, m), 2.50–3.00 (8H, m), 1.54–2.08 (6H, m).

FORMULATION EXAMPLE 1

The following compounds were admixed in conventional method and punched out to obtain 100 tablets each containing 5 mg of active ingredient.

| | |
|---|---|
| 2-{5-[2-(2RS-hydroxy-3-phenoxypropylthio)ethyl]-1-naphthyloxy}acetic acid | 500 mg |
| Carboxymethylcellulose calcium | 200 mg |
| Magnesium stearate | 100 mg |
| Micro crystalline cellulose | 9.2 g |

What is claimed is:

1. A naphthyloxyacetic acid derivative of the general formula (I)

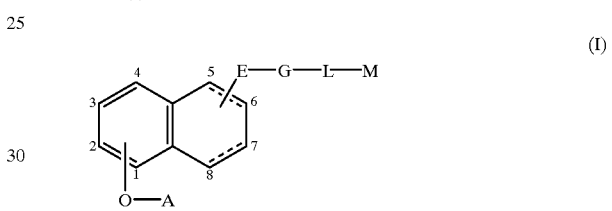

wherein A is
(C1–4 alkylene)-COOR$^1$ in which R$^1$ is hydrogen or C1–4 alkyl,

E is
(i) single bond or
(ii) C1–6 alkylene;

G is —NR$^4$— in which, R$^4$ is hydrogen or C1–4 alkyl;

L is
(i) C1–6 alkylene,
(ii) —(CH$_2$)$_m$—CH═CH—(CH$_2$)$_n$— in which m is 0 or an integer of 1–3, n is 0 or an integer of 1–3 or
(iii) —(CH$_2$)$_x$—CH(OH)—(CH$_2$)$_y$— in which x is an integer of 1–3, y is 0 or an integer of 1–3;

M is

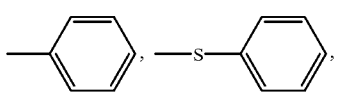

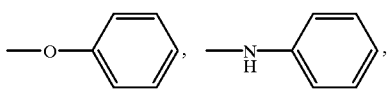

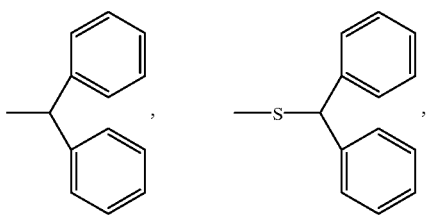

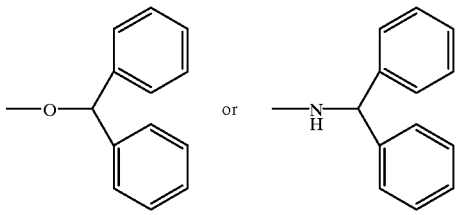

in which each phenyl group may be substituted by 1–3 of C1–4 alkyl, C1–4 alkoxy, halogen, nitro or trifluoromethyl;

with the proviso that, (1) when n in L is 0, M is

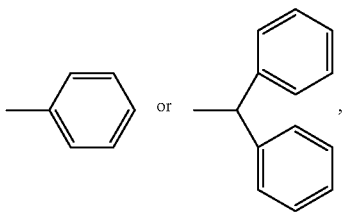

in which each phenyl group may be substituted by 1–3 of C1–4 alkyl, C1–4 alkoxy, halogen, nitro or trifluoromethyl, (2) when y in L is 0, M is

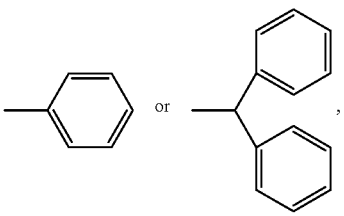

in which each phenyl group may be substituted by 1–3 of C1–4 alkyl, C1–4 alkoxy, halogen, nitro or trifluoromethyl, in which $R^1$ is the same meaning as defined above, or non-toxic salt thereof, non-toxic acid addition salt thereof or their hydrate.

2. A compound according to claim 1, wherein L is $-(CH_2)_m-CH=CH-(CH_2)_n-$ or $-(CH_2)_x-CH(OH)-(CH_2)_y-$.

3. A compound according to claim 1, which is 2-{5-[2-(2RS-hydroxy-3-phenoxypropylamino)ethyl]-1-naphthyloxy}acetic acid.

4. A pharmaceutical composition which comprises a carrier and an effective amount of naphthyloxyacetic acid derivative of the formula (I) depicted in claim 1, non-toxic salt thereof, non-toxic acid addition salt thereof or their hydrate.

5. A prostaglandin $E_2$ antagonist or agonist which comprises a naphthyloxyacetic acid derivative of the formula (I) depicted in claim 1, non-toxic salt thereof, non-toxic acid addition salt thereof or their hydrate.

6. 1-[2-(5-hydroxy-1-naphthyl)ethylamino]-3-phenoxy-2RS-propanol.

* * * * *